US008445250B2

(12) United States Patent
Isaksen et al.

(10) Patent No.: US 8,445,250 B2
(45) Date of Patent: May 21, 2013

(54) FEED SUPPLEMENT

(75) Inventors: Mai Faurschou Isaksen, Braband (DK);
Rikke Høegh Lorentsen, Braband (DK);
Peter Plumstead, Malborough (GB);
Luis Fernando Romero Millán,
Malborough (GB); Susan Madrid,
Millbrae, CA (US); Cherry Lin,
Sunnyvale, CA (US); Michael Ward,
San Francisco, CA (US); **Masoud
Rajabi Zargahi**, Aarhus N. (DK)

(73) Assignee: DuPont Nutrition BioSciences ApS,
Copenhagen (DK)

( * ) Notice: Subject to any disclaimer, the term of this
patent is extended or adjusted under 35
U.S.C. 154(b) by 0 days.

(21) Appl. No.: 13/265,725

(22) PCT Filed: Apr. 23, 2010

(86) PCT No.: PCT/IB2010/051804
§ 371 (c)(1),
(2), (4) Date: Oct. 21, 2011

(87) PCT Pub. No.: WO2010/122532
PCT Pub. Date: Oct. 28, 2010

(65) Prior Publication Data
US 2012/0107296 A1 May 3, 2012

Related U.S. Application Data

(60) Provisional application No. 61/172,272, filed on Apr. 24, 2009, provisional application No. 61/312,413, filed on Mar. 10, 2010.

(30) Foreign Application Priority Data

May 20, 2009 (GB) .................................. 0908770.1
Dec. 23, 2009 (GB) .................................. 0922467.6

(51) Int. Cl.
*C12N 9/14* (2006.01)
(52) U.S. Cl.
USPC .......................................... 435/195; 435/196

(58) Field of Classification Search
USPC ................................ 435/195, 196; 436/53, 61
See application file for complete search history.

(56) References Cited

U.S. PATENT DOCUMENTS

| 5,989,600 | A | 11/1999 | Nielsen et al. | |
|---|---|---|---|---|
| 6,110,719 | A | 8/2000 | Kretz | |
| 6,410,305 | B1 | 6/2002 | Miller et al. | |
| 2007/0298145 | A1* | 12/2007 | Miasnikov et al. | 426/61 |
| 2008/0220498 | A1 | 9/2008 | Cervin et al. | |
| 2009/0220646 | A1* | 9/2009 | Street et al. | 426/54 |

FOREIGN PATENT DOCUMENTS

| EP | 1059041 A1 | 12/2000 |
|---|---|---|
| EP | 1721527 A2 | 11/2006 |
| WO | 9844804 A1 | 10/1998 |
| WO | WO 98/45453 * | 10/1998 |
| WO | 2004015084 A2 | 2/2004 |
| WO | 2005087918 A2 | 9/2005 |
| WO | 2006043178 A2 | 4/2006 |
| WO | WO 2006/043178 * | 4/2006 |
| WO | 2007128160 A1 | 11/2007 |
| WO | 2008097619 A2 | 8/2008 |
| WO | 2009061378 A2 | 5/2009 |
| WO | 2009129489 A2 | 10/2009 |

OTHER PUBLICATIONS

Mulyantini N. et al. The Effect of Xylanase, Phytase and Lipase Supplementation on the Performance of Broiler Chickens Fed a Diet With a High Level of Rice Bran. Australian Poultry Science Symposium 17:305-307, 2005.*
Database WPI Week 200825, Thomson Scientific, London, GB: An 2008-D29883, XP002602759 and CN 101 063 113 A (Feed Inst Chinese Agric Acad) Oct. 31, 2007 abstract.
Bogar, Barbara et al.: "Production of phytase by Mucor racemosus in solid-state fermentation." Biotechnology Progress, vol. 19, No. 2, Mar. 2003, pp. 312-319.

* cited by examiner

*Primary Examiner* — Ralph Gitomer
(74) *Attorney, Agent, or Firm* — Shook, Hardy & Bacon LLP

(57) ABSTRACT

The present invention relates to a feed supplement comprising a phytase and a lipolytic enzyme, wherein said lipolytic enzyme has lipase activity at a pH in the range of about pH1.5 to about pH3.5.

19 Claims, 32 Drawing Sheets

Amino acid sequence of wild-type *Buttiauxella* sp.
P1-29 phytase (SEQ ID NO: 1)

NDTPASGYQVEKVVILSRHGVRAPTKMTQTMRDVTPNTWPEWPVKLGYITPRGEHLISLMGGFYRQKF
QQQGILSQGSCPTPNSIYVWADVDQRTLKTGEAFLAGLAPQCGLTIHHQQNLEKADPLFHPVKAGTCS
MDKTQVQQAVEKEAQTPIDNLNQHYIPFLALMNTTLNFSTSAWCQKHSADKSCDLGLSMPSKLSIKDN
GNKVALDGAIGLSSTLAEIFLLEYAQGMPQAAWGNIHSEQEWASLLKLHNVQFDLMARTPYIARHNGT
PLLQAISNALNPNATESKLPDISPDNKILFIAGHDTNIANIAGMLNMRWTLPGQPDNTPPGGALVFER
LADKSGKQYVSVSMVYQTLEQLRSQTPLSLNQPAGSVQLKIPGCNDQTAEGYCPLSTFTRVVSQSVEP
GCQLQ

FIG. 1.

**Amino acid sequence of a variant of *Buttiauxella* sp. P1-29 phytase (SEQ ID NO: 2)**

NDTPASGYQVEKVVILSRHGVRAPTKMTQTMRDVTPYTWPEWPVKLGYITPRGEHLISLMGGFYRQKF
QQQGILPQGSCPTPNSIYVWTDVAQRTLKTGEAFLAGLAPQCGLTIHHQQNLEKADPLFHPVKAGICS
MDKTQVQQAVEKEAQTPIDNLNQRYIPELALMNTVLNFSKSPWCQKHSADKPCDLALSMPSRLSIKDN
GNEVSLDGAIGLSSTLAEIFLLEYAQGMPQAAWGNIHSEQEWALLLKLHNVYFDLMERTPYIARHKGT
PLLQAISNALNPNATESKLPDISPDNKILFIAGHDTNIANIAGMLNMRWTLPGQPDNTPPGGALVFER
LADKSGKQYVSVSMVYQTLEQLRSQTPLSLNQPPGSVQLKIPGCNDQTAEGYCPLSTFTRVVSQSVEP
GCQLQ

*FIG. 2.*

|  |  | 1 | 50 |
|---|---|---|---|
| (SEQ ID:4) BP-110 | (1) | NDTPASGYQVEKVVILSRHGVRAPTKMTQTMRDVTPYTWPEWPVKLGYIT | |
| (SEQ ID:2) BP-112 | (1) | NDTPASGYQVEKVVILSRHGVRAPTKMTQTMRDVTPYTWPEWPVKLGYIT | |
| (SEQ ID:5) BP-111 | (1) | NDTPASGYQVEKVVILSRHGVRAPTKMTQTMRDVTPYTWPEWPVKLGYIT | |
| (SEQ ID:3) BP-17 | (1) | NDTPASGYQVEKVVILSRHGVRAPTKMTQTMRDVTPNTWPEWPVKLGYIT | |
| (SEQ ID:1) Buttiauxella-WT | (1) | NDTPASGYQVEKVVILSRHGVRAPTKMTQTMRDVTPNTWPEWPVKLGYIT | |
|  |  | 51 | 100 |
| BP-110 | (51) | PRGEHLISLMGGFYRQKFQQQGILSQSSCPTPNSIYVWTDVAQRTLKTGE | |
| BP-112 | (51) | PRGEHLISLMGGFYRQKFQQQGILPQGSCPTPNSIYVWTDVAQRTLKTGE | |
| BP-111 | (51) | PRGEHLISLMGGFYRQKFQQQGILPRGSCPTPNSIYVWTDVAQRTLKTGE | |
| BP-17 | (51) | PRGEHLISLMGGFYRQKFQQQGILSQGSCPTPNSIYVWTDVAQRTLKTGE | |
| Buttiauxella-WT | (51) | PRGEHLISLMGGFYRQKFQQQGILSQGSCPTPNSIYVWADVDQRTLKTGE | |
|  |  | 101 | 150 |
| BP-110 | (101) | AFLAGLAPQCGLTIHHQQNLEKADPLFHPVKAGICSMDKTQVQQAVEKEA | |
| BP-112 | (101) | AFLAGLAPQCGLTIHHQQNLEKADPLFHPVKAGICSMDKTQVQQAVEKEA | |
| BP-111 | (101) | AFLAGLAPQCGLTIHHQQNLEKADPLFHPVKAGICSMDKTQVQQAVEKEA | |
| BP-17 | (101) | AFLAGLAPQCGLTIHHQQNLEKADPLFHPVKAGICSMDKTQVQQAVEKEA | |
| Buttiauxella-WT | (101) | AFLAGLAPQCGLTIHHQQNLEKADPLFHPVKAGTCSMDKTQVQQAVEKEA | |
|  |  | 151 | 200 |
| BP-110 | (151) | QTPIDNLNQRYIPELALMNTVLNFSKSPWCQKHSADKPCDLALSMPSRLS | |
| BP-112 | (151) | QTPIDNLNQRYIPELALMNTVLNFSKSPWCQKHSADKPCDLALSMPSRLS | |
| BP-111 | (151) | QTPIDNLNQRYIPELALMNTILNFSKSPWCQKHSADKPCDLALSMPSKLS | |
| BP-17 | (151) | QTPIDNLNQHYIPSLALMNTTLNFSKSPWCQKHSADKSCDLGLSMPSKLS | |
| Buttiauxella-WT | (151) | QTPIDNLNQHYIPFLALMNTTLNFSTSAWCQKHSADKSCDLGLSMPSKLS | |
|  |  | 201 | 250 |
| BP-110 | (201) | IKDNGNEVSLDGAIGLSSTLAEIFLLEYAQGMPQAAWGNIHSEQEWALLL | |
| BP-112 | (201) | IKDNGNEVSLDGAIGLSSTLAEIFLLEYAQGMPQAAWGNIHSEQEWALLL | |
| BP-111 | (201) | IKDNGNEVSLDGAIGLSSTLAEIFLLEYAQGMPQVAWGNIHSEQEWALLL | |
| BP-17 | (201) | IKDNGNEVSLDGAIGLSSTLAEIFLLEYAQGMPQAAWGNIHSEQEWALLL | |
| Buttiauxella-WT | (201) | IKDNGNKVALDGAIGLSSTLAEIFLLEYAQGMPQAAWGNIHSEQEWASLL | |
|  |  | 251 | 300 |
| BP-110 | (251) | KLHNVYFDLMERTPYIARHKGTPLLQAISNALNPNATESKLPDISPDNKI | |
| BP-112 | (251) | KLHNVYFDLMERTPYIARHKGTPLLQAISNALNPNATESKLPDISPDNKI | |
| BP-111 | (251) | KLHNVYFDLMERTPYIARHKGTPLLQAISNALNPNATESKLPDISPDNKI | |
| BP-17 | (251) | KLHNVYFDLMERTPYIARHKGTPLLQAISNALNPNATESKLPDISPDNKI | |
| Buttiauxella-WT | (251) | KLHNVQFDLMARTPYIARHNGTPLLQAISNALNPNATESKLPDISPDNKI | |
|  |  | 301 | 350 |
| BP-110 | (301) | LFIAGHDTNIANIAGMLNMRWTLPGQPDNTPPGGALVFERLADKSGKQYV | |
| BP-112 | (301) | LFIAGHDTNIANIAGMLNMRWTLPGQPDNTPPGGALVFERLADKSGKQYV | |
| BP-111 | (301) | LFIAGHDTNIANIAGMLNMRWTLPGQPDNTPPGGALVFERLADKSGKQYV | |
| BP-17 | (301) | LFIAGHDTNIANIAGMLNMRWTLPGQPDNTPPGGALVFERLADKSGKQYV | |
| Buttiauxella-WT | (301) | LFIAGHDTNIANIAGMLNMRWTLPGQPDNTPPGGALVFERLADKSGKQYV | |
|  |  | 351 | 400 |
| BP-110 | (351) | SVSMVYQTLEQLRSQTPLSLNQPPGSVQLKIPGCNDQTAEGYCPLSTFTR | |
| BP-112 | (351) | SVSMVYQTLEQLRSQTPLSLNQPPGSVQLKIPGCNDQTAEGYCPLSTFTR | |
| BP-111 | (351) | SVSMVYQTLEQLRSQTPLSLNQPPGSVQLKIPGCNDQTAEGYCPLSTFTR | |
| BP-17 | (351) | SVSMVYQTLEQLRSQTPLSLNQPAGSVQLKIPGCNDQTAEGYCPLSTFTR | |
| Buttiauxella-WT | (351) | SVSMVYQTLEQLRSQTPLSLNQPAGSVQLKIPGCNDQTAEGYCPLSTFTR | |
|  |  | 401 413 | |
| BP-110 | (401) | VVSQSVEPGCQLQ | |
| BP-112 | (401) | VVSQSVEPGCQLQ | |
| BP-111 | (401) | VVSQSVEPGCQLQ | |
| BP-17 | (401) | VVSQSVEPGCQLQ | |
| Buttiauxella-WT | (401) | VVSQSVEPGCQLQ | |

*FIG. 3.*

BP-11 (SEQ ID NO:6)

HHHHHHNDTPASGYQVEKVVILSRHGVRAPTKMTQTMRDVTPNTWPEWPVKLGYITPRGEHLISLMGG
FYRQKFQQQGILSQGSCPTPNSIYWTDVDQRTLKTGEAFLAGLAPQCGLTIHHQQNLEKADPLFHPV
KAGICSMDKTQVQQAVEKEAQTPIDNLNQHYIPSLALMNTTLNFSKSPWCQKHSADKSCDLGLSMPSK
LSIKDNGNEVSLDGAIGLSSTLAEIFLLEYAQGMPQAAWGNIHSEQEWALLLKLHNVYFDLMERTPYI
ARHKGTPLLQAISNALNPNATESKLPDISPDNKILFIAGHDTNIANIAGMLNMRWTLPGQPDNTPPGG
ALVFERLADKSGKQYVSVSMVYQTLEQLRSQTPLSLNQPAGSVQLKIPGCNDQTAEGYCPLSTFTRVV
SQSVEPGCQLQ

*FIG. 4.*

SEQ ID NO: 7

1    MFSGRFGVLL TALAALGAAA <u>PAPLAVR</u>SVS TSTLDELQLF AQWSAAAYCS
51   NNIDSKDSNL TCTANACPSV EEASTTMLE FDLTNDFGGT AGFLAADNTN
101  KRLVVAFRGS STIENWIANL DFILEDNDDL CTGCKVHTGF WKAWESAADE
151  LTSKIKSAMS TYSGYTLYFT GHSLGGALAT LGATVLRNDG YSVELYTYGC
201  PRIGNYALAE HITSQGSGAN FRVTHLNDIV PRVPPMDFGF SQPSPEYWIT
251  SGNGASVTAS DIEVIEGINS TAGNAGEATV SVVAHLWYFF AISECLL

LIPASE 3 AMINO ACID SEQUENCE (SIGNAL SEQUENCE IN BOLD, PRO-PEPTIDE BOLD UNDERLINE)

*FIG. 5.*

SEQ ID NO: 8

```
 1  SVSTSTLDEL QLFAQWSAAA YCSNNIDSKD SNLTCTANAC PSVEEASTTM
51  LLEFDLTNDF GGTAGFLAAD NTNKRLVVAF RGSSTIENWI ANLDFILEDN
101 DDLCTGCKVH TGFWKAWESA ADELTSKIKS AMSTYSGYTL YFTGHSLGGA
151 LATLGATVLR NDGYSVELYT YGCPRIGNYA LAEHITSQGS GANFRVTHLN
201 DIVPRVPPMD FGFSQPSPEY WITSGNGASV TASDIEVIEG INSTAGNAGE
251 ATVSVVAHLW YFFAISECLL
```

LIPASE 3 AMINO ACID SEQUENCE (WITHOUT SIGNAL OR PRO-PEPTIDE SEQUENCE)

FIG. 6.

SEQ ID NO:9
WITH SIGNAL SEQUENCE

**ATGTTCTCTGGACGGTTTGGAGTGCTTTTGACAGCGCTTGCTGCGCTGGGTGC
TGCCGCGCCGGCACCGCTTGCTGTGCGG**Agtaggtgtgcccgatgtgagatggttggatagcact
gatgaagggtgaatagGTGTCTCGACTTCCACGTTGGATGAGTTGCAATTGTTCGCGCA
ATGGTCTGCCGCAGCTTATTGCTCGAATAATATCGACTCGAAAGACTCCAACTTG
ACATGCACGGCCAACGCCTGTCCATCAGTCGAGGAGGCCAGTACCACGATGCT
GCTGGAGTTCGACCTgtatgtcactcagatcgcagacatagagcacagctaatttgaacagGACGAAC
GACTTTGGAGGCACAGCCGGTTTCCTGGCCGCGGACAACACCAACAAGCGGCT
CGTGGTCGCCTTCCGGGGAAGCAGCACGATTGAGAACTGGATTGCTAATCTTGA
CTTCATCCTGGAAGATAACGACGACCTCTGCACCGGCTGCAAGGTCCATACTGG
TTTCTGGAAGGCATGGGAGTCCGCTGCCGACGAACTGACGAGCAAGATCAAGT
CTGCGATGAGCACGTATTCGGGCTATACCCTATACTTCACCGGGCACAGTTTGG
GCGGCGCATTGGCTACGCTGGGAGCGACAGTTCTGCGAAATGACGGATATAGC
GTTGAGCTGgtgagtccttcacaaaggtgatggagcgacaatcgggttctgacagtcaatagTACACCTAT
GGATGTCCTCGAATCGGAAACTATGCGCTGGCTGAGCATATCACCAGTCAGGGA
TCTGGGGCCAACTTCCGTGTTACACACTTGAACGACATCGTCCCCGGGTGCCA
CCCATGGACTTTGGATTCAGTCAGCCAAGTCCGGAATACTGGATCACCAGTGGC
AATGGAGCCAGTGTCACGGCGTCGGATATCGAAGTCATCGAGGGAATCAATTCA
ACGGCGGGAAATGCAGGCGAAGCAACGGTGAGCGTTGTGGCTCACTTGTGGTA
CTTTTTTGCGATTTCCGAGTGCCTGCTATAA**

SIGNAL SEQUENCE (BOLD)
INTRONS (LOWER CASE)

*FIG. 7.*

SEQ ID NO:10
WITHOUT SIGNAL SEQUENCE

AgtaggtgtgcccgatgtgagatggttggatagcactgatgaagggtgaatagGTGTCTCGACT
TCCACGTTGGATGAGTTGCAATTGTTCGCGCAATGGTCTGCCGCAGCT
TATTGCTCGAATAATATCGACTCGAAAGACTCCAACTTGACATGCACGG
CCAACGCCTGTCCATCAGTCGAGGAGGCCAGTACCACGATGCTGCTG
GAGTTCGACCTgtatgtcactcagatcgcagacatagagcacagctaatttgaacagGACGA
ACGACTTTGGAGGCACAGCCGGTTTCCTGGCCGCGGACAACACCAAC
AAGCGGCTCGTGGTCGCCTTCCGGGGAAGCAGCACGATTGAGAACTG
GATTGCTAATCTTGACTTCATCCTGGAAGATAACGACGACCTCTGCAC
CGGCTGCAAGGTCCATACTGGTTTCTGGAAGGCATGGGAGTCCGCTG
CCGACGAACTGACGAGCAAGATCAAGTCTGCGATGAGCACGTATTCG
GGCTATACCCTATACTTCACCGGGCACAGTTTGGGCGGCGCATTGGCT
ACGCTGGGAGCGACAGTTCTGCGAAATGACGGATATAGCGTTGAGCT
GgtgagtccttcacaaaggtgatggagcgacaatvgggttctgacagtcaatagTACACCTATG
GATGTCCTCGAATCGGAAACTATGCGCTGGCTGAGCATATCACCAGTC
AGGGATCTGGGGCCAACTTCCGTGTTACACACTTGAACGACATCGTCC
CCCGGGTGCCACCCATGGACTTTGGATTCAGTCAGCCAAGTCCGGAA
TACTGGATCACCAGTGGCAATGGAGCCAGTGTCACGGCGTCGGATAT
CGAAGTCATCGAGGGAATCAATTCAACGGCGGGAAATGCAGGCGAAG
CAACGGTGAGCGTTGTGGCTCACTTGTGGTACTTTTTTGCAGATTTCCG
AGTGCCTGCTATAA

*FIG. 8.*

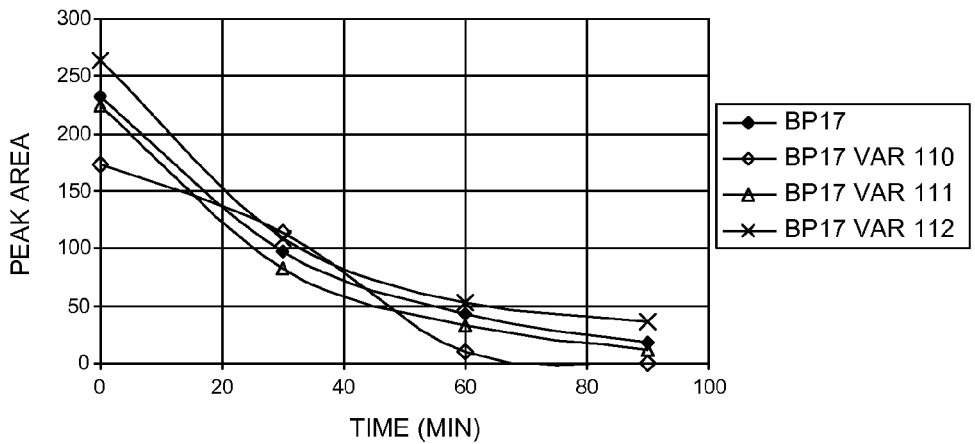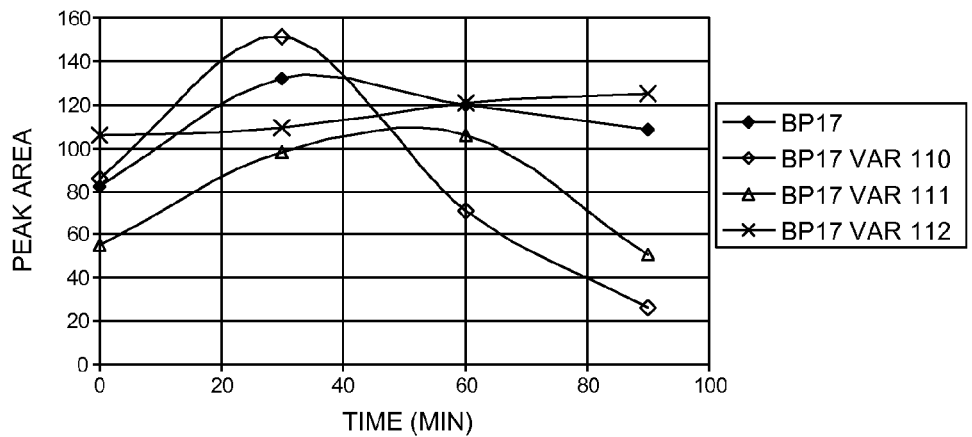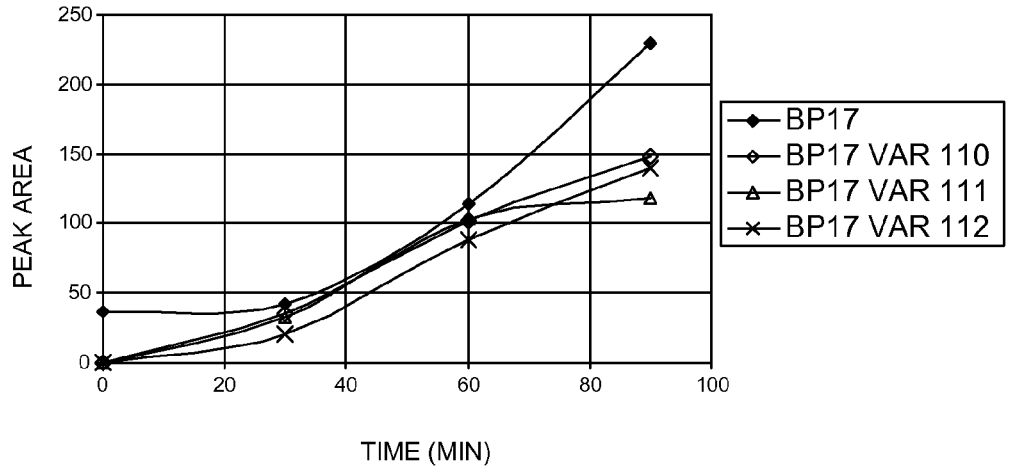
FIG. 16.

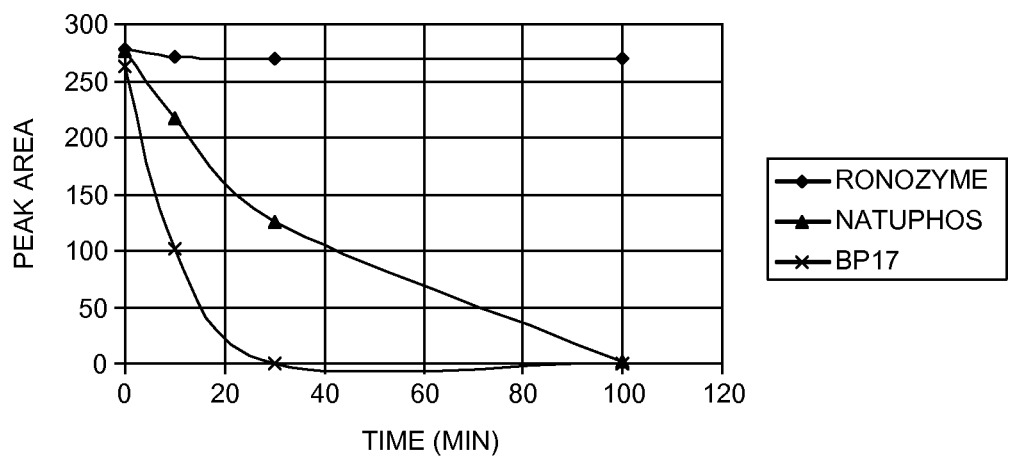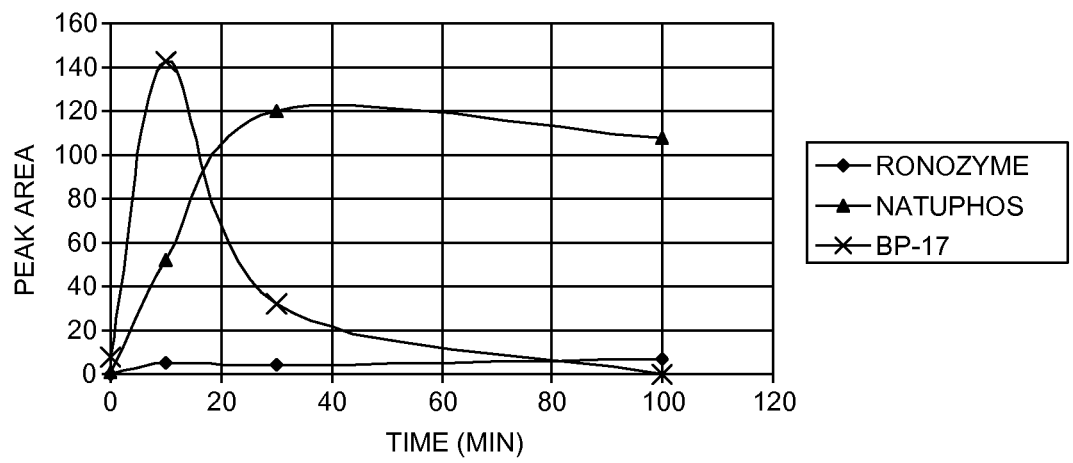
FIG. 17.

A NUCLEIC ACID SEQUENCE ENCODING THE SEQUENCE OF A WILD-TYPE *BUTTIAUXELLA* SP. P1-29

(SEQ ID NO: 11)

AACGACACTCCCGCTTCAGGCTACCAGGTTGAGAAAGTGGTAATACTCAGCCGCCACGGGGTGCGAGC
ACCAACCAAAATGACACAGACCATGCGCGACGTAACACCTAATACCTGGCCCGAATGGCCAGTAAAAT
TGGGTTATATCACGCCACGCGGTGAGCATCTGATTAGCCTGATGGGCGGGTTTTATCGCCAGAAGTTT
CAACAACAGGGCATTTTATCGCAGGGCAGTTGCCCCACACCAAACTCAATTTATGTCTGGGCAGACGT
TGATCAGCGCACGCTTAAAACTGGCGAAGCTTTCCTGGCAGGGCTTGCTCCGGAATGTCATTTAACTA
TTCACCACCAGCAGGACATCAAAAAAGCCGATCCGCTGTTCCATCCGGTGAAAGCGGGCACCTGTTCA
ATGGATAAAACTCAGGTCCAACAGGCCGTTGAAAAAGAAGCTCAAACCCCCATTGATAATCTGAATCA
GCACTATATTCCCTTTCTGGCCTTGATGAATACGACCCTCAACTTTTCGACGTCGGCCTGGTGTCAGA
AACACAGCGCGGATAAAAGCTGTGATTTAGGGCTATCCATGCCGAGCAAGCTGTCGATAAAAGATAAT
GGCAACAAAGTCGCTCTCGACGGGGCCATTGGCCTTTCGTCTACGCTTGCTGAAATTTTCCTGCTGGA
ATATGCGCAAGGGATGCCGCAAGCGGCGTGGGGGAATATTCATTCAGAGCAAGAGTGGGCGTCGCTAC
TGAAACTGCATAACGTCCAGTTTGATTTGATGGCACGCACGCCTTATATCGCCAGACATAACGGCACG
CCTTTATTGCAGGCCATCAGCAACGCGCTGAACCCGAATGCCACCGAAAGCAAACTGCCTGATATCTC
ACCTGACAATAAGATCCTGTTTATTGCCGGACACGATACCAATATTGCCAATATCGCAGGCATGCTCA
ACATGCGCTGGACGCTACCTGGGCAACCCGATAACACCCCTCCGGGCGGCGCTTTAGTCTTTGAGCGT
TTGGCCGATAAGTCAGGGAAACAATATGTTAGCGTGAGCATGGTGTATCAGACTCTCGAGCAGTTGCG
CTCCCAAACACCACTTAGCCTTAATCAACCTGCGGGAAGCGTACAGCTAAAAATTCCTGGCTGTAACG
ATCAGACGGCTGAAGGATANTGCCCGCTGTCGACGTTCACTCGCGNGGTTAGCCAAAGCGTGGAACCA
GGCTGCCAGCTACAGTAA

*FIG. 22.*

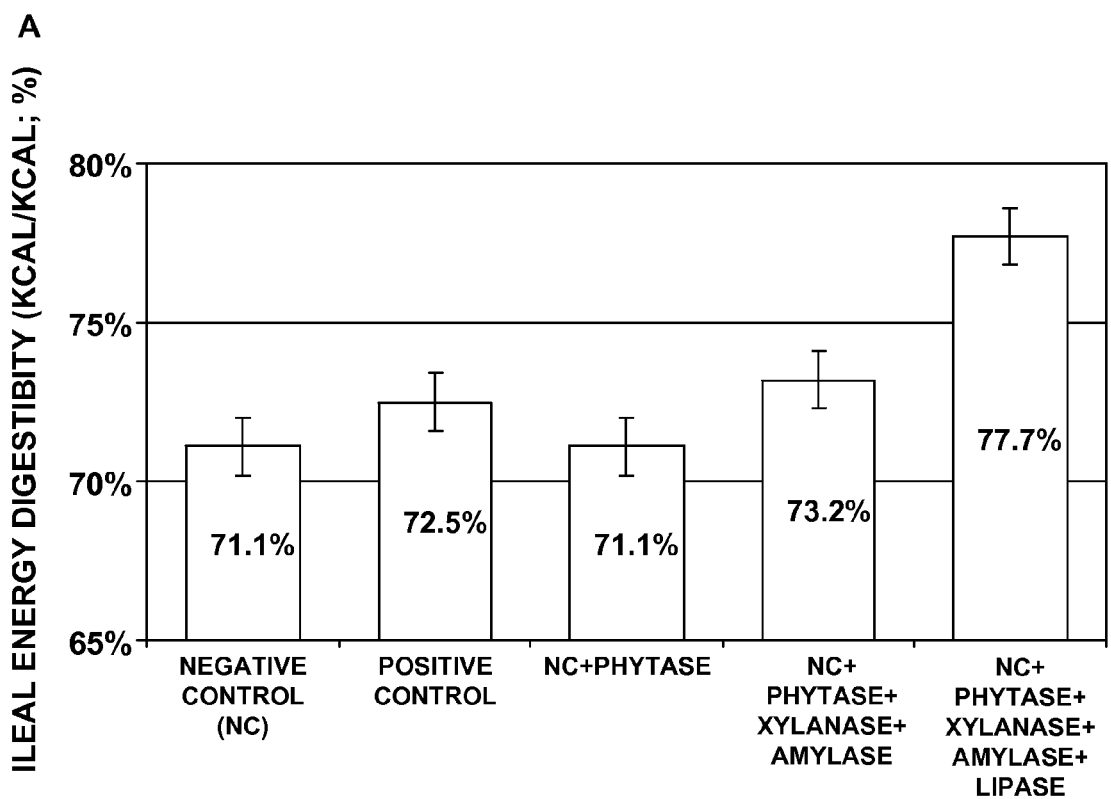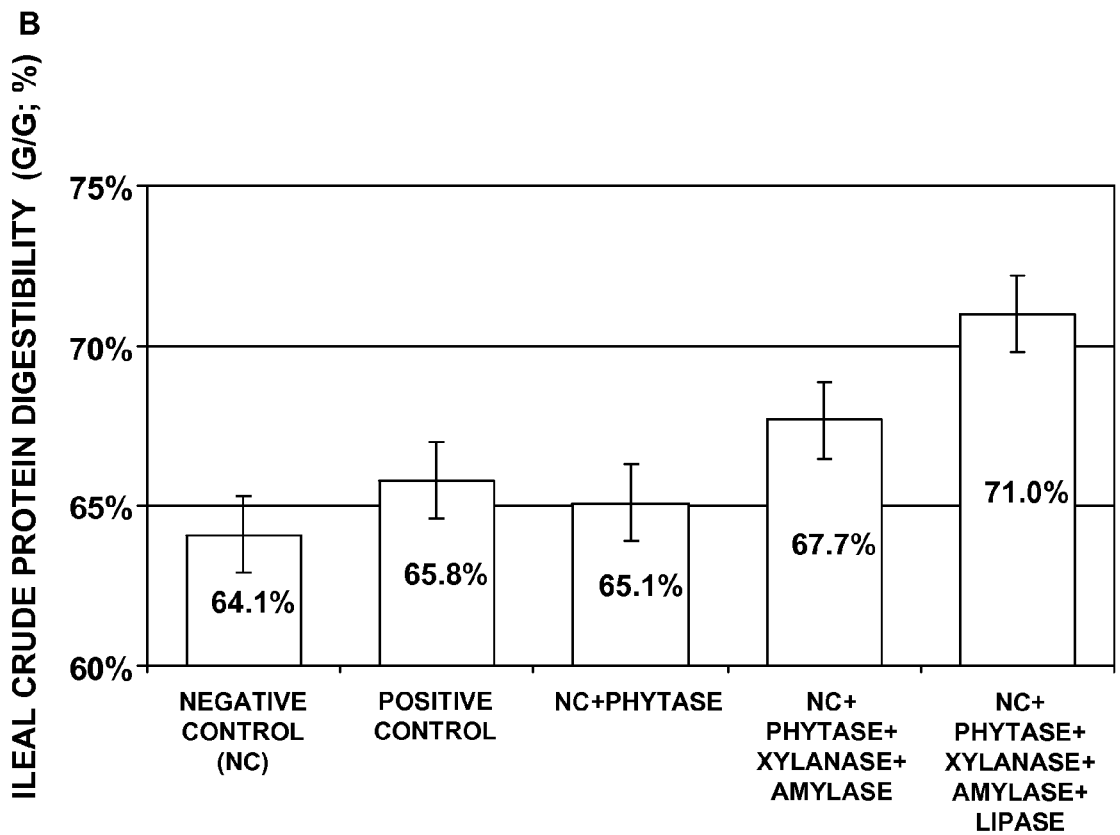
FIG. 23.

SEQ ID NO. 12

1   MKAILIPFLS LLIPLTPQSA FAQSEPELKL ESVVIVSRHG VRAPTKATQL
51  MQDVTPDAWP TWPVKLGWLT PRGGELIAYL GHYQRQRLVA DGLLAKKGCP
101 QSGQVAIIAD VDERTRKTGE AFAAGLAPDC AITVHTQADT SSPDPLFNPL
151 KTGVCQLDNA NVTDAILSRA GGSIADFTGH RQTAFRELER VLNFPQSNLC
201 LKREKQDESC SLTQALPSEL KVSADNVSLT GAVSLASMLT EIFLLQQAQG
251 MPEPGWGRIT DSHQWNTLLS LHNAQFYLLQ RTPEVARSRA TPLLDLIKTA
301 LTPHPPQKQA YGVTLPTSVL FIAGHDTNLA NLGGALELNW TLPGQPDNTP
351 PGGELVFERW RRLSDNSQWI QVSLVFQTLQ QMRDKTPLSL NTPPGEVKLT
401 LAGCEERNAQGMCSLAGFTQIVNEARIPACSL

WILD TYPE *E.COLI* PHYTASE (SIGNAL SEQUENCE IN BOLD)

*FIG. 26.*

SEQ ID NO. 13

1   QSEPELKLES VVIVSRHGVR APTKATQLMQ DVTPDAWPTW PVKLGWLTPR
51  GGELIAYLGH YQRQRLVADG LLAKKGCPQS GQVAIIADVD ERTRKTGEAF
101 AAGLAPDCAI TVHTQADTSS PDPLFNPLKT GVCQLDNANV TDAILSRAGG
151 SIADFTGHRQ TAFRELERVL NFPQSNLCLK REKQDESCSL TQALPSELKV
201 SADNVSLTGA VSLASMLTEI FLLQQAQGMP EPGWGRITDS HQWNTLLSLH
251 NAQFYLLQRT PEVARSRATP LLDLIKTALT PHPPQKQAYG VTLPTSVLFI
301 AGHDTNLANL GGALELNWTL PGQPDNTPPG GELVFERWRR LSDNSQWIQV
351 SLVFQTLQQM RDKTPLSLNT PPGEVKLTLA GCEERNAQGM CSLAGFTQIV
401 NEARIPACSL

MATURE *E.COLI* PHYTASE

*FIG. 27.*

SEQ ID NO. 14

```
                M  W  Y  L  L  W  F  V  G  I  L  L  M  C  S  L  S  T  L  V  L  V  W  L  D  P  R  L  K  S  *
   1 TAAggagcagaaacaATGTGGTATTTACTTTGGTTCGTCGGCATTTTGTTGATGTGTTCGCTCTCCACCCTTGTGTTGTTGGTATGGCTGGACCCGCGTCTGAAAAGTTAAcgaacgtaggcc      120

1 ------ -35 ------ -10                                                                                                              18
 121 tgatgcggcggcattagcatcgcatcggcaatcaataatgtcagatgcgaaacatatgATGAAAGCGATCTTAATCCCATTTTATCTCTTCTGATTCCGTTAACCCGCA                      240
                                                                M  K  A  I  L  I  P  F  L  S  L  L  I  P  L  T  P  Q 19  S  A  F  A  Q  S  E  P  E  L  K  L  E  S  V  V  I  V  S  R  H  G  V  R  A  P  T  K  A  T  Q  L  M  Q  D  V  T  P  D  A         58
 241 ATCTGCATTCGCTCAGAGTGAGCCGGAGCTGAAGCTGGAAAGTGTGGTTATTGTCAGTCGTCATGGTGTGCGTGCTCCAACCAAGGCCACGCAACTGATGCAGGATGTCACCCCAGACGC          360

59  W  P  T  W  P  V  K  L  G  W  L  T  P  R  G  G  E  L  I  A  Y  L  G  H  Y  Q  R  Q  R  L  V  A  D  G  L  L  A  K  K  G         98
 361 ATGGCCAACCTGGCCGGTAAAACTGGGTTGGCTGACACCGCGTGGCGGTGAGCTAATCGCCTATCTCGGACATTACCAACGCCAGCGTCTGGTAGCCGACGGATTGCTGGCGAAAAAGGG          480

99  C  P  Q  S  G  Q  V  A  I  I  A  D  V  D  E  R  T  R  K  T  G  E  A  F  A  A  G  L  A  P  D  C  A  I  T  V  H  T  Q  A        138
 481 CTGTCCGCAGTCTGGTCAGGTCGCGATTATTGCTGATGTCGACGAGCGTACCCGTAAAACAGGCGAAGCCTTCGCCGCCGGGCTGGCACCTGACTGTGCAATAACCGTACATACCCAGGC          600

139  D  T  S  S  P  D  P  L  F  N  P  L  K  T  G  V  C  Q  L  D  N  A  N  V  T  D  A  I  L  S  R  A  G  G  S  I  A  D  F  T        178
 601 AGATACGTCCAGTCCGGATCCGTTATTTAATCCTCTAAAAACTGGCGTTTGCCAACTGGATAACGCCAACGTCACTGACGCGATCCTCAGCAGGGCAGGAGGGTCAATTGCTGACTTTAC          720

179  G  H  R  Q  T  A  F  R  E  L  E  R  V  L  N  F  P  Q  S  N  L  C  L  K  R  E  K  Q  D  E  S  C  S  L  T  Q  A  L  P  S        218
 721 CGGGCATCGGCAAACGGCTTTCGCGAACTGGAACGGGTGCTTAATTTTCCGCAATCAAACTTGTGCCTTAAACGTGAGAAACAGGACGAAAGCTGTTCATTAACGCAGGCATTACCATC          840

219  E  L  K  V  S  A  D  N  V  S  L  T  G  A  V  S  L  A  S  M  L  T  E  I  F  L  L  Q  Q  A  Q  G  M  P  E  P  G  W  G  R        258
 841 GGAACTCAAGGTGAGCGCCGACAATGTCTCATTAACCGGTGCGGTAAGCCTCGCATCAATGCTGACGGAGATATTCTTCCTGCAACAAGCACAGGGAATGCCGGAGCCGGGGTGGGGAAG          960

259  I  T  D  S  H  Q  W  N  T  L  L  S  L  H  N  A  Q  F  Y  L  L  Q  R  T  P  E  V  A  R  S  R  A  T  P  L  L  D  L  I  K        298
 961 GATCACCGATTCACACCAGTGGAACACCCTGCTAAGTTTGCATAACGCGCAATTTTATTTGCTACAACGCACGCCAGAGGTTGCCCGCAGCCGCGCCACCCCGTTATTAGATTTGATCAA        1080

299  T  A  L  T  P  H  P  P  Q  K  Q  A  Y  G  V  T  L  P  T  S  V  L  F  I  A  G  H  D  T  N  L  A  N  L  G  G  A  L  E  L        338
1081 GACAGCGTTGACGCCGCATCCACCGCAAAAACAGGCGTATGGCGTAACTCTCCCGACCAGCGTCCTGTTTATCGCCGGACACGATACTAATCTCGGCGGCACTGGAGCT                    1200

339  N  W  T  L  P  G  Q  P  D  N  T  P  P  G  E  L  V  F  E  R  W  R  R  L  S  D  N  S  Q  W  I  Q  V  S  L  V  F  Q  T        378
1201 CAACTGGACGCTTCCCGGGCAGCCGGATAACACGCCGCCAGGTTGAACTGGTGTTTGAACGCTGGCGTCGGCTAAGCGACAATAACCAGTGGATTCAGGTTTCGCTGGTCTTCCAGAC          1320

379  L  Q  Q  M  R  D  K  T  P  L  S  L  N  T  P  P  G  E  V  K  L  T  L  A  G  C  E  E  R  N  A  Q  G  M  C  S  L  A  G  F        418
1321 TTTACAGCAGATGCGTGATAAAACGCCGCTGTCATTAAATACGCCGCCGGGAGAGGTGAAACTGACCCTGGCAGGATGTGAAGAGCGAAATGCCAGGGCATGTTCGTTGGCAGGTTT          1440

419  T  Q  I  V  N  E  A  R  I  P  A  C  S  L  *                                                                                     433
1441 TACGCAAATCGTGAATGAAGCACGCATACCGGCGTGCAGTTTGTAAtgcataaaaagagcattcagttacctgaggctgaataactgaaggctgaaaaactgtctaatgcgtag                1560

1561 ccggaaaaggcgttcacgccgcatccggcatcggcacttcagttttactctttccggagtaactataacgtaatgtatagcgtaactgtaaggctggccgtttaatcacccat                 1680

1681 tgaggatagcgcctttaatattgacgcctgccttgttcagaccgctgcattgaccaaatccacctctttggccgtgttcaagcaaaacgcaaacagcaggctgtgcaacagaacgcc              1800

1801 ccacgaccgcggcatcactccgcatcggcggcatcgggcgggatcgacaatcacccagatcgacgatcaccagataattccagtaattgaccattcgccattcgatcaatcgccattcagtaattgacgcatccgatcg
                                                                                                   PVU I NUCLEOTIDE SEQUENCE ENCODING E.COLI PHYTASE.
(CODING SEQUENCE SHOWN IN CAPITAL LETTERS AS NUCLEOTIDES 188- 1783. MATURE SEQUENCE BEGINS AT NT 253)
```

FIG. 28.

A
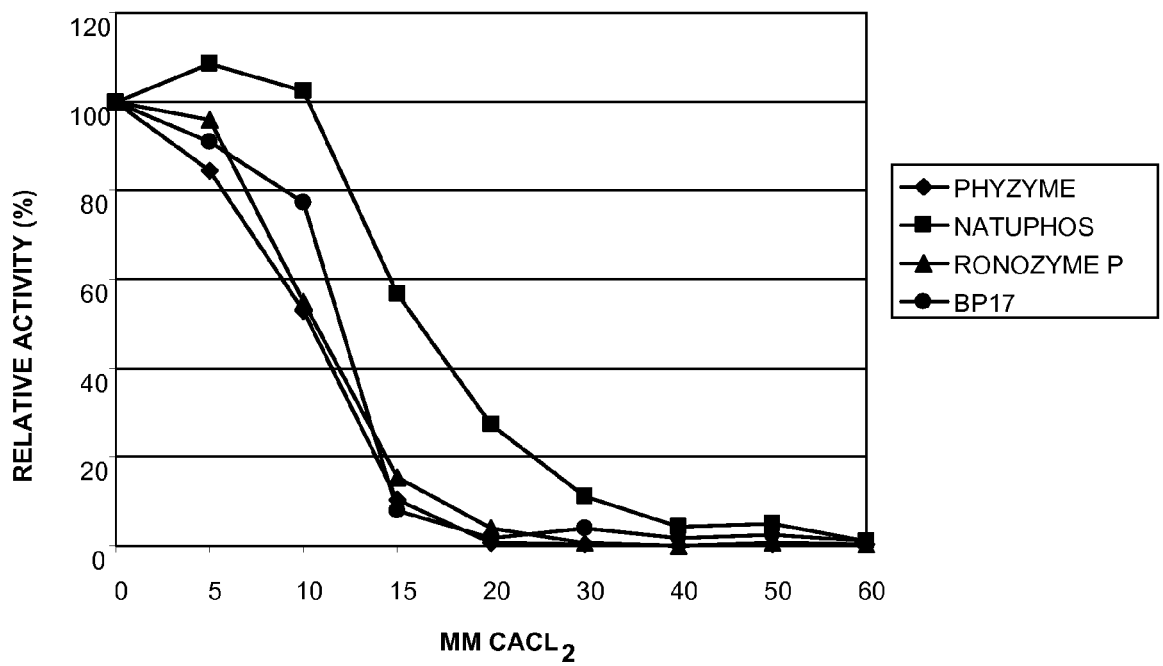
B
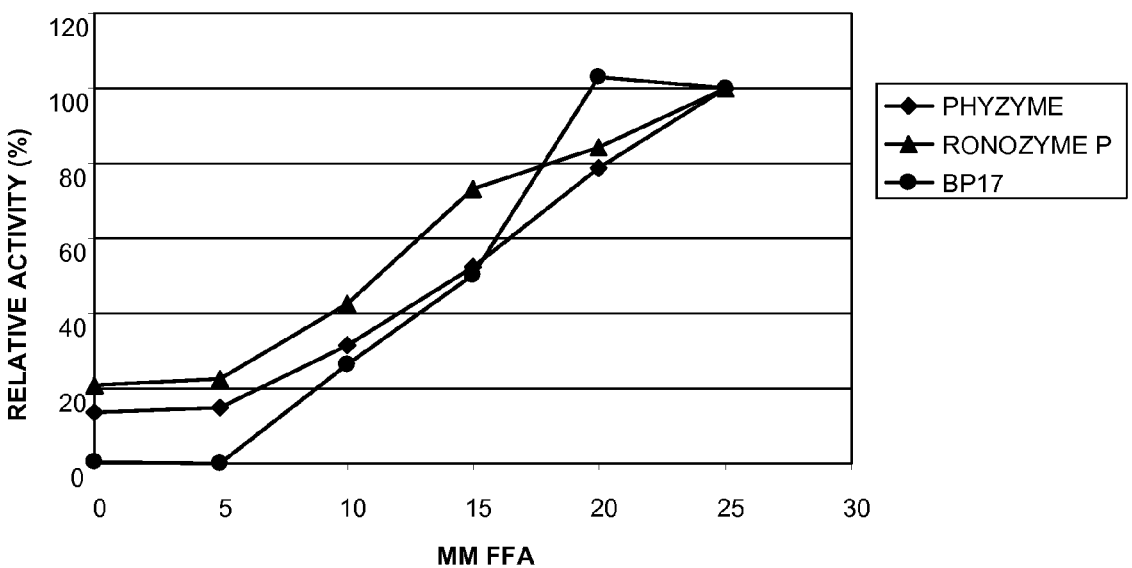
FIG. 30.

FEED SUPPLEMENT

CROSS-REFERNCE TO RELATED APPLICATIONS

This application claims priority to PCT Application No. PCT/IB2010/051804 entitled "Feed Supplement," filed Apr. 23, 2010, which claims priority to U.S. Provisional Application No. 61/172,272, filed Apr. 24, 2009, Great Britain Application No. 0908770.1, filed May 20, 2009, Great Britain Application No. 0922467.6, filed Dec. 23, 2009, and U.S. Provisional Application No. 61/312,413, filed Mar. 10, 2010, all of which are expressly incorporated by reference herein in their entirety.

FIELD OF THE INVENTION

The present invention relates to feed supplements. More specifically, the present invention relates to feed supplements comprising phytases and lipolytic enzymes which can be used for enhancing digestion in animal feedstuffs and to feedstuffs comprising the feed supplements.

SEQUENCE LISTING

A text file in compliance with ASCII and having a ".txt" extension has been electronically submitted via EFS-Web. The text file named "Sequence Listing—Feed Supplement" was created on Oct. 20, 2011, and is 95,302 bytes. The text file is expressly incorporated by reference herein in its entirety.

BACKGROUND

Phytate is the major storage form of phosphorus in cereals and legumes. However, monogastric animals such as pigs, poultry and fish are not able to metabolise or absorb phytate (or phytic acid) and therefore it is excreted, leading to phosphorous pollution in areas of intense livestock production. Moreover, phytic acid also acts as an antinutritional agent in monogastric animals by chelating metal agents such as calcium, copper and zinc.

In order to provide sufficient phosphates for growth and health of these animals, inorganic phosphate is added to their diets. Such addition can be costly and further increases pollution problems.

Through the action of phytase, phytate is generally hydrolysed to give lower inositol-phosphates and inorganic phosphate. Phytases are useful as additives to animal feeds where they improve the availability of organic phosphorus to the animal and decrease phosphate pollution of the environment (Wodzinski R J, Ullah A H. Adv Appl Microbiol. 42, 263-302 (1996)).

The addition of phytase to broiler feed has also been shown to increase the apparent metabolisable energy (AME), the availability of nitrogen and amino acids (Ravindran, V. et al, Brit. Poultry Sci. 41, 193-200 (2000)).

A number of phytases of fungal (Wyss M. et al. Appl. Environ. Microbiol. 65 (2), 367-373 (1999); Berka R. M. et al. Appl. Environ. Microbiol. 64 (11), 4423-4427 (1998); Lassen S. et al. Appl. Environ. Microbiol. 67 (10), 4701-4707 (2001)) and bacterial (Greiner R. et al Arch. Biochem. Biophys. 303 (1), 107-113 (1993); Kerovuo et al. Appl. Environ. Microbiol. 64 (6), 2079-2085 (1998); Kim H. W. et al. Biotechnol. Lett. 25, 1231-1234 (2003); Greiner R. et al. Arch. Biochem. Biophys. 341 (2), 201-206 (1997); Yoon S. J. et al. Enzyme and microbial technol. 18, 449-454 (1996); Zinin N. V. et al. FEMS Microbiol. Lett. 236, 283-290 (2004)) origin have been described in the literature.

However, fungal phytases tend to be proteolytically unstable (Igbasan F. A. et al. Arch. Anim. Nutr. 53, 353-373 (2000)) and therefore susceptible to degradation, while some bacterial phytases have a narrow substrate specificity for phytate alone and poorly degrade inositol phosphates of intermediate degrees of phosphorylation (Greiner R. et al., Arch. Biochem. Biophys. 303 (1), 107-113 (1993); Kerovuo J et al, Biochem. J. 352, 623-628 (2000)).

Furthermore, it is known that the interaction of calcium with phytate to form Ca-phytate complexes is detrimental to phytase activity (Selle, P. H. et al, Livestock Science. 124, 126-141 (2009)). The calcium in these Ca-phytate complexes has been hypothesised to make phytate inaccessible to the phytase or to compete with non-complexed phytate for the active site of the enzyme (Long, C., Phytase, Biochemists Handbook, Princeton, N.Y., Van Nostrand-Reinhold (1961); Wise, A., Nutrition Abstracts & Reviews, 53, 791-806 (1983)).

The addition of phytase has been shown to increase the AME of a high phytate diet. Ravindran et al (Br. Poult. Sci., 2000, 41, 193-200) has suggested that calcium phytate complexes react with fatty acids to form insoluble soaps in the gut lumen, thereby lowering fat digestibility. The addition of phytase has been suggested to reduce the level of these soaps. Supporting this hypothesis, there is evidence of phytate interactions with lipid in corn (Cosgrove, 1966, Rev. Pure App. Chem. 16:209-224). These 'lipophytins' have been described as a complex of Ca/Mg-phytate, lipids and peptides (Cosgrove, 1966, Rev. Pure App. Chem. 16:209-224). Other reports have also suggested interactions between Ca, fat and phytate in the diet. For instance, Matyka et al. (1990) (Anim. Feed. Sci. Technol. 31:223-230) found that dietary tallow reduced phytate P utilization in young chicks, and increased the percentage of fat excreted as soap fatty acids.

The addition of exogenous lipases has had limited success in increasing lipid and mineral digestibility. However, this may have been limited by the formation of complexes of free fatty acids bound with Ca and phytate (Cosgrove, 1966 supra), which are insoluble in the gastro intestinal tract, and poorly absorbed (Matyka et al. 1990 supra).

The use of exogenous lipases in animal feed has been previously suggested with the objective to improve the fat digestion by animals. Lipase is hypothesised to improve digestion as it liberates absorbable free fatty acids (FFA) faster than otherwise would have happened. However, attempts to demonstrate improvements in animal performance or digestibility by the use of exogenous lipases have been at best inconsistent and have often showed lipases not to work. Dierick and Decuypere (2004) (J. Sci. Food Agric. 84:1443-1450) showed no improvements in fat digestibility with addition of a microbial lipase in pig diets. Hurtado et al. (2000) (Rev. Bras. Zootec. 29:794-802) failed to detect increments of body weight gain, feed efficiency and energy digestibility due to the use of an exogenous lipase in piglets. Additionally, they reported no additive effects in any of these parameters when such lipase was combined with an amylase and a protease. Officer (1995) (Anim. Feed Sci. Technol. 56:55-65) reported no significant changes in body weight gain of feed intake of piglets by the use of two combinations of exogenous enzymes which they described as lipase, proteinase, B-glucanase, amylase and cellulose, and lipase, B-glucanase, hemi-cellulase, pentosanase, cellulose, amylase and proteinase.

In broiler chickens, Meng et al. (2004) (Poult. Sci. 83:1718-1727), when using a bacterial lipase in wheat-based diets, failed to detect any effect of the lipase on apparent digestibility of fat, starch, nitrogen and NSP, as well as AME. Additionally, they rejected the hypothesis that a combination of carbohydrases, including xylanase, glucanase and cellulase, on top of the lipase would increase the lipase effects on nutrient digestibility by reducing viscosity of the digesta and increasing fat digestion and absorption.

Al-Marzooqi and Leeson (1999) tested lipases from animal origin and pancreatic extracts. Although they were able to demonstrate improvements in fat digestibility and reductions on the level of soaps at the faecal levels when these additives were used in the diet, they also reported an anorexic effect (reduction of feed intake), which they explained by possible contaminations with cholecystokinin in this type of extracts. This fact limits its utilization in animal feed and possible improvements in growth or feed efficiency in animals.

One aim of the present invention is to provide a feed supplement which provides improved availability of at least one nutrient or an improvement in the apparent metabolisable energy from a feed material.

SUMMARY

The present invention is based on the surprising discovery that the addition of a feed supplement comprising at least one specific lipolytic enzyme and at least one specific phytase to a feedstuff results in improved uptake of at least one nutrient and or mineral compared to the use of the enzymes individually.

According to the broadest aspect of the present invention there is provided a feed supplement comprising:—
  i. at least one lipolytic enzyme; and
  ii. at least one phytase.

The inventors have surprisingly discovered that contrary to previous reports (Mulyantini, N. G. A. et al Aust. Poult. Sci. Symp, 17, 305-307 (2005)), the addition of a feed supplement comprising at least one specific phytase and at least one specific lipolytic enzyme to feed material to produce a feedstuff results in an increase in the availability of at least one nutrient and/or an increase in the apparent metabolisable energy (AME).

Although not wishing to be bound by theory, the inventors have hypothesised that this surprising discovery may be due to the action of the lipolytic enzyme liberating free fatty acids (FFA) at an earlier stage in digestion where the pH is acidic. These FFA may bind with excess calcium to form soaps in the gut. There is then less free calcium available to bind to phytate, thereby boosting phytase activity in the regions of the gastrointestinal tract (GIT) where phytic acid and calcium tends to form a phytase resistant complex. This leads to increased phosphate liberation and absorption. The free fatty acid calcium complexes dissolve later in the GIT resulting in increased fat and calcium absorption and/or increased AME.

According to another aspect of the present invention there is provided a method of making a feed supplement comprising mixing at least one lipolytic enzyme and at least one phytase.

According to another aspect of the present invention there is provided a feedstuff comprising a feed material and the feed supplement or at least one lipolytic enzyme and at least one phytase according to the present invention.

According to a further aspect of the present invention, there is provided a method of making a feedstuff comprising adding to a feed material a feed supplement or at least one lipolytic enzyme and at least one phytase according to the present invention.

According to a further aspect of the present invention there is provided a method for increasing the availability of at least one dietary nutrient and/or increasing the apparent metabolisable energy (AME) from a feed material comprising adding to feed material a feed supplement comprising a combination of at least one lipolytic enzyme and at least one phytase or adding to the feed material at least one lipolytic enzyme and at least one phytase.

According to a further aspect of the present invention there is provided a method of increasing the growth rate of an animal comprising feeding the animal an effective amount of a feedstuff according to the present invention.

According to a further aspect of the present invention there is provided the use of at least one phytase and at least one lipase in the manufacture of a feedstuff for increasing the availability of at least one nutrient and/or increasing the available metabolic energy from a feed material.

It will be understood that any of the preferred features disclosed herein is considered to be equally applicable to any of the aspects described above unless explicitly stated otherwise. Any preferred feature is also considered to be disclosed in combination with any other preferred feature disclosed herein.

To be efficient as an enzyme additive to animal feed, a phytase has to combine a number of different properties. In order to be able to degrade phytic acid in the acidic environment of an animal's stomach it has to be active at low pH, preferably over a broad range of pH values. In addition, it has to have high specific activity and preferably high thermostability to enable the protein to withstand high temperatures commonly used in preparation of feedstuffs such as feed pellets.

It is also important that the enzyme has broad substrate specificity allowing it to hydrolyse not only phytate but also intermediate products of phytate degradation such as inositol pentaphosphates, tetraphosphates and triphosphates. Studies on phytate degradation in pigs show that these inositol oligophosphates otherwise remain largely insoluble in the small and large intestine and thus inaccessible to alkaline phosphatases produced by the animal and gut microflora (Schlemmer U. et al. Arch. Anim. Nutr. 55, 255-280 (2001)). Variations in substrate specificity profiles of different enzymes have been identified. For example, inositol-triphosphates generated by the phytase from *B. subtilis* are essentially resistant to further hydrolysis by this enzyme [Kerovuo J. et al. Biochem J. 352, 623-628 (2000)].

In preferred embodiments, the phytase is preferably *E. coli* phytase marketed under the name Phyzyme XP™ by Danisco A/S. Alternatively the phytase may be a *Buttiauxella* phytase, for example, the phytase enzymes taught in WO 2006/043178, WO 2008/097619, WO2008/092901 and PCT/US2009/41011 all of which are incorporated herein by reference.

In a most preferred embodiment, the phytase comprises an *E. coli* phytase and/or a *Buttiauxella* sp. phytase. More preferably, the phytase comprises a polypeptide comprising the amino acid sequence as shown in any one of SEQ ID NOs: 1-6 or SEQ ID NO: 13; or a polypeptide comprising one or several amino acid additions, deletions and/or substitutions compared to any one of SEQ ID NOs: 1-6 or SEQ ID NO: 13; or a polypeptide having at least 70%, 80%, 90%, 95%, 98% or 99% identity to any one of SEQ ID NOs: 1-6 or SEQ ID NO: 13; or a polypeptide produced by expression of a nucleotide sequence comprising the sequence of SEQ ID NO: 11; or nucleotides 253 to 1483 of SEQ ID NO:14 or a sequence which differs from SEQ ID NO: 11 or nucleotides 253 to 1483 of SEQ ID NO:14 due to the degeneracy of the genetic code;

or a sequence comprising one or several nucleotide additions, deletions and/or substitutions compared to the sequence of SEQ ID NO: 11; or nucleotides 253 to 1483 of SEQ ID NO:14; or a sequence which has at least 70%, 80%, 90%, 95%, 98% or 99% identity to SEQ ID NO: 11 or nucleotides 253 to 1483 of SEQ ID NO:14.

In one preferred embodiment, the phytase has phytase activity at least at a pH in the range of about pH 2.5 to about pH 5.5. More preferably, the phytase has phytase activity at least at a pH in the range of about pH 2.5 to about pH 3.5 and also in the range of about pH 5 to about pH 5.5 when measured by the phytase assay disclosed in the materials and methods section below.

Preferably, the phytase has a specific activity level of at least 100 FTU/mg of enzyme. More preferably, at least, 200, 300, 400, 500, 700, 1000 FTU/mg.

It will be understood that as used herein 1 FTU (phytase unit) is defined as the amount of enzyme required to release 1 µmol of inorganic orthophosphate from a substrate in one minute under the reaction conditions defined herein in the phytase assay at pH 5.5 described in the materials and methods section.

In preferred embodiments, the phytase for use in the present invention has a pH optimum in the range of pH 2 to 5.5, preferably 4.0-4.5, retaining at least 50% of the maximum activity over the pH range 2.0-5.5 and/or having a specific activity over 300 FTU/mg.

Preferably, the lipolytic enzyme for use in the present invention has lipase activity at a pH in the range of about pH 1.5 to about pH 5.5 when measured by the lipase assay described in the materials and methods section below. More preferably, the lipolytic enzyme has lipase activity at a pH in the range of about pH 1.5 to about pH 3.5, or about pH 2.0 to about pH 3.5.

It will be understood that the lipolytic enzyme for use in the present invention may be any suitable lipolytic enzyme which, using the assay defined herein, shows lipolytic enzyme activity. Preferably, the lipolytic enzyme has an activity level of at least 100 LIPU/mg of enzyme. More preferably, at least, 200, 300, 400, 500, 700, 1000 LIPU/mg.

As used herein, 1 LIPU (lipase unit) is defined as the amount of enzyme which releases 1 µmol of $H^+$ per minute under the conditions described in the lipase assay described in the materials and methods section herein below.

In one preferred embodiment, the lipolytic enzyme for use in the present invention is derived from the filamentous fungus *Aspergillus tubingensis* as described in WO 98/45453.

Preferably, the lipolytic enzyme comprises; a polypeptide comprising the amino acid sequence as shown in SEQ ID NO: 7 or 8; or a polypeptide comprising one or several amino acid additions, deletions and/or substitutions compared to SEQ ID NO: 7 or 8; or a polypeptide having at least 70%, 80%, 90%, 95%, 98% or 99% identity thereto; or a polypeptide which is produced by expression of a nucleotide sequence comprising the sequence of SEQ ID NO: 9 or 10; or a sequence which differs from SEQ ID NO:9 or 10 due to the degeneracy of the genetic code; or a sequence comprising one or several nucleotide additions, deletions and/or substitutions compared to the sequence of SEQ ID NO: 9 or 10 or a sequence which has at least 70%, 80%, 90%, 95%, 98% or 99% identity to SEQ ID NO: 9 or 10.

Alternatively, the lipase may be selected from the group consisting of Acidic lipase from *Pseudomonas gessardii* (Ramani, K. et al, J Ind Microbiol Biotechnol (2010) 37:531-535), Acidic lipase from *Rhizopus arrhizus* (Kumar, K K. et al, Hindustan Antibiot Bull. 1993 February-May; 35(1-2):33-42) (SEQ ID NO: 32, 33), Acidic lipase from *Penicillium simplicissimum* (Gutarra M. L. E. et al, Bioresource Technology 100 (2009) 5249-5254), Acidic lipase from *Aspergillus niger* NCIM 1207 (Mhetras N. C. et al, Bioresource Technology 100 (2009) 1486-1490, Pel, H. J., et al, Nat. Biotechnol. 25 (2), 221-231 (2007)) (SEQ ID NO: 27), Mammalian gastric lipases from, for example, human (SEQ ID NO: 17, 18), bovine (SEQ ID NO: 19, 20), mouse (SEQ ID NO: 21, 22), rat (SEQ ID NO: 23, 24) and canines (SEQ ID NO: 25, 26) (Chahinian, H. et al, Biochemistry 2006, 45, 993-1001), Acid lipase from Castor beans (Eastmond, P. J. The Journal of Biological Chemistry, 279 (2004); 45540-45545) (SEQ ID NO: 28, 29), and LIP2 lipase from *Yarrowia lipolytica* (Aloulou, A. et al, Biochimica et Biophysica Acta 1771 (2007) 228-237) (SEQ ID NO: 30, 31).

As indicated above, the inventors have discovered that the improvement in performance of the feed supplement of the present invention is due to the action of the lipolytic enzyme liberating free fatty acids (FFA) at an earlier stage in digestion. This results in the formation of calcium soaps and the associated reduction in calcium-phytate complexes.

In a further preferred embodiment, the lipolytic enzyme for use in the present invention is produced in a *Trichoderma reesei* cell, for example by expression of a nucleotide having the sequence of SEQ ID NO: 9 or SEQ ID NO:10 in a *T. reesei* host cell.

In a further preferred embodiment, the feed supplement according to the present invention comprises:
i) a lipolytic enzyme which is a lipolytic enzyme characterised by at least one of the following characteristics:
  a) a lipolytic enzyme that has lipase activity at a pH in the range of about pH 1.5 to about pH 3.5 when measured by the lipase assay disclosed herein;
  b) a lipolytic enzyme which comprises a polypeptide comprising the amino acid sequence as shown in SEQ ID NO: 7 or 8 or a polypeptide having at least 70%, 80%, 90%, 95%, 98% or 99% identity thereto;
  c) a lipolytic enzyme which is produced by expression of a nucleotide sequence comprising the sequence of SEQ ID NO: 9 or 10; or a sequence which differs from SEQ ID NO:9 or 10 due to the degeneracy of the genetic code; or a sequence which has at least 70%, 80%, 90%, 95%, 98% or 99% identity to SEQ ID NO: 9 or 10; and
ii) a phytase which characterised by at least one of the following characteristics:—
  d) a bacterial phytase;
  e) a phytase that has phytase activity when measured by the phytase assay described herein below at a pH in the range of about pH 2.5 to about pH 3.5;
  f) a phytase which comprises a polypeptide comprising the amino acid sequence as shown in any one of SEQ ID NOs: 1-6 or SEQ ID NO:13 or a polypeptide having at least 70%, 80%, 90%, 95%, 98% or 99% identity thereto;
  g) a phytase which is produced by expression of a nucleotide sequence comprising the sequence of SEQ ID NO: 11 or nucleotides 253 to 1483 of SEQ ID NO:14; or a sequence which differs from SEQ ID NO: 11 or nucleotides 253 to 1483 of SEQ ID NO:14 due to the degeneracy of the genetic code; or a sequence which has at least 70%, 80%, 90%, 95%, 98% or 99% identity to SEQ ID NO: 11 or nucleotides 253 to 1483 of SEQ ID NO:14.

In a further preferred embodiment, the feed supplement comprises lipolytic enzyme and phytase having a ratio of lipase activity (measured as lipase units (LIPU)) to phytase activity (measured as phytase units (FTU)) in the range of about 1:5 to about 12:1, preferably, in a ratio of about 1:3 to about 3:1 and more preferably in a ratio of about 1:1 to about 3:1 as defined by the lipase and phytase assays at pH5.5 as described herein below.

Preferably, the at least one dietary nutrient whose availability is increased is selected from the group comprising; phosphorous; calcium; amino acids, fat and/or starch. Preferably, the availability is improved both at the ileal and/or the total gastrointestinal tract.

It will be understood by the skilled person that the lipolytic enzyme and the phytase for use in the present invention can be provided independently as either liquid or as solid/granulated compositions.

Preferably, when said enzyme is in liquid form, said enzyme is in the medium into which the enzyme has been secreted following culturing of a cell comprising said enzyme. Preferably said medium is cell-free (i.e. the cell(s) have been separated from the medium). Preferably said medium is concentrated. It will be understood that the medium can be granulated to provide a solid enzyme composition.

It will be further understood that the feed supplement or at least one lipolytic enzyme and at least one phytase according to the present invention may be provided in the form of a solution or as a solid—depending on the use and/or the mode of application and/or the mode of administration.

In one embodiment the feed supplement or at least one lipolytic enzyme and at least one phytase according to the present invention is in a liquid formulation suitable for consumption, preferably such liquid composition contains either buffer, salts, sorbitol and/or glycerol.

In an alternative embodiment, feed supplement or at least one lipolytic enzyme and at least one phytase according to the present invention can be provided as one or more cells comprising said lipolytic enzyme and/or phytase.

In one embodiment the feed supplement is granulated or co-granulated with other enzymes.

Preferably, the feed supplement further comprises at least one physiologically acceptable carrier.

The physiologically acceptable carrier is preferably selected from at least one of maltodextrin, limestone (calcium carbonate), cyclodextrin, wheat or a wheat component, sucrose, starch, anti-foam, $Na_2SO_4$, Talc, PVA and mixtures thereof.

In one embodiment the phytase and/or lipolytic enzyme is dried on the physiologically acceptable carrier.

In preferred embodiments, the feed supplement may comprise at least one further enzyme. In preferred embodiments, the at least one further feed enzyme is selected from the group consisting of those involved in starch metabolism, fibre degradation, lipid metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, -galactosidases, -glucanases, glucan lysases, endo-glucanases, glucoamylases, glucose oxidases, -glucosidases, including β glucosidase, glucuronidases, hemicellulases, hexose oxidases, hydrolases, invertases, isomerases, laccases, lyases, mannosidases, oxidases, oxidoreductases, pectate lyases, pectin acetyl esterases, pectin depolymerases, pectin methyl esterases, pectinolytic enzymes, peroxidases, phenoloxidases, polygalacturonases, proteases, rhamno-galacturonases, ribonucleases, thaumatin, transferases, transport proteins, transglutaminases, xylanases, hexose oxidase (D-hexose: $O_2$-oxidoreductase, EC 1.1.3.5) β-glucanase, α-amylase, pectinase, cellobiohydrolase, acid phosphatases and/or others or combinations thereof. These include enzymes that, for example, modulate the viscosity of the feed.

In a more preferred embodiment the feed supplement comprises a phytase, a lipolytic enzyme, a xylanse and/or an amylase. In a most preferred embodiment, the feed supplement comprises phytase, a lipolytic enzyme, a xylanse and an amylase.

Preferably, the amylase is present in the range of 10 U/kg to 10000 U/kg feed, more preferably, 100 U/kg to 7500 U/kg, and even more preferably, 500 U/kg to 5000 U/kg. It will be understood that one amylase U is the amount of enzyme that releases 1 mmol of glucosidic linkages from a water insoluble cross-linked starch polymer substrate per min at pH 6.5 and 37° C.

Preferably, the xylanse is present in the range of 100 U/kg to 10000 U/kg feed, more preferably, 250 U/kg to 7500 U/kg, and even more preferably, 500 U/kg to 5000 U/kg. It will be understood that one xylanse U is the amount of enzyme that releases 0.5 µmol of reducing sugar equivalents (as xylose by the DNS [4]) reducing sugar method) from a oat-spelt-xylan substrate per min at pH 5.3 and 50° C. (Bailey, M. J. Biely, P. and Poutanen, K., Journal of Biotechnology, Volume 23, (3), May 1992, 257-270).

It will be understood that the feed supplement may be for any suitable animal. Preferably, the animal is a monogastric animal, for example poultry or swine.

It will be apparent that the feed supplement may contain the at least one phytase and the at least one lipolytic enzyme in any suitable amount. Preferably, the feed supplement comprises at least 0.1% by weight of lipolytic enzyme and phytase either individually or as a combined percentage. More preferably, the feed supplement may comprise at least 0.5%; at least 1%; at least 2%; at least 3%; or at least 4, 5, 6, 7, 8, 9 or 10% by weight of lipolytic enzyme and phytase either individually or as a combined percentage It will be obvious to the skilled person that the feed supplement or at least one lipolytic enzyme and at least one phytase according to the present invention may also comprise other components such as stabilising agents and/or bulking agents and/or other enzymes.

Preferably, the feed supplement or at least one lipolytic enzyme and at least one phytase according to the present invention will be thermally stable to heat treatment up to about 70° C.; up to about 85° C.; or up to about 95° C. The heat treatment may be performed for up to about 1 minute; up to about 5 minutes; up to about 10 minutes; up to about 30 minutes; up to about 60 minutes. The term thermally stable means that at least about 75% of the enzyme components that were present/active in the additive before heating to the specified temperature are still present/active after it cools to room temperature. Preferably, at least about 80% of the enzyme components that were present and active in the additive before heating to the specified temperature are still present and active after it cools to room temperature.

The feed supplement or at least one lipolytic enzyme and at least one phytase according to the present invention may have a shelf-life of greater than about 30 weeks; greater than about 40 weeks; greater than about 50 weeks; greater than about 1 year; greater than about 1.5 years. The shelf-life means that at least about 80% of the enzyme components that were present and active in the additive when it was prepared are still present and active.

Preferably, the method of preparing a feed supplement according to the present invention comprises a mixing step that comprises admixing the at least one phytase and at least one lipolytic enzyme optionally with at least one physiologically acceptable carrier.

In a particularly preferred embodiment the feed supplement is homogenized to produce a powder.

In an alternative preferred embodiment, the feed supplement is formulated in to granules as described in WO2007/044968 (referred to as TPT granules).

In another preferred embodiments when the feed supplement is formulated into granules the granules comprises a hydrated barrier salt coated over the protein core. The advantage of such salt coating is improved thermo-tolerance, improved storage stability and protection against other feed additives otherwise having adverse effect on the enzyme.

Preferably, the salt used for the salt coating has a water activity greater than 0.25 or constant humidity greater than 60% at 20° C.

Preferably, the salt coating comprises a $Na_2SO_4$.

The method of preparing a feed supplement may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour.

It will be understood that the feed supplement of the present invention is suitable for addition to any appropriate feed material.

As used herein, the term feed material refers to the basic feed material to be consumed by an animal. It will be further understood that this may comprise, for example, at least one or more unprocessed grains, and/or processed plant and/or animal material such as soybean meal or bone meal.

In some embodiments, the feed material will comprise one or more of the following components: a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

It will further be apparent that the feed supplement of the present invention is particularly advantageous when added to a high phytate feed material.

As used herein, the term feedstuff refers to a feed material to which one or more feed supplements have been added.

It will be understood by the skilled person that different animals require different feedstuffs, and even the same animal may require different feedstuffs, depending upon the purpose for which the animal is reared. It will be further understood that depending on the starting feed material, the feedstuff may be a high fibre feedstuff or a low fibre feedstuff.

Preferably, the feedstuff may comprise feed materials comprising maize or corn, wheat, barley, triticale, rye, rice, tapioca, sorghum, and/or any of the by-products, as well as protein rich components like soybean mean, rape seed meal, canola meal, cotton seed meal, sunflower seed mean, animal-by-product meals and mixtures thereof. More preferably, the feedstuff may comprise animal fats and/or vegetable oils.

Optionally, the feedstuff may also contain additional minerals such as, for example, calcium and/or additional vitamins.

It will be apparent to the skilled person that the feed supplement of the present invention will be particularly beneficial when used in a feedstuff comprising high calcium. More particularly a feedstuff comprising high calcium and high phytate.

It will be apparent to a skilled person that the level of calcium which represents a high calcium diet may vary depending on the type of animal and even the use for which the animal is reared. For example, for laying hens, a diet with >3% would be high Ca diet. For broilers and all turkeys, a diet with >1% Ca would be high Ca diet. For the purposes of the present invention, a high calcium diet is considered to be a diet comprising at least 1-2% calcium.

It will further be apparent to a skilled person that a high phytate diet is one which comprises >0.90% weight of phytic acid.

As defined herein, a low fibre feedstuff is a feedstuff comprising one or more feed materials, which contains a maximum content of water insoluble cell walls of about 25%, and/or a maximum content of soluble non-starch polysaccharides of about 4%. More preferably, a maximum content of water insoluble cell walls of about 22.5%, about 20%, about 17.5%, about 15%, about 12.5%; and/or a maximum content of soluble non-starch polysaccharides of about 3%, about 2.5%, about 2%, about 1.75%, about 1.5%, about 1.25%.

In preferred embodiments, the feed supplement or at least one lipolytic enzyme and at least one phytase according to the present invention is mixed with at least one low fibre feed material, for example, corn, wheat, an animal-by product meal, or soybean and/or any of the by-products to provide a low fibre feedstuff.

Preferably, the feedstuff is a corn soybean meal mix.

Preferably, the feed material is not defatted rice bran.

In preferred embodiments, the feedstuff comprises phytase at a level of about 250 FTU/kg to about 15,000 FTU/kg feedstuff (e.g. 250 to 10,000 FTU/kg, 400-7,500 FTU/kg and also 500-5000 FTU/kg).

In further preferred embodiments, the feedstuff comprises lipolytic enzyme at a level of about 125 LIPU/kg to about 45,000 LIPU/kg feedstuff (e.g. 500 to 30,000 LIPU/kg, 1000-20000 LIPU/kg and also 3000-10000 LIPU/kg).

It will be readily apparent to the skilled person that in order for the feed supplement of the present invention to provide the claimed advantages phytate must be present in the feed material or feedstuff. It will also be readily apparent that this phytate may be present naturally as a constituent of the feed material, or may be added as an additional supplement at a desired level.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), swine (all age categories), a pet (for example dogs, cats) or fish.

Optionally the feedstuff may comprise further additives. For example, calcium may be added to the feedstuff in any suitable amount to supplement the diet of the animal and/or as a bulking agent. The calcium may be in the form of organic (e.g. leafy green vegetables) or inorganic (e.g. limestone/calcium carbonate) calcium. Preferably, after addition of the calcium supplement, the feedstuff will comprise at least about 0.5% calcium. More preferably, at least about 0.8%, at least about 1.0%, at least about 2.0%, at least about 3% calcium.

The feedstuff may comprise at least 0.0001% by weight of the feed supplement. Suitably, the feedstuff may comprise at least 0.0005%; at least 0.0010%; at least 0.0020%; at least 0.0025%; at least 0.0050%; at least 0.0100%; at least 0.020%; at least 0.100% at least 0.200%; at least 0.250%; at least 0.500% by weight of the feed supplement.

In a further aspect there is provided the use of at least one phytase and at least one lipolytic enzyme in the manufacture of a feedstuff for increasing the availability of at least one nutrient and/or increasing the available metabolic energy from a feed material.

Preferably, the at least one phytase and at least one lipolytic enzyme are formulated as a feed supplement. More preferably, the feed supplement is the feed supplement according to the present invention.

In preferred embodiments the at least one nutrient is selected from phosphorous; calcium; total fat; and/or amino acids.

As used herein, the term "increasing the availability of at least one nutrient and/or increasing the available metabolic energy" means an increase in the amount of the nutrient or energy available for use by the animal consuming a unit weight the feedstuff compared to the availability of the nutrient or energy available from a unit weight of the feed material to which no phytase and lipolytic enzyme or feed supplement has been added.

In a further preferred embodiment, the feed material is a feed material comprising high levels of phytate and/or calcium.

BRIEF DESCRIPTION OF THE FIGURES

The present invention is further illustrated by reference to the accompanying figures in which:

FIG. 1 shows the amino acid sequence (SEQ ID No. 1) of wild type *Buttiauxella* phytase.

FIG. 2 shows the amino acid sequence (SEQ ID No. 2) of a variant *Buttiauxella* phytase designated BP-112.

FIG. 3 shows an amino acid alignment of wild type *Buttiauxella* phytase and 4 variant *Buttiauxella* phytases (SEQ ID Nos. 1-5).

FIG. 4 shows the amino acid sequence (SEQ ID No. 6) of a further variant *Buttiauxella* phytase designated BP-11.

FIG. 5 shows the amino acid sequence (SEQ ID No. 7) of a lipolytic enzyme from *Aspergillus tubingensis* wherein the endogenous signal peptide is shown in bold.

FIG. 6 shows the amino acid sequence (SEQ ID No. 8) of a lipolytic enzyme from *Aspergillus tubingensis* which is the same as SEQ ID No. 7 except that the endogenous signal peptide has been removed.

FIG. 7 shows the nucleotide sequence encoding an *Aspergillus tubingensis* lipolytic enzyme (as shown in SEQ ID No. 7) including the signal sequence—the nucleotide sequence is a genomic DNA sequence (and has been designated as SEQ ID No. 9) The signal sequence is shown in bold and the introns are shown in lower case.

FIG. 8 shows the nucleotide sequence encoding an *Aspergillus tubingensis* lipolytic enzyme (as shown in SEQ ID No. 8) not including the signal sequence—the nucleotide sequence is a genomic DNA sequence (and has been designated as SEQ ID No. 10). The introns are shown in lower case.

FIGS. 14-17 show the activity of the phytases for use in the present invention and controls against phytate at various pH's.

FIG. 22 shows the nucleotide sequence (SEQ ID No: 11) encoding wild type *Buttiauxella* phytase.

FIG. 23A shows Ileal energy digestibility coefficients of cannulated pigs (SEM=0.0009). Bars with different letters differ at a P<0.05 level.

FIG. 23B shows Ileal crude protein digestibility coefficients of cannulated pigs (SEM=0.0009). Bars with different letters differ at a P<0.05 level.

FIG. 26 shows the amino acid sequence of wild type *E. coli* phytase including the signal sequence (SEQ ID NO: 12).

FIG. 27 shows the amino acid sequence of mature wild type *E. coli* phytase (SEQ ID NO: 13).

FIG. 28 shows the nucleotide sequence encoding the wild type *E. coli* phytase (SEQ ID NO:14).

FIG. 30 shows the production of a phytase resistant complex of phytic acid and calcium and reversal by adding free fatty acids. FIG. 30A shows the effect on phytase activity of increasing CaCl2 concentration. FIG. 30B shows the effect on the phytase activity of adding free fatty acids to the reaction mixture containing 15 mM.

FIG. 31A shows the effect on phytase activity of increasing CaCl2 concentration and FIG. 31B shows the effect on the phytase activity of adding Lipase reaction mixture to the phytase reaction mixture containing 30 mM CaCl2.

DETAILED DESCRIPTION

Figure 9:
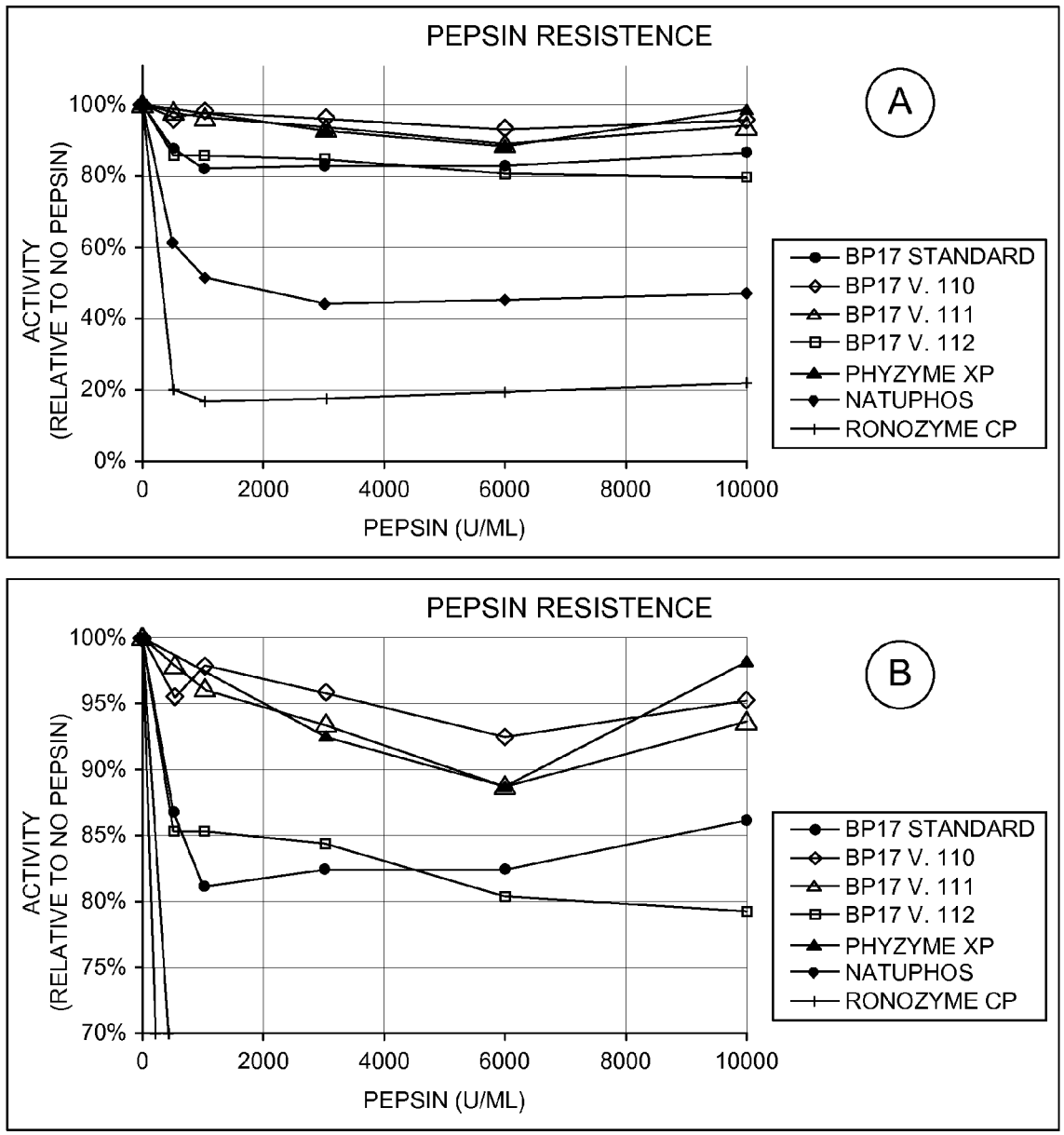
FIG. 9 shows the resistance of the phytases originating from *Buttiauxella*, variants BP-17, BP-110, BP-111, and BP-112, and of Phyzyme XP, Natuphos, and Ronozyme P against increasing concentrations of pepsin.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

As used herein, the term "homologue" means an entity having a certain homology with the amino acid sequences and the nucleotide sequences. Here, the term "homology" can be equated with "identity". Suitably, "homologous" in this context refers to the percentage of sequence identity between two enzymes after aligning their sequences using alignment algorithms as described in more detail below.

In the present context, a homologous amino acid sequence is taken to include an amino acid sequence which may be at least 75, 80, 81, 85 or 90% identical, preferably at least 95, 96, 97, 98 or 99% identical to the sequence. Typically, the homologues will comprise the same active sites etc.—e.g. as the subject amino acid sequence. Although homology can also be considered in terms of similarity (i.e. amino acid residues having similar chemical properties/functions), in the context of the present invention it is preferred to express homology in terms of sequence identity.

By "functional fragment" is meant a fragment of the polypeptide that retains that characteristic properties of that polypeptide. In the context of the present invention, a functional fragment of a phytase enzyme is a fragment that retains the phosphate releasing from phytic acid capability of the whole protein.

For amino acid sequences and nucleotide sequences, homology comparisons can be conducted by eye, or more usually, with the aid of readily available sequence comparison programs. These commercially available computer programs can calculate % homology between two or more sequences.

Percent homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percent homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 Short Protocols in Molecular Biology, 4th Ed—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60).

However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final percent homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASISTM (Hitachi Software), based on an algorithm, analogous to CLUSTAL (Higgins D G & Sharp P M (1988), Gene 73(1), 237-244).

Once the software has produced an optimal alignment, it is possible to calculate percent homology, preferably percent sequence identity. The software typically does this as part of the sequence comparison and generates a numerical result.

In a preferable aspect of the present invention the following software and settings for calculating percentage sequence homology/identity are used. For amino acid sequences percentage of identities (homology) or "positives" are calculated by the AlignX Vector NTI (Vector NTI Advance 9.1 from Invitrogen Corporation, Carlsbad, Calif., USA.) for each possible pair of amino acid sequences. Settings are default parameters (Gap opening penalty—10, Gap extension penalty 0.1).

For nucleic acid sequences percentage of identities (homology) or "positives" are calculated by the AlignX Vector NTI programme from Informax Inc. (USA) for each possible pair of nucleic acid sequences. Settings are default settings for DNA are: Gap opening penalty: 15 and Gap extension penalty: 6.66. (same settings for multiple alignments).

Preferably the amino acid identity (homology) is calculated across the full-length amino acid sequence or for nucleic acid to a corresponding polynucleotide which encodes the respective the full-length amino acid sequence.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

The term "protein", as used herein, includes proteins, polypeptides, and peptides.

The terms "amino acid residue equivalent to", "amino acid corresponding to" and grammatical equivalents thereof are used herein to refer to an amino acid residue of a protein having the similar position and effect as that indicated in a particular amino acid sequence of a particular protein. The person of skill in the art will recognize the equivalence of specified residues in comparable proteins.

The term "property" or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, temperature and/or pH activity profile, feed processing stability, and ability to be secreted.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The terms "protein" and "polypeptide" are used interchangeably herein. In the present disclosure and claims, the conventional one-letter and three-letter codes for amino acid residues are used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein.

By "functional fragment" is meant a fragment of the polypeptide that retains that characteristic properties of that polypeptide. In the context of the present invention, a functional fragment of a phytase or lipolytic enzyme is a fragment that retains the phytase or lipolytic enzyme cleavage capability of the whole protein.

The term "isolated", "recovered" or "purified" refers to a material that is removed from its original environment. The term "substantially purified" means that the material has been purified to at least a substantial degree.

In one aspect, preferably the nucleotide or amino acid sequence is in an isolated form. The term "isolated" means that the sequence is at least substantially free from at least one other component with which the sequence is naturally associated in nature and as found in nature.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a gene" includes a plurality of such candidate agents and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The enzymes for use in the present invention can be produced either by solid or submerged culture, including batch, fed-batch and continuous-flow processes. Culturing is accomplished in a growth medium comprising an aqueous mineral salts medium, organic growth factors, the carbon and energy source material, molecular oxygen, and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulphur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion. In effect, by using an oxygenated hydrocarbon substrate, the oxygen requirement for growth of the microorganism is reduced. Nevertheless, molecular oxygen must be supplied for growth, since the assimilation of the substrate and corresponding growth of the microorganisms, is, in part, a combustion process.

Although the aeration rate can vary over a considerable range, aeration generally is conducted at a rate which is in the range of about 0.5 to 10, preferably about 0.5 to 7, ~volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 50 psig, presently preferably about 0 to 30 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates. At the same time this is balanced by the fact that high atmospheric pressures do increase equipment and operating costs.

The fermentation temperature can vary somewhat, but for filamentous fungi such as *Trichoderma reesei* the temperature generally will be within the range of about 20° C. to 40° C., generally preferably in the range of about 25° C. to 34° C., depending on the strain of microorganism chosen.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. With filamentous fungi, the pH normally is within the range of about 2.5 to 8.0; with *Trichoderma reesei*, the pH normally is within the range of about 3.0 to 7.0. pH range preferences for certain microorganisms are dependent on the media employed to some extent, as well as the particular microorganism, and thus change somewhat with change in media as can be readily determined by those skilled in the art.

While the average retention time of the fermentation admixture in the fermentor can vary considerably, depending in part on the fermentation temperature and culture employed, generally it will be within the range of about 24 to 500 hours, preferably presently about 24 to 400 hours. Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps. As described above, the time to reach this level is not critical and may vary with the particular microorganism and fermentation process being conducted. However, it is well known in the art how to determine the carbon source concentration in the fermentation medium and whether or not the desired level of carbon source has been achieved.

Although the fermentation can be conducted as a batch or continuous operation, fed batch operation is much to be preferred for ease of control, production of uniform quantities of products, and most economical uses of all equipment. If desired, part or all of the carbon and energy source material and/or part of the assimilable nitrogen source such as ammonia can be added to the aqueous mineral medium prior to feeding the aqueous mineral medium to the fermentor. Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermentor employed is not critical, though presently preferred is operation under 15L Biolafitte (Saint-Germain-en-Laye, France).

The collection and purification of the enzymes of the present invention from the fermentation broth can also be done by procedures known per se in the art. The fermentation broth will generally contain cellular debris, including cells, various suspended solids and other biomass contaminants, as well as the desired enzyme product of the present invention, which are preferably removed from the fermentation broth by means known in the art. Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate using techniques such as ultrafiltration, evaporation or precipitation. Precipitating the proteinaceous components of the supernatant or filtrate may be accomplished by means of a salt, e.g., ammonium sulfate. Further purification may optionally be achieved by crystallization or by a variety of chromatographic procedures, e.g., ion exchange chromatography, affinity chromatography or similar art recognized procedures.

Phytases

Phytic acid (myo-inositol hexakisphosphate) is an important constituent in cereals, legumes and oilseed crops. The salt form, phytate, is the major storage form of phosphorous in these plants.

As used herein, the term "phytase" or "phytase activity" refers to a protein or polypeptide which is capable of catalyzing the hydrolysis of phytate to (1) myo-inositol and/or (2) mono-, di-, tri-, tetra- and/or penta-phosphates thereof and (3) inorganic phosphate. For example, enzymes having catalytic activity as defined in Enzyme Commission EC number 3.1.3.8 or EC number 3.1.3.26.

Some phytases in addition to phytate, are capable of hydrolysing at least some of the inositol-phosphates of intermediate degrees of phosphorylation.

The terms "phytase variant" or "variant" or "modified form" refer to a phytase enzyme with an amino acid sequence derived from the amino acid sequence of a parent phytase having one or more amino acid substitutions, insertions, and/or deletions, which together are referred to as "mutations".

The terms "parent phytase" or "parent enzyme" refer to a phytase enzyme from which a phytase variant is derived. A parent phytase can be a wild type phytase or another phytase variant. In particular, in the present invention, a "parent phytase" may be derived from a *Buttiauxella* sp. or *E. coli* as described in WO 99/08539 U.S. Pat. No. 5,876,997, U.S. Pat. No. 6,190,897, and AU 735371 EP 1003379 and JP 2001514869 all of which are incorporated herein by reference. Suitably, the "parent phytase" is derived from *Buttiauxella* strain P1-29 deposited under accession number NCIMB41248 as described WO2006/043178.

The terms "*E. coli* phytase" and "*Buttiauxella* sp. phytase" mean that the enzymes need not have been obtained from a source of *E. coli* or *Buttiauxella* sp. Instead, the enzymes preferably have to have the same functional characteristics or sequence as that of the *E. coli* or *Buttiauxella* sp. phytase. For example, the *Buttiauxella* sp. Phytase may be a variant derived from a *Buttiauxella* sp., but which is not naturally present in *Buttiauxella* species.

The term "*Buttiauxella*" refers to a genus of gram negative, facultatively anaerobic bacteria of the family Enterobacteriaceae and *Buttiauxella* spp include *B. agrestis*, *B. brennerase*, *B. ferragutiae*, *B. gaviniae*, *B. izardii*, *B. noackiae*, and *B. warmboldiae*. Strains of the *Buttiauxella* species are available for example from the American Type Culture Collection (ATCC) and DSMZ, the German National Resource Centre for Biological Material.

Buttiauxella phytases are preferably identified from Buttiauxella spp by the methods described in WO 2006/043178.

In an alternative embodiment the parent phytase or phytase may be derived Citrobacter sp. as described in WO2006/038062.

The terms "wild type phytase" or "wild type" as used herein describe a phytase enzyme with an amino acid sequence found in nature. In particular, the wild-type Buttiauxella phytase is that shown as SEQ ID. No. 1. The wild-type E. coli phytase is shown as SEQ ID No.13 (FIG. 27).

The term "phytase variant" as used herein means a phytase enzyme with an amino acid sequence that differs by at least one amino acid substitution, insertion and/or deletion as compared with the amino acid sequence of the phytase of SEQ. ID NO: 1 or SEQ ID No.13. The terms "variant" and "variation" as used herein merely means that there is a difference between sequence of the amino acid sequence of the phytase variant and the amino acid sequence of SEQ. ID NO: 1 or 13, and does not mean that an amino acid sequence of SEQ. ID NO: 1 or 13 or any other phytase served as a starting material in any way and/or was physically varied, mutated, modified or otherwise altered to yield the variant. Simply put, the phytase variants for use in the present invention may be prepared by any method, and skilled artisans will be readily familiar with numerous methods, some of which are described herein, for making the phytase variants.

Embodiments of variant phytases (e.g., variant Buttiauxella sp. phytases) for use in the present invention are disclosed in WO 2006/043178, WO 2008/097619 and PCT/US2009/41011 all of which are specifically incorporated herein by reference and which describe phytases obtainable from or derived from a parent Buttiauxella sp. and phytases corresponding to a Buttiauxella sp. phytase enzyme. Specifically, WO 2006/043178 describes the mutagenesis of a wild-type phytase enzyme having the sequence disclosed therein as SEQ ID NO: 3. A number of preferred mutations are taught in WO 2006/043178. PCT/US2009/41011 teaches further preferred mutations. Specific preferred mutations are disclosed herein as SEQ ID NOs: 2-6 these represent:

Phytase BP-11 (sometimes referred to as BP 11)—which is the phytase described in at least PCT application WO 2006/043178 and which may be obtained from Danisco A/S. The amino acid sequence is described herein as SEQ ID NO:6.

Phytase BP-17 (sometimes referred to as BP 17)—which is the phytase described in at least PCT application WO 2008/097619 and which may be obtained from Danisco A/S. The amino acid sequence is described herein as SEQ ID NO:3.

BP-110 (sometimes referred to as BP 17 var. 110, or sometimes it is referred to as BP17-110 or BP17 110)—which is the phytase described in at least PCT application PCT/US2009/41011. The amino acid sequence is described herein as SEQ ID NO:4.

BP-111 (sometimes referred to as BP 17 var. 111, or sometimes it is referred to as BP17-111 or BP17 111)—which is the phytase described in at least PCT application PCT/US2009/41011. The amino acid sequence is described herein as SEQ ID NO:5.

BP-112 (sometimes referred to as BP 17 var. 112, or sometimes it is referred to as BP17-112 or BP17 112)—which is the phytase described in at least PCT application PCT/US2009/41011. The amino acid sequence is described herein as SEQ ID NO:2.

The amino acid sequences for BP-11 (SEQ ID NO:6) BP-17 (SEQ ID NO: 3), BP-110 (SEQ ID NO:4), BP-111 (SEQ ID NO:5) and BP-112 (SEQ ID NO:2) are presented in FIG. 3.

When referring to SEQ ID NOs: 1-6 and polypeptides comprising SEQ ID NOs: 1-6, it is envisaged that this also refers to polypeptides that are co- or post-translationally processed during expression, for example by signal peptide cleavage. Post-translational cleavage may also occur at the C-terminal. Therefore in a preferred embodiment the effective fragment thereof (also referred to as functional fragment thereof) is the mature polypeptide produced by the native host or a suitable appropriate expression host.

In another embodiment, the phytase is characterised in that it is derived from Buttiauxella sp. strain P1-29 deposited under accession number NCIMB 41248 as described in WO 2006/043178.

The feed supplements according to the present invention may include phytases having improvements of the characteristics of a parent phytase resulting from modification of one or more amino acid residues of the amino acid sequence of the parent phytase.

Improved phytase enzyme for use in the invention preferably have an identity to SEQ ID NO: 3 or an effective fragment thereof of more than 75%, preferably of more than 80%, more preferably of more than 90%, more preferably of more than 95%, 96%, 97%, 98% preferably of more than 99%. However, it is also envisaged that variants may be heterologous, (i.e. not homologous) to SEQ ID No: 3. For example variants produced by recombination techniques such as exo-mediated recombination, or family shuffling, may result in variants, although prepared using the parent phytase, may have less than 75% homology.

Suitably the variants show enhanced stability characteristics with respect to any one of the following: thermal stability, thermal activity, pH range, pepsin stability, specific activity, substrate specificity, and broader substrate specificity. Suitable methods for determining these characteristics are disclosed herein.

The term "enhanced stability" in the context of a property such as stability at higher temperatures, lower pH, etc. refers to a higher retained enzyme activity over time as compared to another identified phytase such as that of, in the case of Buttiauxella, SEQ ID NO: 1. Unless another phytase is specifically identified, the term "enhanced stability" when used herein, will refer to a higher retained enzyme activity over time as compared to the phytase of SEQ ID NO: 1.

The terms "thermally stable" and "thermostable" refer to phytases of the present disclosure that retain a specified amount of enzymatic activity after exposure to an elevated temperature. Phytase variants according to this disclosure are considered thermostable at a specified temperature if the enzyme retains greater than 50% of its activity after exposure to the specified temperature for 10 minutes at pH 5.5 in buffer.

The term "enhanced thermal activity" as it pertains to phytase variants of the present disclosure means that the phytase variant exhibits the same or an increased amount of phytase enzyme activity at elevated temperature as compared to the phytase enzyme activity of another identified phytase such as that of SEQ ID NO: 1. Unless another phytase is specifically identified, the term "improved thermal activity" when used herein will refer to the thermal activity of a phytase variant of this disclosure as compared to the thermal activity of the phytase of SEQ ID NO: 1.

Variants of this disclosure as described in WO 2006/043178, WO 2008/097619 and PCT/US2009/41011, the disclosure of which is incorporated herein by reference, are described by the following nomenclature: [original amino acid residue of SEQ. ID NO: 1/position of original amino acid residue in SEQ. ID NO: 1/substituted amino acid residue]. For example, in SEQ ID NO: 2, the substitution of threonine (T) for the original alanine (A) in position 89 of SEQ ID NO: 1 is represented as A89T. When a position suitable for substitution is identified herein without a specific amino acid suggested, it is to be understood that any amino acid residue may be substituted for the amino acid residue present in the position. Where a variant phytase contains a deletion in comparison with other phytases the deletion is indicated with "*". For example, a deletion at position A89 of SEQ. ID NO: 1 is represented as A89*. A deletion of two or more consecutive amino acids is indicated, for example, as (89-91)*.

The terms "derived from" and "obtained from" refer to not only a phytase produced or producible by a strain of the organism in question, but also a phytase encoded by a DNA sequence isolated from such strain and produced in a host organism containing such DNA sequence. Additionally, the terms refers to a phytase which is encoded by a DNA sequence of synthetic and/or cDNA origin and which has the identifying characteristics of the phytase in question. Hence, a phytase that is "derived from" and "obtained from" another phytase does not necessarily mean that the phytase has been physically derived or physically obtained from the second phytase, but rather can also mean that the phytase in question has been prepared using knowledge or ideas derived from knowledge of the second phytase.

In particular, the improvements in phytase characteristics are directed to the enzyme stability under food and feed processing conditions, to the enzyme stability during stomach transit, and to the enzyme activity and stability in human or animal stomach and/or intestinal tract making the improved variants particularly suitable for use as feed supplements. Thus, such improvements comprise among other parameters the increase in stability at elevated temperatures, preferably at temperatures above 65° C., the increase in stability against proteolytic digestion, preferably protease of the digestive tract such as pepsin, the increase in catalytic activity at low pH, preferably catalytic activity below pH 5.5, and the general efficiency of releasing phosphate groups from phytate, and preferably in addition inositol phosphates.

Therefore, in some embodiments the invention relates to feed supplements comprising phytase variants with improved characteristics that, when compared to the parent phytase, comprise mutations at one or more of the positions disclosed in WO 2006/043178, WO 2008/097619 and PCT/US2009/41011 and/or at corresponding positions in a phytase homologous to the phytase as shown in the amino acid sequence of Seq ID No 1. These positions are characterized in that mutagenesis of these positions lead to an improvement in the enzymes characteristics.

Variants with higher thermal stability (thermal stability difference) are preferably determined using the methods disclosed in WO 2006/043178.

The variant phytase enzyme for use in the present invention preferably has a thermal stability difference (T.D) of at least 1.5, more preferably 2, 2.5, 3, 3.5, 4, 5, 6, 7, 8, 9, 10, 11, 12, 13, 14, 15, 16, 17, 18, 19 most preferably at least 20.

Variants with higher proteolytic stability are preferably determined by the methods disclosed in WO 2006/043178.

Preferably the phytase enzyme variant for use in the present invention has a proteolytic stability (residual activity) of at least 45%, preferably 50%, 55%, more preferably at least 60% or 65%, most preferably at least 70%.

Preferably the phytase variant for use in the present invention has a specific activity of greater than 100% of wt activity at pH 4.0, preferably greater than 105%, 110%, more preferably greater than 114%.

In one aspect, preferably the amino acid sequence is in a purified form. The term "purified" means that the sequence is in a relatively pure state at least 1%, 5% pure or 10% pure, more preferably at least 20%, 30%, 40%, 50%, 60%, 70%, 80%, 90% pure. In a preferred embodiment, when referring to a polypeptide, the purity as defined above is determined in terms of being purified from other polypeptides by SDS-PAGE electrophoresis.

Variants/Derivatives

The present invention also encompasses the use of variants, homologues and derivatives of any amino acid sequence of an enzyme or of any nucleotide sequence encoding such an enzyme.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol*. (1995) 13(4), 132-134.

Other Components

The feed supplement of the present invention may be used in combination with other components or carriers.

Suitable carriers for feed enzymes include maltodextrin, limestone (calcium carbonate), cyclodextrin, wheat or a wheat component, sucrose, starch, anti-foam, Na2SO4, Talc, PVA and mixtures thereof. In addition there are a number of encapsulation techniques including those based on fat/wax coverage, adding plant gums etc.

Examples of other components include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

As used herein the term "thickener or gelling agent" as used herein refers to a product that prevents separation by slowing or preventing the movement of particles, either droplets of immiscible liquids, air or insoluble solids.

The term "stabiliser" as used here is defined as an ingredient or combination of ingredients that keeps a product (e.g. a food product) from changing over time.

The term "emulsifier" as used herein refers to an ingredient (e.g. a food product ingredient) that prevents the separation of emulsions.

As used herein the term "binder" refers to an ingredient (e.g. a food ingredient) that binds the product together through a physical or chemical reaction.

The term "crystal modifier" as used herein refers to an ingredient (e.g. a food ingredient) that affects the crystallisation of either fat or water.

"Carriers" or "vehicles" mean materials suitable for compound administration and include any such material known in the art such as, for example, any liquid, gel, solvent, liquid diluent, solubiliser, or the like, which is non-toxic and which does not interact with any components of the composition in a deleterious manner.

Examples of nutritionally acceptable carriers include, for example, grain, water, salt solutions, alcohol, silicone, waxes, petroleum jelly, vegetable oils, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

As used herein the term "component suitable for animal or human consumption" means a compound which is or can be added to the composition of the present invention as a supplement which may be of nutritional benefit, a fibre substitute or have a generally beneficial effect to the consumer.

By way of example, the components may be prebiotics such as alginate, xanthan, pectin, locust bean gum (LBG), inulin, guar gum, galacto-oligosaccharide (GOS), fructo-oligosaccharide (FOS), lactosucrose, soybean oligosaccharides, palatinose, isomalto-oligosaccharides, gluco-oligosaccharides and xylo-oligosaccharides.

Lipolytic Enzymes

Lipolytic enzymes (EC 3.1.1.3), which can be defined as carboxylesterases which catalyze the hydrolysis of acylglycerols, are physiologically very important enzymes as one of the three major digestive enzymes together with amylases and proteases. They hydrolyse lipids to glycerol and fatty acids, but can also function in esterification or transesterification reactions.

In preferred embodiments, the lipolytic enzyme for use in the present invention is a lipolytic enzyme derived from the filamentous fungus *Aspergillus tubingensis* as disclosed in WO 98/45453 and deposited under the Budapest Treaty with the NCIMB on 24 Feb. 1997 under the accession number 40863. It will be understood that the lipolytic enzyme may be derived from *Aspergillus*, or alternatively may be recombinantly produced in another organism such as *E. Coli*.

Preferably, the lipolytic enzyme comprises a polypeptide comprising the amino acid sequence as shown in SEQ ID NO: 7 or 8 or a polypeptide having at least 70%, 80%, 90%, 95%, 98% or 99% identity thereto; or a polypeptide which is produced by expression of a nucleotide sequence comprising the sequence of SEQ ID NO: 9 or 10; or a sequence which differs from SEQ ID NO:9 or 10 due to the degeneracy of the genetic code; or a sequence which has at least 70%, 80%, 90%, 95%, 98% or 99% identity to SEQ ID NO: 9 or 10.

It will be understood that any general definitions of features disclosed in relation to phytases can be equally applied to lipolytic enzymes and, for the sake of conciseness will not be repeated here.

In a further preferred embodiment, the lipolytic enzyme for use in the present invention is produced in a *Trichoderma reesei* cell as disclosed herein.

The method of producing the lipolytic enzyme comprising the steps of:
(i) providing a *Trichoderma reesei* cell comprising
   a) at least one heterologous nucleotide sequence encoding a lipolytic enzyme comprising an amino acid sequence shown as SEQ ID NO: 7 or SEQ ID NO: 8 or an amino acid sequence which has at least 70% sequence identity to SEQ ID NO: 7 or 8; and/or
   b) at least one heterologous nucleotide sequence encoding a lipolytic enzyme wherein the nucleotide sequence comprises the nucleotide sequence shown as SEQ ID NO: 9 or SEQ ID NO: 10 or a nucleotide sequence which has at least 70% sequence identity to SEQ ID NO: 9 or SEQ ID NO: 10; and/or
   c) at least one heterologous nucleotide sequence encoding a lipolytic enzyme wherein the nucleotide sequence comprises a nucleotide sequence which hybridizes to SEQ ID NO: 9 or SEQ ID NO: 10 or a nucleotide sequence which has at least 70% sequence identity to SEQ ID NO: 9 or SEQ ID NO: 10 or the complement of any thereof under stringent conditions; and/or
   d) at least one heterologous nucleotide sequence encoding a lipolytic enzyme wherein the nucleotide sequence is identical to the nucleotide sequence shown as SEQ ID NO: 9 or SEQ ID NO: 10 except for the degeneracy of the genetic code; and
(ii) culturing the cell under conditions to allow for expression of said heterologous nucleotide sequence(s) encoding said lipolytic enzyme.

It will be understood that as defined herein, the term stringent conditions refers to washing at. 50° C. and 0.2×SSC {1×SSC=0.15 M NaCl, 0.015 M Na3citrate pH 7.0}.

It will be understood that these conditions may also be high stringent conditions which are defined herein as washing at 65° C. and 0.1×SSC {1×SSC=0.15 M NaCl, 0.015 M Na3citrate pH 7.0}.

Alternatively there is provided a method of producing a lipolytic enzyme comprising the steps of:
(i) transfecting or transforming a *Trichoderma reesei* cell with
   a) at least one heterologous nucleotide sequence encoding a lipolytic enzyme comprising an amino acid sequence shown as SEQ ID NO: 7 or SEQ ID NO: 8 or an amino acid sequence which has at least 70% sequence identity to SEQ ID NO: 7 or 8; and/or
   b) at least one heterologous nucleotide sequence encoding a lipolytic enzyme wherein the nucleotide sequence comprises the nucleotide sequence shown as SEQ ID NO: 9 or SEQ ID NO: 10 or a nucleotide sequence which has at least 70% sequence identity to SEQ ID NO: 9 or SEQ ID NO: 10; and/or
   c) at least one heterologous nucleotide sequence encoding a lipolytic enzyme wherein the nucleotide sequence comprises a nucleotide sequence which hybridizes to SEQ ID NO: 9 or SEQ ID NO: 10 or a nucleotide sequence which has at least 70% sequence identity to SEQ ID NO: 9 or SEQ ID NO: 10 or the complement of any thereof under stringent conditions; and/or d) at least one heterologous nucleotide sequence encoding a lipolytic enzyme wherein the nucleotide sequence is identical to the nucleotide sequence shown as SEQ ID NO: 9 or SEQ ID NO: 10 except for the degeneracy of the genetic code; and (ii) culturing the cell under conditions to allow for expression of said heterologous nucleotide sequence(s) encoding said lipolytic enzyme.

Further there is provided a method of producing a lipolytic enzyme comprising the steps of:

(i) transfecting or transforming a *Trichoderma reesei* cell with a) at least one heterologous nucleotide sequence encoding a lipolytic enzyme comprising an amino acid sequence shown as SEQ ID NO: 7 or SEQ ID NO: 8 or an amino acid sequence which has at least 70% sequence identity to SEQ ID NO: 7 or 8; and/or b) at least one heterologous nucleotide sequence encoding a lipolytic enzyme wherein the nucleotide sequence comprises the nucleotide sequence shown as SEQ ID NO: 9 or SEQ ID NO: 10 or a nucleotide sequence which has at least 70% sequence identity to SEQ ID NO: 9 or SEQ ID NO: 10; and/or c) at least one heterologous nucleotide sequence encoding a lipolytic enzyme wherein the nucleotide sequence comprises a nucleotide sequence which hybridizes to SEQ ID NO: 9 or SEQ ID NO: 10 or a nucleotide sequence which has at least 70% sequence identity to SEQ ID NO: 9 or SEQ ID NO: 10 or the complement of any thereof under stringent conditions; and/or d) at least one heterologous nucleotide sequence encoding a lipolytic enzyme wherein the nucleotide sequence is identical to the nucleotide sequence shown as SEQ ID NO: 9 or SEQ ID NO: 10 except for the degeneracy of the genetic code; and (ii) repeating step (i) on the cell to sequentially transfect or transform the cell with at least one additional heterologous nucleotide sequence as defined in (i)(a), (i)(b) or (i)(c) (e.g. such as a heterologous nucleotide sequence encoding a lipolytic enzyme comprising an amino acid sequence shown as SEQ ID NO: 7 or SEQ ID NO: 8 or an amino acid sequence which has at least 40% sequence identity to SEQ ID NO: 7 or 8); and (iii) culturing the cell under conditions to allow for expression of said heterologous nucleotide sequence(s) encoding said lipolytic enzyme.

*Trichoderma reesei* is capable of producing the lipolytic enzymes in significantly high yields.

Furthermore, the lipolytic enzymes produced by the methodology disclosed herein are not over glycosylated and therefore have good enzyme activity.

Bradner et al. (in Current Genetics, 44: 224-230, (2003)) used *Trichoderma reesei* as an expression host organism in their search for previously unknown lipolytic enzymes. A lipolytic enzyme from an Antarctic isolate of *Penicillium allii* was cloned and expressed in *Trichoderma reesei*. Bradner et al. concluded that the methods described would be useful for prospecting for potentially novel lipolytic enzyme genes but no suggestion was made that *T. reesei* could be used for over expression of proteins.

Also disclosed in another aspect is a method of producing a lipolytic enzyme comprising the steps of:

(i) providing a transformed or transfected *Trichoderma reesei* cell comprising at least one heterologous nucleotide sequence encoding a lipolytic enzyme;

(ii) culturing the cell at a pH 4 to pH 5.5 under conditions to allow for expression of said heterologous nucleotide sequence(s) encoding said lipolytic enzyme;

(iii) isolating, purifying or concentrating the enzyme in a medium at pH 5.5 to pH 6.5.

In this aspect, preferably the lipolytic enzyme:

a) comprises an amino acid sequence shown as SEQ ID NO: 7 or SEQ ID NO: 8 or comprises an amino acid sequence which has at least 70% sequence identity to SEQ ID NO: 7 or 8; and/or b) is encoded by a nucleotide comprising the sequence shown as SEQ ID NO: 9 or SEQ ID NO: 10 or comprising a nucleotide sequence which has at least 70% sequence identity to SEQ ID NO: 9 or SEQ ID NO: 10; and/or c) is encoded by a nucleotide sequence comprising a nucleotide sequence which hybridizes to SEQ ID NO: 9 or SEQ ID NO: 10 or comprises a nucleotide sequence which is at least 70% sequence identity to SEQ ID NO: 9 or SEQ ID NO: 10 or the complement of any thereof under stringent conditions; and/or d) at least one heterologous nucleotide sequence encoding a lipolytic enzyme wherein the nucleotide sequence is identical to the nucleotide sequence shown as SEQ ID NO: 9 or SEQ ID NO: 10 except for the degeneracy of the genetic code.

Suitably there may be at least one heterologous nucleotide sequence encoding the lipolytic enzyme in the *Trichoderma reesei* cell. There may be two or more copies (i.e. multiple copies) of the or each heterologous nucleotide sequence encoding the lipolytic enzyme according to the present invention in the *Trichoderma reesei* cell. Each heterologous nucleotide sequence is associated with and is under the control of a promoter. Suitably each heterologous nucleotide sequence may have a separate promoter associated with it and be under the control of that promoter. The promoters may be the same or different.

Thus, the *Trichoderma reesei* cell may comprise or be transfected or transformed with at least 2 heterologous nucleotide sequences encoding the lipolytic enzyme.

Suitably, the (or each) heterologous nucleotide sequence may comprise a nucleotide sequence which encodes a signal peptide, which nucleotide sequence encoding said signal peptide is operably linked to said nucleotide sequence encoding said lipolytic enzyme. If there are multiple heterologous nucleotide sequences and wherein more than one has a signal sequence associated therewith, then the signal sequences may be the same or different.

Suitably the lipolytic enzyme may comprise an endogenous or exogenous signal peptide. When the signal peptide is endogenous—it means that the signal peptide is that which is naturally linked with the lipolytic enzyme when produced naturally. For example, the signal peptide may be the signal peptide in *Aspergillus tubingensis* which is naturally linked with the lipolytic enzyme when found in *Aspergillus tubingensis*.

The term "heterologous" as used herein means that it is does not occur naturally in the *Trichoderma reesei* cell. In other words, it is exogenous to the *Trichoderma reesei* cell. For example the term "heterologous nucleotide sequence" as used herein means that the nucleotide sequence does not occur naturally in the *Trichoderma reesei* cell. In other words, the nucleotide sequence is exogenous to the *Trichoderma reesei* cell. The term also includes multiple copies of the naturally occurring sequence as such additional multiple copies would be heterologous.

The heterologous nucleotide sequence may be obtained or obtainable from a microorganism, particularly a fungi.

The heterologous nucleotide sequence may be obtained or obtainable from *Aspergillus*, particularly *Aspergillus tubingensis*.

In preferred embodiments of the above aspects, said *Trichoderma reesei* cell has at least two genes encoding non-lipolytic enzymes suppressed.

Yet further provided is a lipolytic enzyme obtainable by the methods of the present invention.

Also provided is a transformed or transfected *Trichoderma reesei* cell comprising:
   a) at least one heterologous nucleotide sequence encoding a lipolytic enzyme protein having at least 70% sequence identity to SEQ ID NO: 7 or 8; and/or
   b) at least one heterologous nucleotide sequence encoding a lipolytic enzyme wherein the nucleotide sequence comprises the nucleotide sequence shown as SEQ ID NO: 9 or SEQ ID NO: 10 or a nucleotide sequence which has at least 70% sequence identity to SEQ ID NO: 9 or SEQ ID NO: 10; and/or
   c) at least one heterologous nucleotide sequence encoding a lipolytic enzyme wherein the nucleotide sequence comprises a nucleotide sequence which hybridizes to SEQ ID NO: 9 or SEQ ID NO: 10 or a nucleotide sequence which is at least 70% sequence identity to SEQ ID NO: 9 or SEQ ID NO: 10 or the complement of any thereof under stringent conditions; and/or
   d) at least one heterologous nucleotide sequence encoding a lipolytic enzyme wherein the nucleotide sequence is identical to the nucleotide sequence shown as SEQ ID NO: 9 or SEQ ID NO: 10 except for the degeneracy of the genetic code; and
wherein said *Trichoderma reesei* cell has at least two genes encoding non-lipolytic enzymes suppressed.

Preferably, said *Trichoderma reesei* cell according to any of the preceding aspects has at least three genes encoding non-lipolytic enzymes suppressed.

Preferably, said *Trichoderma reesei* cell according to any of the preceding aspects has at least four genes encoding non-lipolytic enzymes suppressed.

"Suppressed" means that the cell does not express the relevant non-lipolytic enzyme at the same level as the non-transformed/transfected cell. In some embodiments, "suppressed" means that the cell does not express the relevant non-lipolytic enzyme. The suppression may be brought about by techniques known in the art, such as by deletions.

Preferably, at least one of the genes encoding a non-lipolytic enzyme that is suppressed is a cellulase gene.

Preferably, at least two of the genes encoding a non-lipolytic enzyme that is suppressed are cellulase genes.

An example of at least one of the genes encoding a non-lipolytic enzyme that is suppressed is a gene encoding a cellobiohydrolases (e.g. CBHI or CBHII).

Another example of at least one of the genes encoding a non-lipolytic enzyme that is suppressed is a gene encoding an endoglucanases (e.g. EGI and EGII).

In some embodiments the *Trichoderma reesei* cell is a cell in which the endogenous genes encoding one or both cellobiohydrolases (CBHI and CBHII) and/or one or both of the endoglucanases (EGI and EGII) are deleted or disrupted. Suitably the *Trichoderma reesei* cell may be a non-GMM cell or derivative thereof, for example a derivative of the strain RL-P37. Suitably the *Trichoderma reesei* cell may be a derivative of the strain RL-P37 that is produced using the method set out in Example 7.

In some embodiments, the heterologous nucleotide sequence may encode a lipolytic enzyme comprising an amino acid sequence having at least 70%, at least 75%, at least 80%, at least 85%, at least 90%, at least 95% or at least 98% sequence identity to SEQ ID NO: 7 or SEQ ID No. 8.

In some embodiments the heterologous nucleotide sequence may encode a lipolytic enzyme and comprises a nucleotide sequence having at least 70%, at least 75%, at least 80%, at least 85%, at least 90%, at least 95% or at least 98% sequence identity to SEQ ID NO: 9 or SEQ ID No. 10.

Preferably, the heterologous nucleotide sequence encodes a lipolytic enzyme comprising an amino acid sequence having at least 70%, at least 75%, at least 80%, at least 85%, at least 90%, at least 95% or at least 98% sequence identity to SEQ ID NO: 7 or SEQ ID No. 8.

Preferably, the heterologous nucleotide sequence encodes a lipolytic enzyme and comprises a nucleotide sequence at least 70%, at least 75%, at least 80%, at least 85%, at least 90%, at least 95% or at least 98% sequence identity to SEQ ID NO: 9 or SEQ ID No. 10.

The amino acid sequence identity of a number of lipolytic enzymes to the lipolytic enzyme from *Aspergillus tubingensis* having the sequence shown in SEQ ID NO: 9 (also called herein lipase 3) are shown in Table 1 below.

TABLE 1

Lipolytic enzymes with sequence identity to the lipolytic enzyme from *Aspergillus tubingensis* (lipase 3).

| Lipolytic enzymes from different fungi | Accession No. | Amino acid sequence identity % |
| --- | --- | --- |
| *A. niger* CBS 513.88 | XP_001397501.1 | 93 |
| *Aspergillus niger* | ABG73613.1 | 93 |
| *Aspergillus niger* | ABG37906.1| | 93 |
| *Aspergillus nidulans* FGSCA4 | XP_681315.1 | 61 |
| *Aspergillus clavatus* NRRL 1 | XP_001276337.1 | 57 |
| *Neosartorya fischeri* NRRL 181 | XP_001266329.1 | 60 |
| *Aspergillus fumigatus* Af293 | XP_748138.1 | 59 |
| *Aspergillus oryzae* RIB40 | XP_001818694.1 | 56 |
| *Aspergillus terreus* NIH2624 | XP_001218444.1 | 54 |
| *Penicillium chrysogenum* Wisconsin 54-1255 | CAP96359.1 | 55 |
| *Aspergillus niger* | ABG73614.1 | 54 |
| *Aspergillus niger* | XP_001393532.1 | 53 |
| *Thermomyces lanuginosus* | O59952.1 | 50 |
| *Penicillium marneffei* ATCC 18224 | XP_002147144.1 | 49 |
| *Aspergillus oryzae* R | XP_001824529.1 | 44 |
| *Phaeosphaeria nodorum* SN15 | XP_001796872.1 | 45 |
| *Penicillium cyclopium* | P61869.1 | 42 |
| *Penicillium camemberti*. | 1TIA_A. | 42 |

The *Trichoderma reesei* host cell may be any *Trichoderma reesei* cell. The cell may be considered to be a wild type *Trichoderma reesei* cell. The *Trichoderma reesei* cell may be one from which genes encoding one or more secreted cellobiohydrolases (CBHI or CBHII) has/have been deleted or disrupted so that they are not expressed. Suitably the *Trichoderma reesei* cell may be a non-genetically modified cell or derivative thereof, for example a derivative of the strain RL-P37. Suitably the *Trichoderma reesei* cell may be a derivative of the strain RL-P37 that is produced using the method set out in Example 10.

The enzyme may be produced in a fermentor which may comprise about 3 liters to about 20 liters culture media. In another embodiment the present invention is carried out as a 10-16 liter, preferably a 14 liter scale fermentation. In one embodiment, preferably the fermentation is carried out with more than about 12 liters, preferably more than about 14 liters.

The *Trichoderma reesei* host cell is preferably suitable for use in large scale fermentation.

In preferred embodiments, lipolytic enzyme production is carried out on a commercial scale. In this respect, the fermentation is carried out at more than about 50,000 liters scale, preferably more than about 80,000 liters scale, preferably at more than about 200,000 liter scale fermentation.

In one embodiment the total protein produced by the method is well in excess of about 20 g/liter.

Of the total protein produced the majority is the desired lipolytic enzyme. In one embodiment the total secreted protein produced comprises at least 50% of the desired lipolytic enzyme. In one embodiment the total secreted protein produced comprises at least 60% of the desired lipolytic enzyme. In one embodiment the total secreted protein produced comprises at least 70% of the desired lipolytic enzyme. In one embodiment the total secreted protein produced comprises at least 80% of the desired lipolytic enzyme.

Suitably the method may comprise selection of transformants which have been screened for production of the lipolytic enzyme (high producers of the desired enzyme are preferentially selected).

In one embodiment suitably the method may comprise a first transformation step wherein a *Trichoderma reesei* cell is transformed with at least one heterologous nucleotide sequence encoding the lipolytic enzyme defined herein, selection of transformants which have been screened for production of the lipolytic enzyme (high producers of the desired enzyme are preferentially selected), and a second transformation step (i.e. retransformation step) of a selected transformant with at least one heterologous nucleotide sequence encoding the lipolytic enzyme defined herein, followed by further selection of new transformants which have been screened for production of the lipolytic enzyme (high producers of the desired enzyme are preferentially selected).

In some embodiments the lipolytic enzyme for use in the present invention maybe glycosylated. In some embodiments, the lipolytic enzyme may be N-glycosylated at N32 (when numbered using SEQ ID NO: 8) or at an equivalent position for other lipolytic enzymes according to the invention. This aspect may impart significant advantages in that the activity of the enzyme is not disrupted or reduced by glycosylation of the enzyme. Without wishing to be bound by theory, reduction in activity of the lipolytic enzyme can be seen when it is produced in other hosts such as *A. tubingensis* and is thought to be due to over-glycosylation of the enzyme at least the N242 site.

The lipolytic enzyme produced by the method disclosed herein is therefore distinguishable from the lipolytic enzyme produced in other hosts, e.g. *A. tubingensis*, because of the degree of glycosylation of the enzyme, particularly at the N32 site. In some embodiments of the present invention the enzyme has glycosylation at, at least, the N32 site.

Suitably the lipolytic enzyme may be produced with a signal peptide. In other words the heterologous nucleotide sequence used in the present invention comprises a portion thereof which encodes a signal peptide.

The signal peptide may be used to direct secretion of the lipolytic enzyme through a particular cell membrane. The signal peptide sequences may be endogenous or exogenous to the lipolytic enzyme coding sequence. For instance, the signal peptide may be the signal peptide which is endogenous to the lipolytic enzyme is *Aspergillus tubingensis*. Alternatively, the coding sequence for the signal peptide may be obtained (or obtainable) from a cellobiohydrolase gene of *Trichoderma reesei*.

However, any signal peptide coding sequence capable of directing the expressed lipolytic enzyme into the secretory pathway of a *Trichoderma reesei* cell of choice may be used.

When we refer to improving one or more of the following: expression of the lipolytic enzyme, glycosylation of the lipolytic enzyme, enzyme activity and/or yield this is compared with conventional methods of expressing this lipolytic enzyme. For example, there is provided an improved expression of the lipolytic enzyme, glycosylation of the lipolytic enzyme, enzyme activity and/or yield compared with production of the lipolytic enzyme in another host organism (i.e. a host organism other than *T. reesei*). In particular, there is an improved expression of the lipolytic enzyme, glycosylation of the lipolytic enzyme, enzyme activity and/or yield of the lipolytic enzyme by the present invention (i.e. produced in the *Trichoderma reesei* cell) as compared with expression of the same lipolytic enzyme in an *Aspergillus tubingensis* cell (for example as taught in WO98/45453, as incorporated herein by reference).

The term "improved glycosylation" as used herein means that, preferably, glycosylation occurs at N32 (when numbered using SEQ ID NO: 8). Without wishing to be bound by theory, in some situations, the lipolytic enzyme produced in host cells other than *T. reesei* (and particularly in *Aspergillus tubingensis* (e.g. as taught in WO98/45453)) may be glycosylated (or overglycosylated), particularly at N242. Therefore, the lipolytic enzyme produced in host cells other than *T. reesei* and particularly in *Aspergillus tubingensis* (e.g. as taught in WO98/45453) may be glycosylated at both N32 and N242 sites. However, and without wishing to be bound by theory, the N242 site is in the vicinity of one of the active site residues, namely His258 of SEQ ID No. 8. Thus, it is believed that glycosylation (or overglycosylation) at the N242 site can lead to a reduced activity (i.e. lipase activity) of the enzyme. The lipolytic enzyme of the present invention does not have reduced activity. Glycosylation of the lipolytic enzyme of the present invention may occur at the N32 site which is away from the active site residues, such as His258.

The term "improved enzyme activity" as used herein means that the activity is the same as or greater than the lipase activity of the lipolytic enzyme produced naturally by *Aspergillus tubingensis*.

By enzyme activity we mean at least lipase activity. Enzyme activity (e.g. lipase activity) can be measured using the relevant protocols set out below in the Examples section.

It has been surprisingly found that the lipolytic enzyme produced in accordance with the method disclosed herein is easy to isolate from the medium into which it has been excreted—i.e. the culture (fermentation) broth—as high expression levels are obtained.

Thus, the method may involve one or more of the following steps to the medium into which the lipolytic enzyme has been secreted following culturing of the cell: diluting the medium (preferably with water); separating the cell(s) from the medium; concentrating the medium (preferably wherein said medium is cell-free); granulating said medium (preferably wherein said medium is cell-free).

The method may also involve the following steps to the medium into which the enzyme has been secreted following culturing of the cell: diluting the medium (preferably with water); separating the cell(s) from the medium; concentrating the medium (preferably wherein said medium is cell-free); and optionally granulating said medium (preferably wherein said medium is cell-free).

The method also optionally involves undertaking the following steps to the medium into which the enzyme has been secreted following culturing of the cell: diluting the medium (preferably with water); separating the cell(s) from the medium; concentrating the medium (preferably wherein said medium is cell-free); and granulating said medium (preferably wherein said medium is cell-free).

Preferably, the method involves the following steps to the medium into which the enzyme has been secreted following culturing of the cell: diluting the medium with water; separating the cell(s) from the medium; concentrating the medium wherein said medium is cell-free; and optionally granulating said medium wherein said medium is cell-free.

In a preferred aspect, the method involves the following steps to the medium into which the enzyme has been secreted following culturing of the cell: diluting the medium with water; separating the cell(s) from the medium; concentrating the medium wherein said medium is cell-free; and granulating said medium wherein said medium is cell-free.

Preferably the lipolytic enzyme precipitates out of solution in the fermentation broth. Preferably, the lipolytic enzyme precipitate is re-solubilised by pH adjustment. Preferably the pH is adjusted to a pH above the pH of the fermentation broth.

In addition to the advantages mentioned above, another advantage of the enzyme produced by the method is that it enables commercial scale production of the lipolytic enzyme. The method allows for the lipolytic enzyme to be produced in a high yield.

One advantage of the lipolytic enzyme disclosed herein is that it has surprisingly been found that it is possible to go directly from the transformation and screening step (i.e. say from the microtitre plate) directly to large scale fermentation (e.g. at least 14 liter fermentation). This is surprisingly possible because the screening step (particularly the microtitre plate results) are highly predictive of good performance in the large scale fermentation. This contrasts with conventional methods where it is often necessary to cultivate the strain in flasks before moving to larger scale fermentation) This has significant advantages in shortening the production time and/or simplifying the overall procedure and/or reducing costs.

A further advantage is that the methods described herein provide an enhanced/increased expression and/or an improved yield of the lipolytic enzyme compared with conventional methods of expressing this lipolytic enzyme. For example, there is provided an enhanced/increased expression and/or an improved yield of the lipolytic enzyme compared with production of the lipolytic enzyme in another host organism (i.e. a host organism other than *T. reesei*). In particular, there is an increased expression and/or an improved yield of the lipolytic enzyme (i.e. produced in the *Trichoderma reesei* cell) as compared with expression of the same lipolytic enzyme in an *Aspergillus tubingensis* cell (for example as taught in WO98/45453, as incorporated herein by reference).

A further advantage is that the lipolytic enzyme produced in accordance with the methods disclosed herein is easy to produce and isolate and/or purify and/or concentrate.

A further advantage is that the lipolytic enzyme produced in accordance with the disclosed method is easy to re-solubilise.

A further advantage is that the lipolytic enzyme produced in accordance with the disclosed method may be used as a granulate or as a solution.

Lipolytic Enzyme

The term "lipolytic enzyme" as used herein means an enzyme with triacylglycerol hydrolysing activity (classified as E.C. 3.1.1.3).

Suitably, the lipolytic enzyme for use in the present invention may exhibit one or more of the following additional activities: glycolipase activity (E.C. 3.1.1.26), phospholipase A2 activity (E.C. 3.1.1.4), phospholipase A1 activity (E.C. 3.1.1.32) or phospholipase B activity (E.C. 3.1.1.5). The term "glycolipase activity" as used herein encompasses "galactolipase activity".

Isolated

In one aspect, preferably the lipolytic enzyme for use in the present invention is in an isolated form. The term "isolated" means that the lipolytic enzyme is at least substantially free from at least one other component with which the lipolytic enzyme is naturally associated in nature and as found in nature. The term "isolated" may mean that the lipolytic enzyme is at least substantially free from at least one other component in the culture media in which it is produced. The lipolytic enzyme of the present invention may be provided in a form that is substantially free of one or more contaminants with which the substance might otherwise be associated or with which the enzyme may be produced.

Thus, for example it may be substantially free of the cell(s) or one or more potentially contaminating polypeptides and/or nucleic acid molecules. The lipolytic enzyme may be isolated by separating the cell(s) from the broth during or after fermentation so that the lipolytic enzyme remains in the broth. The lipolytic enzyme may be isolated by subjecting the fermentation broth to cell separation by vacuum filtration.

Purified

In one aspect, preferably the lipolytic enzyme for use in the present invention is in a purified form. The term "purified" means that the given component is present at a high level. The component is desirably the predominant component present in a composition. Preferably, it is present at a level of at least about 60%, or at least about 65%, or at least about 70%, or at least about 75%, or at least about 80% said level being determined on a dry weight/dry weight basis with respect to the total composition under consideration. For some embodiments the amount is at least about 85% said level being determined on a dry weight/dry weight basis with respect to the total composition under consideration.

Concentrate

In one aspect, preferably the lipolytic enzyme for use in the present invention is used as a concentrate. The concentrate may be a concentrated form of the medium into which the enzyme has been excreted. Preferably, the concentrate may be a concentrated form of the medium into which the enzyme has been secreted and wherein the cell(s) have been removed.

Materials and Methods

1. Lipase Assay at pH 5.5

As used herein, 1 LIPU (lipase unit) is defined as the amount of enzyme which releases 1 μmol of $H^+$ per minute under the conditions described herein below.

5% (v/v) tributyrin substrate is prepared by Mixing 15.00 ml tributyrin, 50.00 ml emulsifying agent and 235 ml dist. water for 20 sec on a homogenizer. The pH of the substrate is adjusted to approx. 5.4 with 0.5 M NaOH.

Emulsifying agent is prepared by mixing 17.9 g NaCl, 0.41 g $KH_2PO_4$, 400 ml dist. water, and 450 ml glycerol in a 2000 ml beaker. Under vigorous stifling add 6.0 g Gum Arabic and continue stirring until gum Arabic is completely dissolved. Transfer the solution to a 1000 ml volumetric flask and fill to the mark with dist water.

For dry samples: in a volumetric flask dissolve an amount of enzyme calculated to give a final solution of approximately 3.5 LIPU/ml in half of the final dilution and subject to magnetic stifling for 20 minutes After stifling, adjust to final dilution with distilled water. Any further dilution should be made with distilled water. Samples in solution are diluted directly in distilled water 25.00 mL of substrate is adjusted to 30.0° C.

Adjust substrate pH to 5.50 with NaOH/HCl

While stirring, add 2.00 mL sample, and initiate immediately pH-stat titrator.

Stop titration after 6 minutes.

Calculate slope of the titration curve. The slope of the titration curve is calculated from data between 3 and 6 min. The slope must be in the interval 0.1-0.2 mL/min.

The activity (LIPU/g) of the enzyme is calculated using the following:

$$LIPU/g = \frac{ml/min. \times N \times 1000 \times F \times \text{factor for tributyrin}}{A \times 2}$$

ml/min.: Slope of titration curve
N: Normality of NaOH
F: Dilution of sample
A: Gram sample weighed
2: ml sample 2. Lipase Assay at pH 3.5

1 LPLU (low pH lipase unit) is defined as the quantity of enzyme that produces 1 microequivalent of free fatty acid per min under the conditions described herein below.

Trioctanoate substrate: 0.15% Trioctanoate glycerol, 13% Triton X-100, 0.3% NaCl, and 120 mM Glycine-HCl, pH 3.5. The substrates were prepared by mixing all components followed by stifling for one hour.

The enzyme sample solution is diluted in 50 mM Glycine-HCl, pH 3.5

The assay is carried out using a Konelab analysis robot (Thermo, Vantaa, Finland). 50 μl trioctanoate substrate is equilibrated at 30° C. for 3 min before mixed with 10 μl enzyme sample solution, and incubation for 6 min at 30° C. Free fatty acid in the reaction mixture was measured using the NEFA-HR(2) kit (WAKO Chemicals GmbH). 110 μl NEFA reagent R1 is added to the reaction mixture and incubated for 3 min at 30° C. before 55 μl NEFA reagent R2 is added. Incubation is continued for another 4.5 min at 30° C. before $OD_{520 \text{ nm}}$ is measured. The content of free fatty acid is calculated from a standard curve prepared from NEFA Standard (WAKO Chemicals GmbH).

1 LPLU corresponds to 0.24 LIPU for *Aspergillus tubingensis* lipase (FIG. 5, SEQ ID No. 7).

2. Phytase Assay.

As used herein 1 FTU (phytase unit) is defined as the amount of enzyme required to release 1 μmol of inorganic orthophosphate from a substrate in one minute under the reaction conditions defined herein Principle:

The Phytase is incubated with Sodium phytate, which results in the release of in-organic Phosphate. The in-organic Phosphate creates coloured complexes with the Molybdate-Vanadate reagent, which hereby turns yellow. The yellow colour of the complex is measured on the spectrophotometer at 415 nm.

Quantification of activity is made by an absolute method using a phosphate standard curve.

Reagents:

1.1 Acetate buffer (pH 5.5) 0.25 M 1000 mL
Dissolve:
30.02 g Sodiumacetate—Trihydrate (18.10 g sodiumacetate—Anhydrate),
0.147 g Calcium chloride—Dihydrate,
1.76 g 100% Acetic acid (=1.677 mL, density=1.0498 g/mL) in app. 900 mL water, Adjust pH to 5.5 with 4 M Acetic acid (22.9 mL concentrated Acetic acid in 100.0 mL deionised water) and transfer the solution to a 1000 mL volumetric flask.

Add 1 mL 10% Tween 20 and adjust the solution to 1000 mL by addition of deionised water.

1.2 Potassium Dihydrogen Phosphate 18 mM 1000 mL
Stock solution used for standard curve
Dry $KH_2PO_4$ at 60° C. overnight in a heating cupboard.
Weigh 2.45 g dry $KH_2PO_4$ and dilute in Acetate buffer (1.1). Adjust to 1000.0 mL.

1.3 Phytate Solution (Substrate) 7.5 mM 250 mL
Dissolve:
2.10 g (±0.05 g) Sodium phytate, deca hydrate (Phytic acid) in 200 mL Acetate buffer.
Thermostat the solution to 37° C. in a water bath.
At 37° C. pH is adjusted to pH 5.5 by addition of 4 M Acetic acid (24 g=22.9 mL concentrated Acetic acid in 100.0 mL deionised water).
Adjust to 250.0 mL by addition of Acetate buffer.
A substrate correction factor may be needed when changing to another lot of phytic acid.
Correction factor for phytic acid Sigma P0109, batch 057K0049 is defined to 1.00

1.4 Nitric Acid Solution 24.5% 200 mL
(For Ammonium Vanadate Solution)
75 mL Nitric acid (65%) is added to 100 mL water under continuous stirring.
The solution is transferred to a 200 mL volumetric flask and adjusted with deionised water.

1.5 Ammonium Solution 25% 50 mL
(For Ammonium Heptamolybdate Solution)
40 mL of a 32% Ammonium solution is adjusted to 50 mL with water.

1.6 Ammonium Heptamolybdate Solution 10% 250 mL
(For Colour/Stop Reagent)
Dissolve:
25 g Ammoniumheptamolybdate—tetrahydrate in 225 mL water. The solution needs to be heated to dissolve the Ammonium Heptamolybdate before adding the Ammonium solution.
Add 2.5 mL Ammonium solution (25%) (see 1.5), turn off the heat and leave on stirrer until totally dissolved.
When cooled the solution is transferred to a 250 mL volumetric flask, adjusted with deionised water and mixed.

1.7 Ammonium Vanadate Solution 0.24% 250 mL
(For Colour/Stop Reagent)
Dissolve 0.5875 g ammonium Vanadate in 100 mL water preheated to 60° C.). Add slowly 5 mL 24.5% Nitric acid solution under continuous stirring. When cooled the solution is transferred to a 250 mL volumetric flask, adjusted with deionised water and mixed.

1.8 Colour/Stop Reagent 200 mL
Should be prepared immediately before use.
Dispense 50 mL Ammonium heptamolybdate solution (10%) in a 200 mL volumetric flask followed by 50 mL of Ammonium Vanadate solution (0.24%). Dispense 33 mL 65% Nitric acid under continuous stirring. Adjust to 200.0 mL by addition of deionised water and mix.

Reaction Conditions pH = 5.5
Incubation temperature = 37° C. ± 0.1° C.
Incubation time = 60 minutes Preparation of a Phosphate Standard Curve (Absolute Method)

A standard curve using the $KH_2PO_4$ buffer (1.2) is prepared. The standard is diluted with Acetate buffer.

$C_{dilution}$=0.0 mM, 0.5 mM, 1.0 mM, 1.5 mM, 2.0 mM, 2.5 mM, 3.0 mM, 4.0 mM

Use the following equation: $C_{stock\ solution} * V_{stock\ solution} = C_{dilution} * V_{dilution}$  $V_{stock\ solution} = (C_{dilution} * V_{dilution})/C_{stock\ solution}$ Where C=concentration and V=volume

| Final Phosphate concentration in mM | volume $KH_2PO_4$ (18 mM) into 50 mL volumetric flask | Volume of Acetate buffer |
| --- | --- | --- |
| 0 | 0.0 Ml | 50.0 mL |
| 0.5 | 1.4 mL | 48.6 mL |
| 1.0 | 2.8 mL | 47.2 mL |
| 1.5 | 4.2 mL | 45.8 mL |
| 2.0 | 5.6 mL | 44.4 mL |
| 2.5 | 6.9 mL | 43.1 mL |
| 3.0 | 8.3 mL | 41.7 mL |
| 4.0 | 11.1 mL | 38.9 mL |

1.00 mL of standard curve sample is mixed with 2.00 mL Colour/Stop reagent followed by 2.00 mL Phytate solution. The samples are incubated at room temperature for 5-10 minutes, and OD measured (as done with the samples after incubation).

Sample Preparation:

1A: Liquid products (app. 5500 FTU/g): 1 g of sample is weighed in a 100 ml volumetric flask, the weight is written down, and the volumetric flask is filled up with Acetate buffer.

1B: Dry products (phytase formulated on wheat/starch carrier only): 1 g of product is weighed into a glass beaker. 100 mL of Acetate buffer is added by using a dispenser or measuring glass. The sample is stirred on a magnetic stirrer for 20 minutes. The extract is filtered through a glass filter.

1C: Dry products (coated granules with a hydrophobic outer layer): Dry products: 1 g of product is weighed into a glass beaker. 100 mL of Acetate buffer is added by using a dispenser or measuring glass. The sample is stirred on a magnetic stirrer for 20 minutes. The extract is left for settling, coated product must not be filtered through a glass filter.

2: Prepare the further dilution of the sample. Preferred OD range is 0.4-1.6. If the concentration of the sample is not known, typical dilutions levels to bring the activity into the range for the assay are shown below.

The activity in the samples should be approximately 0.0300 U/mL.

The dilutions should be prepared immediately before determination.

Determination of Activity:

All samples are analysed at the same time—controls, blanks and samples. The assay run must be in a continuous flow.

All determinations are made as double or triple determinations.

A blank is included in the beginning of each series.

A control is included in each series of tubes (Phytase control or Phyzyme XP sample of known activity).

Blind samples: 1.00 mL of each sample is mixed with 2.00 mL Colour/Stop reagent followed by 2.00 mL Phytate solution. The samples are incubated at room temperature for 60 minutes, centrifuged and measured with the rest of the samples.

Samples:
1. Draw 1.00 mL of diluted sample or control 2 or 3 times in plastic tubes. For blanks draw 1.00 mL of Acetate buffer.
2. Place the Phytate solution (substrate) in a water bath at 37.0° C. for a minimum of 5 minutes until equilibrated to 37° C. 3.
3. Incubate the samples in the water bath at 37.0° C. for exactly 5 minutes.
4. Add 2.00 mL of equilibrated Phytate solution to the samples with a time interval of exactly 5 seconds.
5. Incubate in the water bath at 37.0° C. for exactly 60 minutes.
6. Add 2.00 mL Colour/Stop reagent, again with a time interval of 5 seconds, put on a lid and turn upside down 5 times.
7. Centrifuge for 10 min. at 3500 rpm.
8. Measure at 415 nm. Adjust the spectrophotometer to zero with demineralized water.

Calculation of Activity

OD of the blank has to be $\leq 0.13$; if not the analysis has to be repeated.

Write the data in an Excel sheet

Make a standard curve and a tendency line in Excel:
a) y-axis=$OD_{415}$
b) x-axis=mM phosphate
c) the slope ($\alpha$) has to be within 0.36-0.38
d) the intercept ($\beta$) must not exceed $|0.02|$
e) the correlation coefficient ($R^2$) should be $\geq 0.99$ The phytase activity is calculated as follows:

$$\text{Activity}(FTU/g) = \frac{((OD_{sample} - OD_{blank}) - \beta) * DF}{\text{Incubation time} * \alpha * W_{sample}}$$

$OD_{sample}$=mean absorbance of enzyme sample
$OD_{blank}$=mean absorbance of enzyme blank
DF=dilution factor for the sample
Incubation time=60 minutes
$W_{sample}$=weight of sample or control
$\alpha$=Slope of the standard curve
$\beta$=Intercept of standard curve Phytase Assay at pH 3.5:

This is identical to the phytase assay at pH 5.5 with the following substitutions:

1.1 Assay Buffer

Glycine-HCL buffer pH 3.5 (used instead of 1.1 Acetate buffer pH 5.5): 250 ml 0.2M glycin is mixed with 130 mL 0.2M HCl and app. 500 mL deionised water. pH is adjusted to 3.5 with 0.5 M HCl or 0.5 M NaOH. Transfer the solution to a 1000 mL volumetric flask and adjust the solution to 1000 mL by addition of deionised water 1.3 Phytate Solution (Substrate) 7.5 mM (in Total 250 ml):

Dissolve 2.10 g (±0.05 g) Sodium phytate, deca hydrate (Phytic acid) in 200 mL assay buffer (Glycin HCl buffer pH 3.5).

Thermostate the solution to 37° C. in a water bath.

At 37° C. pH is adjusted to pH 3.5 by addition of 4 M HCl or 4 M NaOH.

Adjust to 250.0 mL by addition of assay buffer (pH 3.5). The bottle containing the solution needs to be wrapped in foil.

Shelf life: two weeks

A substrate correction factor may be needed when changing to another lot of phytic acid.

Correction factor for phytic acid batch 128H1234 (Sigma P-3168) is defined to 1.00

All dilutions of enzymes and phosphate in the method are done with Glycine-HCl assay buffer pH 3.5 instead of Acetate buffer pH 5.5

EXAMPLES

Example 1

Introduction

To be efficient as an enzyme additive to food or animal feed, the phytase has to combine a number of different properties. In order to be able to degrade phytic acid in the acidic environment of an animal's stomach it has to be active at low pH, preferably over a broad range of pH values. In addition, it has to have high specific activity and preferably high thermostability to enable the protein to withstand high temperatures commonly used in preparation of feedstuffs such as feed pellets.

It is also important that the enzyme has broad substrate specificity allowing it to hydrolyse not only phytate but also intermediate products of phytate degradation such as inositol pentaphosphates, tetraphosphates and triphosphates. Studies on phytate degradation in pigs show that these inositol oligophosphates otherwise remain largely insoluble in the small and large intestine and thus inaccessible to alkaline phosphatases produced by the animal and gut microflora. Variations in substrate specificity profiles of different enzymes have been identified. For example, inositol-triphosphates generated by the phytase from *B. subtilis* are essentially resistant to further hydrolysis by this enzyme.

Suitably these variants show improved characteristics with respect to any one of the following: temperature stability, pH range, pepsin stability, specific activity, substrate specificity, and broader substrate specificity. Suitable methods for determining these characteristics are disclosed herein.

In particular, the improvements in phytase characteristics are directed to the enzyme stability under food and feed processing conditions, to the enzyme stability during stomach transit, and to the enzyme activity and stability in human or animal stomach and/or intestinal tract making the improved variants particularly suitable for use as feed supplements. Thus, such improvements comprise among other parameters the increase in stability at elevated temperatures, preferably at temperatures above 65° C., the increase in stability against proteolytic digestion, preferably protease of the digestive tract such as pepsin, the increase in catalytic activity at low pH, preferably catalytic activity below pH 5.5, and the general efficiency of releasing phosphate groups from phytate, and preferably in addition inositol phosphates.

Improvements in phytase characteristics are directed to the use in food and feed processing as well as for the use as an additive to food and feed products. In particular, improvements are directed to the stability under food and feed processing conditions, to the stability during stomach transit, and to the activity and stability in human or animal stomach and/or intestinal tract. Such improvements comprise among other parameters the increase in stability at elevated temperatures, preferably at temperatures above 65° C., the increase in stability against proteolytic digestion, preferably protease of the digestive tract, the increase in catalytic activity at low pH, preferably catalytic activity below pH 5.5, and the general efficiency of releasing phosphate groups from phytate.

The increase in stability at elevated temperatures is quantified by the inactivation temperature of the enzyme. The inactivation temperature is defined as the temperature at which the residual activity of a phytase enzyme after incubation for a certain duration and subsequent cooling to room temperature is 50% of the residual activity of the same phytase enzyme incubated for the same duration under the same conditions at room temperature. Thermostability differences are the differences in ° C. between the inactivation temperatures of two enzymes.

Example 2

Pepsin Stability

Pepsin resistance at pH 2 of phytases from *Buttiauxella*, variants BP-17, BP-110, BP-111, BP-112, and Phyzyme XP compared to Natuphos (BASF), and Ronozyme P (Novozymes/DSM).

Materials and Methods

Buffers:

Pepsin incubation buffer: 0.1 M Glycine-HCl, pH 2.0, 3 mg/ml BSA, 2.9 mg Sodium chloride anhydrous/mL, 0.73 mg calcium chloride/mL. For solutions with pepsin, the incubation buffer is prepared to contain 500, 1000, 3000, 6000, or 10000 U/ml of pepsin (Sigma P-7000, 10000 U/mg corresponds to 27 mg/ml), respectively. One pepsin unit is defined as the amount of enzyme that will produce a $\Delta OD_{280}$ of 0.001 per min at pH 2.0 at 37° C., measured as TCA-soluble products using haemoglobin as substrate (Food Chemical Codex).

Phytase assay buffer: Acetate buffer 250 mM, pH 5.5

Phytase assay buffer with BSA: Acetate buffer 250 mM, pH 5.5, with 3 mg/ml BSA

Resistance Against Increasing Pepsin Concentration:

The set-ups for an enzymes were the same: Six samples with enzyme were prepared (in duplicate): Four samples with increasing amount of pepsin in buffer (pH 2), one sample without pepsin but in incubation buffer (pH 2), and one positive control sample with enzyme in assay buffer with BSA (pH 5.5).

For each sample, 900 µl incubation buffer without or with increasing amounts of pepsin or 900 µl assay buffer were mixed with 100 µl enzyme solution followed by incubation at 40° C. After 120 min incubation, 100 µl was withdrawn and mixed with 900 µl assay buffer. Samples were immediately analysed for phytase at pH 5.5 against phosphate standard curve as described by ISO draft international standard ISO/DIS 30024.

Results

Pepsin Resistance

The *Buttiauxella* variants an showed excellent stability towards pepsin at pH 2. In contrast, the activity of Natuphos was reduced dramatically already at a pepsin concentration of 500 U/ml, with further reduced activity finding a plateau of about 45% recovery at a pepsin concentration 3000 U/ml. The recovery of Ronozyme P was even worse with a reduction in recovery of less than 20% at a pepsin concentration of only 500 U/mg (FIG. 9A).

FIG. 9 shows the resistance of the phytases originating from *Buttiauxella*, variants BP-17, BP-110, BP-111, and BP-112, and of Phyzyme XP, Natuphos, and Ronozyme P against increasing concentrations of pepsin. Data are relative to incubation at pH 2 without pepsin. A: all data points, B: same data but showing only more than 70% recovery.

TABLE 1

| Same data as presented in FIG. 9 | | | | | | | |
|---|---|---|---|---|---|---|---|
| Pepsin level | BP-17 | BP-17 v. 110 | BP-17 v. 111 | BP-17 v. 112 | Phyzyme XP | Natuphos | Ronozyme P, new |
| 0 | 100% | 100% | 100% | 100% | 100% | 100% | 100% |
| 500 | 87% | 96% | 98% | 85% | | 61% | 19% |
| 1000 | 81% | 98% | 96% | 85% | | 51% | 16% |
| 3000 | 82% | 96% | 94% | 84% | 93% | 44% | 17% |
| 6000 | 82% | 92% | 89% | 80% | 89% | 45% | 18% |
| 10000 | 86% | 95% | 94% | 79% | 98% | 46% | 21% |

There are slight differences between the *Buttiauxella* variants, where variant BP-17 var.110 shows best stability having 95% activity left after two hours of incubation at the highest pepsin concentration, 10000 U/mL (FIG. 9B). In comparison, BP-17 showed a recovery of around 85% after two hours of incubation.

The *Buttiauxella* phytases also showed excellent acid stability. Comparing the activity measured at pH 5.5 after two hours of incubation at either pH 2 or pH 5.5 showed that all four *Buttiauxella* phytases did not lose activity during the 2 hours incubation at pH 2 whereas Phyzyme XP, Natuphos, and the new Ronozyme P showed slight to significant reduction in activity (Table 2).

TABLE 2

| The activity measured at pH 5.5 after incubation in a buffer at pH 2 or pH 5.5 for two hours. | | | | | | | |
|---|---|---|---|---|---|---|---|
| | BP-17 | BP-17 v. 110 | BP-17 v. 111 | BP-17 v. 112 | Phyzyme XP | Natuphos | Ronozyme P, new |
| Assay buffer | 100% | 100% | 100% | 100% | 100% | 100% | 100% |
| pH 2, no pepsin | 101% | 102% | 106% | 120% | 83% | 90% | 67% |

The numbers are relative to the activity from the samples incubated at pH 5.5.

Data Summary

The *Buttiauxella* phytase variants according to the present invention show more than 75% recovery after 2 hours of incubation at pH 2, 37° C., 10000 U/ml of pepsin compared to activity of the sample incubated under the same condition but without pepsin present.

Example 3

Recovery of Enzyme Activity

Evaluation of Recovery of Enzyme Activity
Materials and Methods

Here, we evaluate the recovery of enzyme activity after pelleting of the wheat formulated enzyme. The enzyme is sprayed on granulated wheat and dried prior to mixing with feed followed by the pelleting process.

Figure 10:
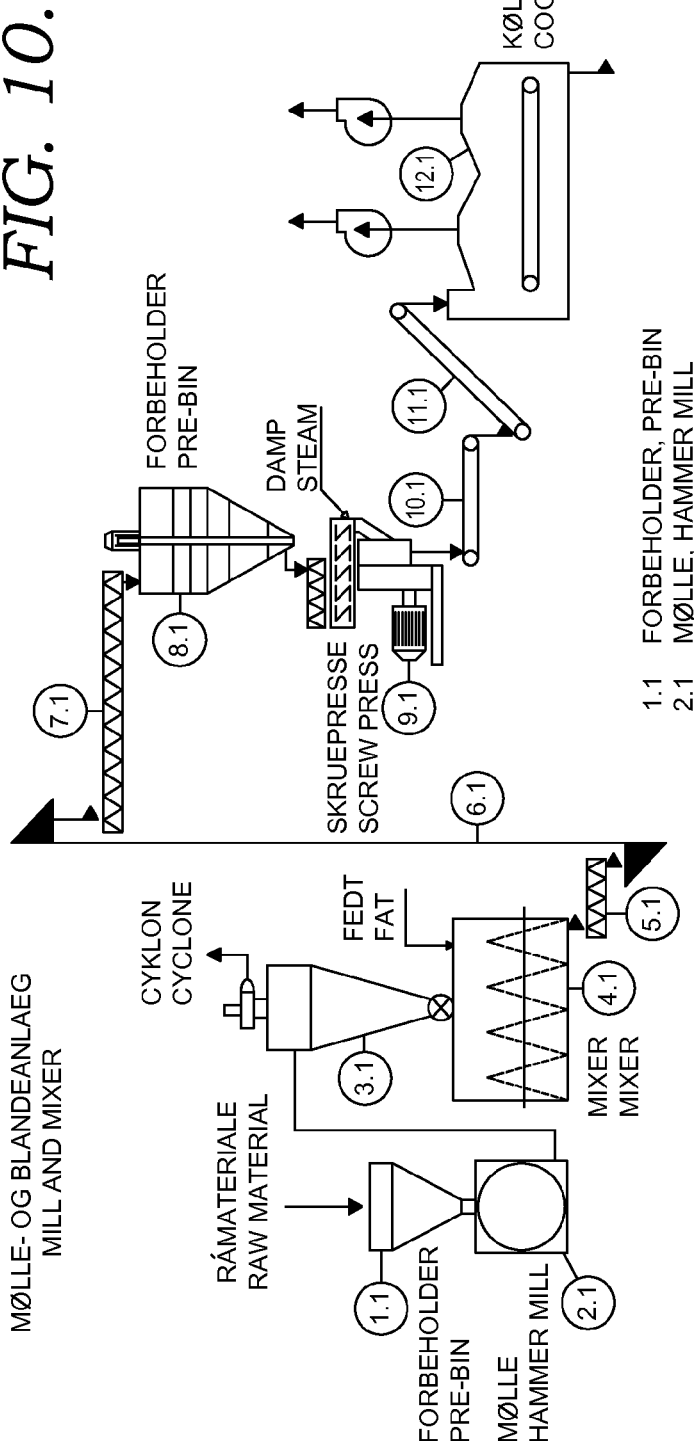
FIG. 10 shows a schematic representation of the pelleting unit at the Technological Institute in Kolding.

Liquid enzymes where formulated on whole grounded wheat and dried to a dry matter content on approximately 90%. The inactivation of enzymes during thermal stress in the pelleting process was tested using a pelleting unit at the Technological Institute in Kolding (schematically presented in FIG. 10). Test sample is added to 10 kg premix and mixed for 10 min. Then 10 kg premix was added to 150 kg feed (large horizontal mixer) and mixed for 15 min. before conditioning/steaming. Feed is treated 30 sec. at 90° C./95° C. before pelleting. The temperature is measured in the outlet of the cascade mixer. Immediately after leaving the pelleting press the pellets are cooled to room temperature.

Phytase activity was measured according to the methodology recited herein.

Phytase activity is 5 units per gm in the mash feed prior to pelletising.

Results

Figure 11:
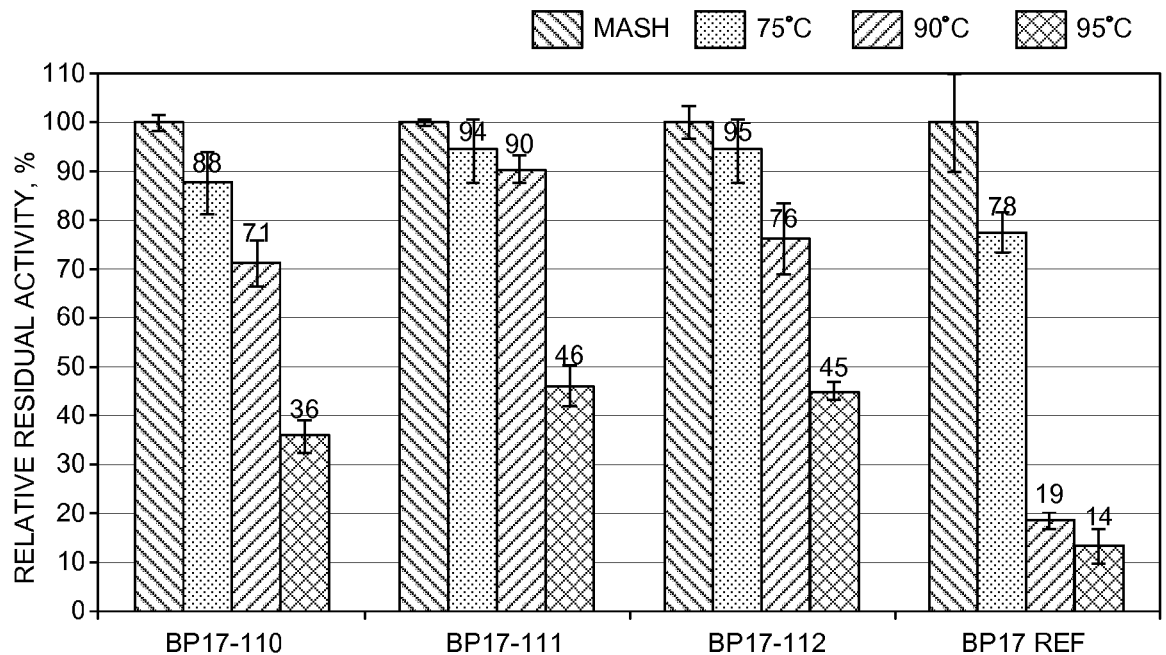
FIG. 11 shows the relative residual activity from pelleting trials of three Phytase B variants for use in the present invention.
Figure 12:
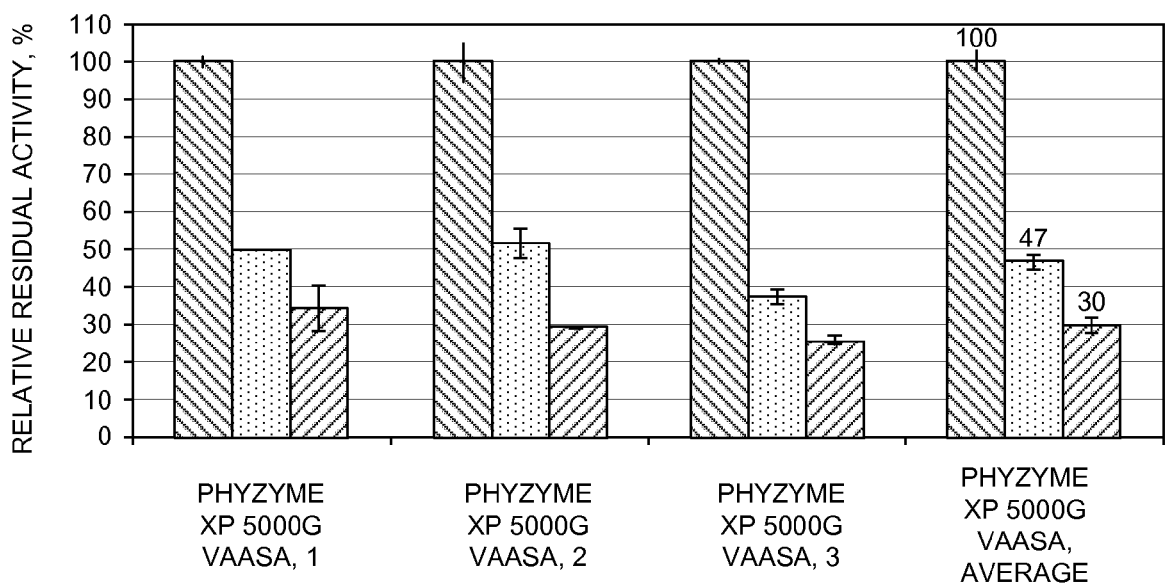
FIG. 12 shows the relative residual activity when Phyzyme XP, an *E coli* phytase is formulated on whole grounded wheat.
Figure 13:
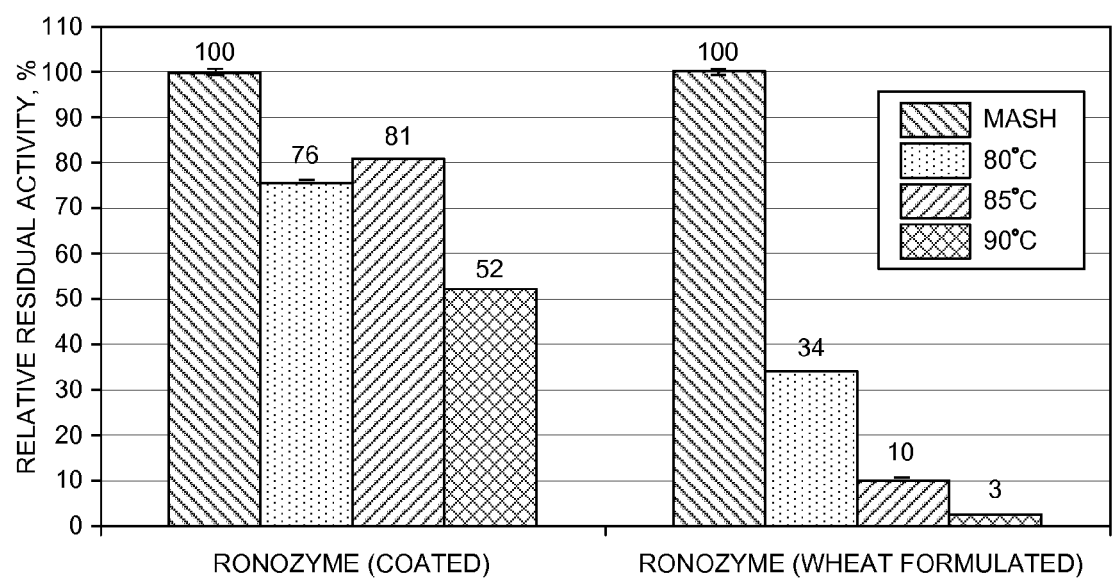
FIG. 13 shoes the results of a trial in which the phytase was extracted from the coated Ronozyme product and formulated on whole grounded wheat to study the themostability of the phytase molecule without protection.

The results are presented in FIGS. 11 to 13.

In FIG. 11, the results from the pelleting trials of three Phytase B variants according to the present invention is disclosed. The enzymes were formulated on whole grounded wheat and dried to app 10% water content. Here, the recovery of phytase activity after pelleting for BP 17 var 111 is 90% at 90° C. compared to a recovery of 19% at 90° C. for the BP 17.

As reference the Phyzyme XP, an *E coli* phytase was formulated on whole grounded wheat. The results are shown in FIG. 12. Here, the recovery of phytase activity after being pelletised at 90° C. from the three batches of Phyzyme XP formulated on whole grounded wheat is 47%.

Ronozyme was also tested. The product is sold in a coated version, to protect the enzyme from the heat in the pelleting process. In this trial the phytase was extracted from the coated product and formulated on whole grounded wheat to study the themostability of the phytase molecule without protection. The results are shown in FIG. 13.

Data Summary

The *Buttiauxella* phytase variants of the present invention formulated on wheat show more than 70% recovery after being pelleted at 90° C.

Example 4

Phytic Acid Degradation

Results from a Study of Phytic Acid Degradation by Phytase Solutions

Three different buffers were used in the incubations. They were as follows:
250 mM acetate pH 5.5;
250 mM Acetate M pH 3.5; and
250 mM HCl glycine pH 2.5.

All phytases used on the incubations were diluted in assay buffer to enzyme level at 1 U/ml.

The phytate substrate solution used in the incubation is a Phytate 1% (1 g/100 ml buffer).

The substrate is prepared in same buffer as used for the dilution of phytases to keep the pH level constant in the reaction.

The reaction is terminated by 1M HCl.

Incubation

The incubation volumes are: 1.5 or 3.0 ml Phytate+0.25 ml enzyme+3.25 or 1.75 ml buffer at 37° C., a total volume of 5.0 ml.

Sub-samples of 0.5 ml are taken at different time points (0, 30, 60 and 90 min).

An eppendorf tube is prepared with a 0.2 ml 1M HCl for each sub-sample prior to the sub-sampling. By blending the sub-sample from the incubation with HCl the enzyme reaction is terminated. Each sub-sample of 0.7 ml is stored at 4° C. until HPLC analysis.

HPLC Method

Analysis of phytate and inositol isomers by high performance ion chromatography (HPIC). This method has been described by Skoglund and Carlsson et al. (*J. Agric. Food Chem.*, 45 (1997), 451-436 5. *J. Agric. Food Chem.*, 46 (1998), 1877-1882; and *J. Agric. Food Chem.*, 49 (2001), 11695-1701. The column used was a strong anion exchanger (4×250 mm) from Dionex with a pre-column of 4×50 mm. Solvent A, MilliQ water, Solvent B, 1N HCl prepared in water. The gradient is from 2.5% to 49% B in 30 min followed by 3 min of isocratic at 50% and 2 min isocratic at 2.5% at a flow of 0.8 ml/min. Each run is 35 min. It is possible to reduce the run to totally 25 min as phytase does not produce so many theoretically possible IP isomers. The eluent was in-line derivatized with a water solution containing 0.1% Fe$(NO_3)_3.9HO_2$ and 2% perchloric acid ($HClO_4$) at a flow of 0.4 ml/min. Phytate and IP isomers were detected at 290 nm as a positive peak. This is due to the formation of phytate-$Fe^{3+}$—$ClO_4^-$ complex. A perchloric acid solution of 60% was bought from Sigma.

Results

The results are presented in FIGS. 14-17.

Data Summary

All of the enzymes of the present invention display favourable characteristics.

The phytases of the present invention break down phytate at all of the tested pH levels.

The enzymes of the present invention are very active at pH 5.5.

BP 110 and BP 111 display similar activity at pH 2.5 and 3.5.

BP 110 and BP 111 break down all the phytate added to the incubations after 90 min at both pH 2.5 and pH 3.5

BP 112 breaks down 75% of the phytate added to the incubations after 90 min at both pH 2.5 and pH 3.5

Figure 14:
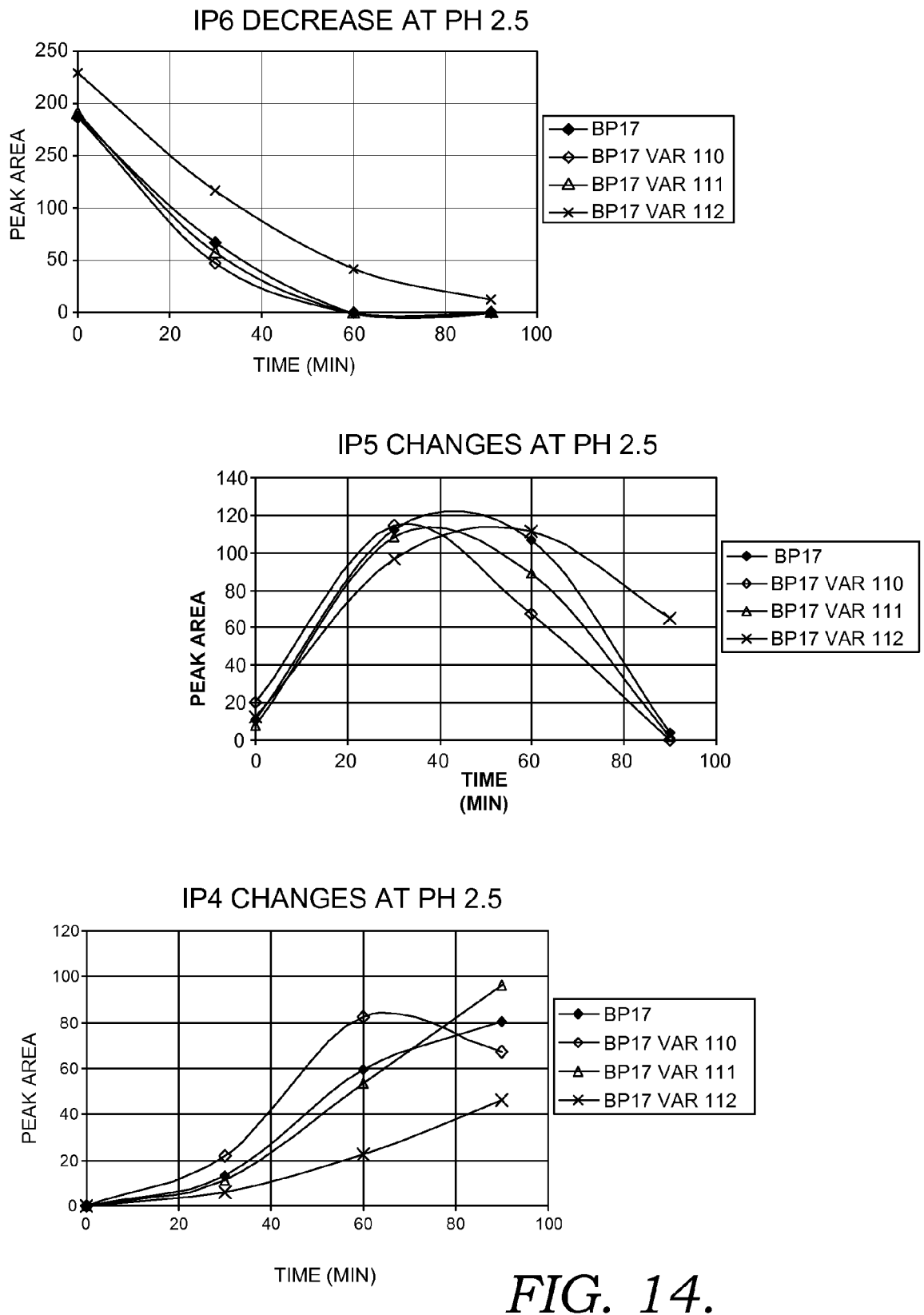
Figure 15:
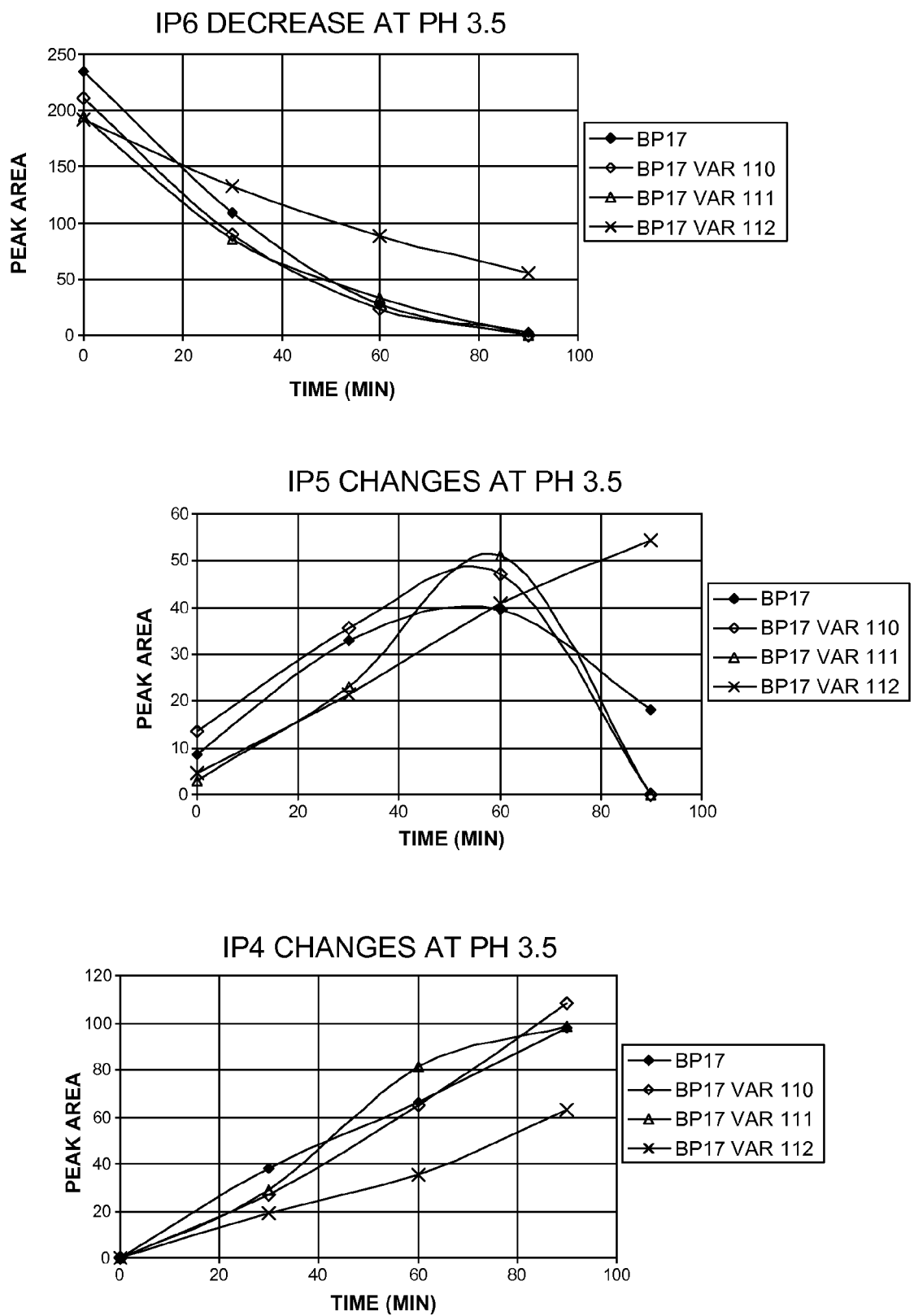

The enzymes of the present invention display better characteristics than Ronozyme and Natuphos at pH 2.5 (see at least FIG. 17) (Enzyme concentration is higher than seen in FIGS. 14-16, so *Buttiauxella* BP17 is there as reference.)

Example 5

Phytic Acid Hydrolysis in a Liquefact

Phytic Acid Determination:

Phytic acid content: Phytic acid was extracted from a sample by adjusting the pH of the 5% slurry (if it is dry sample) to pH 10 and then determined by an HPLC method using an ion exchange column. Phytic acid was eluted from the column using a NaOH gradient system. Phytic acid content in the liquid was then calculated by comparing to a phytic acid standard.

Results

Figure 18:
FIGS. 18 and 19 are HPLC chromatograms which clearly show that phytase from *Buttiauxella* variants catalyzed the hydrolysis of phytic acid at temperature greater than 85° C.
Figure 19:
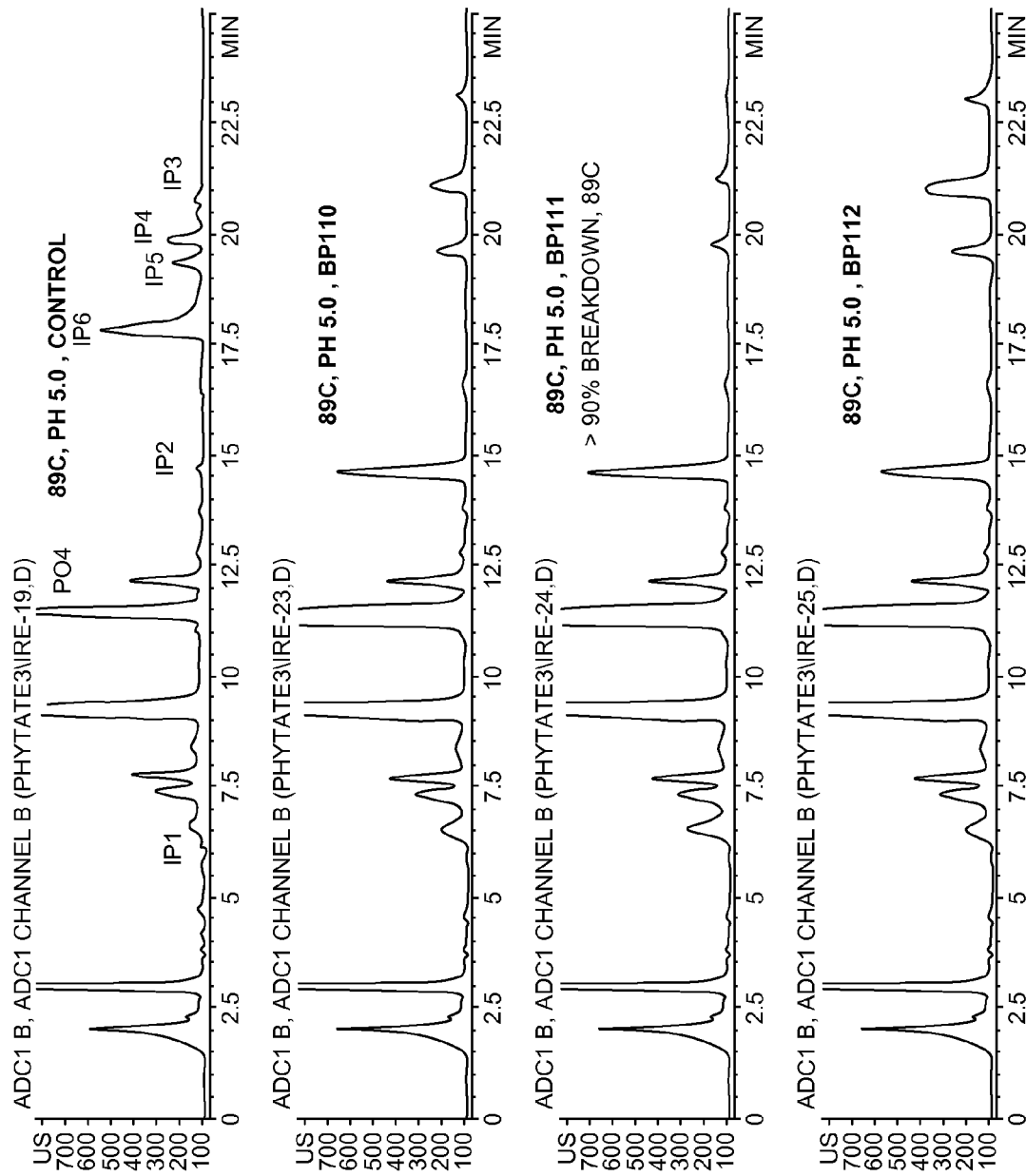

The effect of temperature on the hydrolysis of phytic acid of the whole ground corn liquefact from a conventional dry grind liquefaction process (source: Illinois River Energy, Monroe, Ill.) by different thermostable BP variant phytase, i.e., BP110, BP111 and BP112 was studied. The pH of a 32% ds ("dry solid") whole ground corn ds corn liquefact was adjusted to pH 5.0 and placed in a water bath maintained at 85° C. and 89° C. After temperature equilibration, BP-phytase was added at 4.0 FTU/gds. corn. Samples were then taken at 20 minutes and the enzyme reaction was terminated by the addition of 10 mM sodium hydroxide (diluted 1 to 10 fold). The diluted samples were then filtered and analyzed by HPLC for their phytate derivatives profile (IP1 to IP6). The HPLC chromatograms in FIGS. 18 and 19 clearly showed that phytase from all three variants catalyzed the hydrolysis of phytic acid at temperature greater than 85° C. The phytic acid content (phytic acid (IP6) and intermediates IP1 to IP5) in whole ground corn liquefact is around 1.7% ds.corn and data in FIG. 18 showed that more than 95% of the phytic acid was hydrolyzed by thermostable phytase under the current liquefaction conditions. Significantly, the HPLC profile from the samples incubated at 89° C. showed that the BP-111 phytase variant exhibited higher thermostability compared to phytase from two other variants (see FIG. 19; BP-110 and BP-112).

Example 6

Expression of the *Aspergillus tubingensis* Lipase 3 in *Trichoderma reesei*

Figure 20:
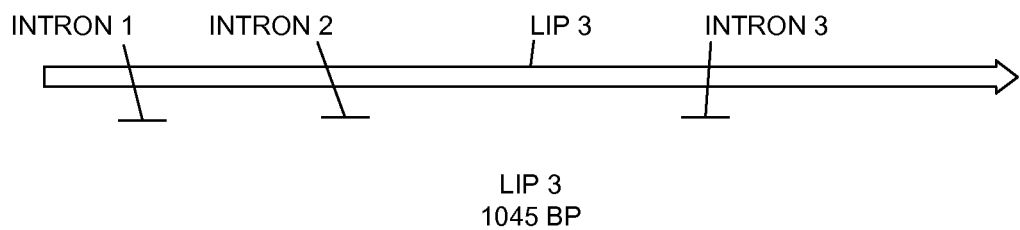
FIG. 20 shows the pDONR221::lip 3 containing the *Aspergillus tubingensis* lipase 3 genomic DNA.
Figure 21:
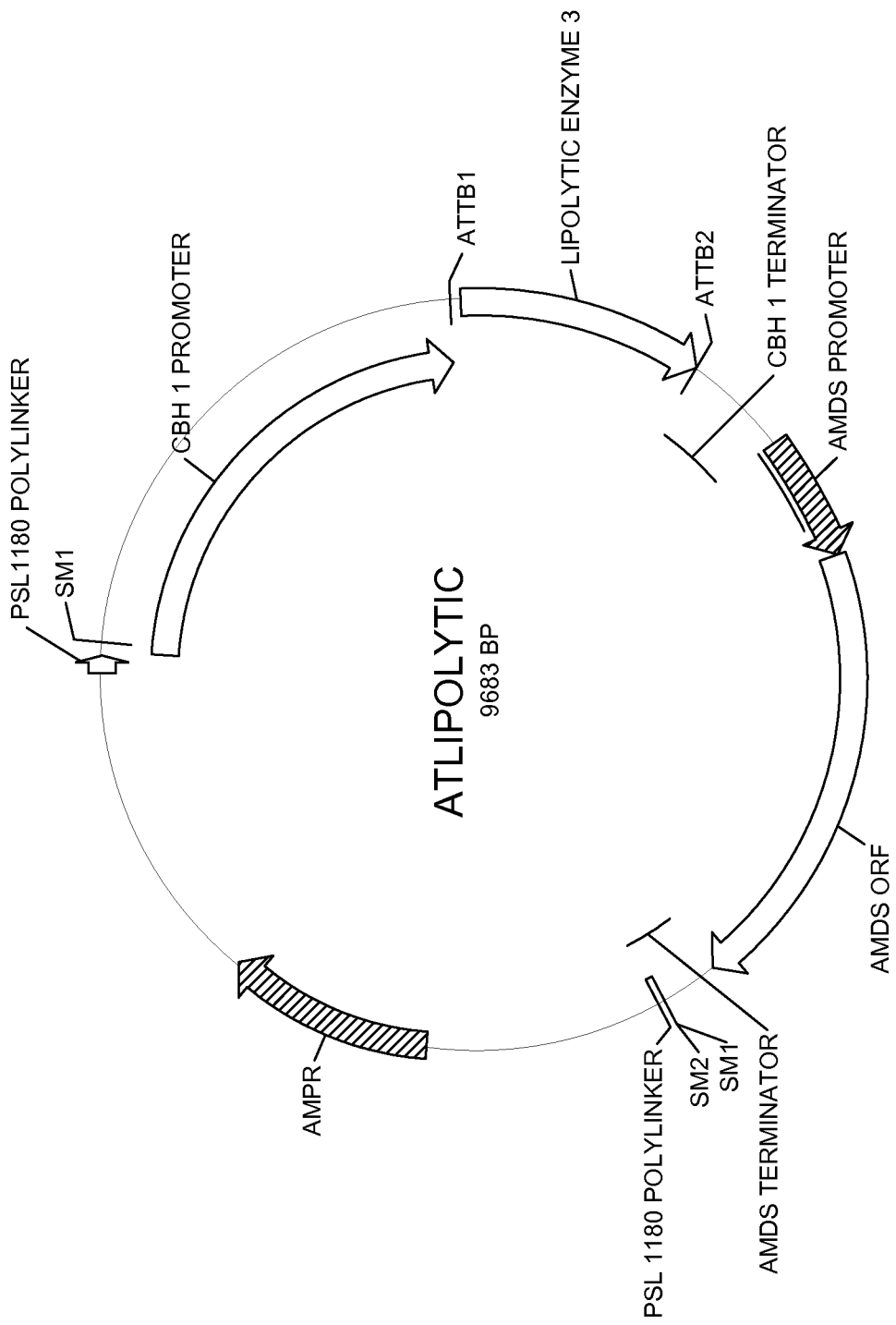
FIG. 21 shows the final lipase expression construct ATlipase3Trex.

1. Expression Construct & Strain Used for Transformation pDONR™221 plasmid DNA obtained from Invitrogen (catalogue no. 12536-017) was used as the donor vector. pDONR221::lip 3 containing the *Aspergillus tubingensis* lipase 3 genomic DNA (FIG. 20) was recombined into the *T. reesei* gateway destination vector pTrex3G (described in detail in WO 05/001036), resulting in the final expression construct ATlipase3Trex (FIG. 21).

The expression cassette contained the promoter and terminator regions of the *T. reesei* cellobiohydrolase 1 (cbh1) gene. It also contained the *Aspergillus nidulans* acetamidase, amdS gene as a selectable marker for transformation of *T. reesei*.

The *Aspergillus tubingensis* lipase 3 genomic DNA encodes a lipase 3 lipolytic enzyme having the amino acid sequence shown in SEQ ID No. 7.

The term "lipase 3" when used herein refers to a lipolytic enzyme comprising the amino acid sequence shown in SEQ ID No. 8, such as the amino acid sequence shown in SEQ ID No. 7. Seq. ID No. 7 contains the signal seq and seq. ID No. 8 is the mature lipase protein without the signal sequence.

The strain used for transformation was *Trichoderma reesei*, a derivative of the non-GMM strain RL-P37 from which the genes encoding the two secreted cellobiohydrolases, CBHI and CBHII, and two of the secreted endoglucanases, EGI and EGII, have been deleted.

The Expression Vector pTrex3g.

The following describes the construction of the vector pTrex3g which may be used to express the genes of the present invention.

This vector is based on the *E. coli* vector pSL1180 (Pharmacia Inc., Piscataway, N.J., USA) which is a pUC118 phagemid based vector (Brosius, J. (1989) DNA 8:759) with an extended multiple cloning site containing 64 hexamer restriction enzyme recognition sequences. It was designed as a Gateway destination vector (Hartley, J. L., Temple, G. F. and Brasch, M. A. (2000) Genome Research 10:1788-1795) to allow insertion using Gateway technology (Invitrogen) of any desired open reading frame between the promoter and terminator regions of the *T. reesei* cbh1 gene. It also contains the *Aspergillus nidulans* amdS gene for use as a selectable marker in transformation of *T. reesei*.

The details of pTrex3g are as follows. The vector is 10.3 kb in size.

Inserted into the polylinker region of pSL1180 are the following segments of DNA:
1. A 2.2 bp segment of DNA from the promoter region of the *T reesei* cbh1 gene
2. The 1.7 kb Gateway reading frame A cassette acquired from Invitrogen that includes the attR1 and attR2 recombination sites at either end flanking the chloramphenicol resistance gene (CmR) and the ccdB gene
3. A 336 bp segment of DNA from the terminator region of the *T. reesei* cbh1 gene
4. A 2.7 kb fragment of DNA containing the *Aspergillus nidulans* amdS gene with its native promoter and terminator regions.

2. Transformation of *T. reesei* Quad Delete Host Strain

The expression construct, ATlipase3Trex, containing the *A. tubingensis* lipase 3 gene was transformed into a *T. reesei* strain using electroporation or biolistic transformation by particle bombardment using the PDS-1000 Helium system (BioRad Cat. No. 165-02257). PCR products containing only fungal DNA or the entire expression plasmid were used for generating transformants by biolistic transformation and electroporation.

A. Transformation by Electroporation

The *T. reesei* host strain to be transformed was grown to full sporulation on PDA plates for 5 days. Spores from 2 plates were harvested with 1.2M sorbitol and filtered through miracloth to get rid of the agar. Spores were transferred to a 50 ml falcon tube and washed by repeated centrifugation 5-6 times with 50 ml water. The spores were resuspended in a small volume (less than 2× pellet volume) using 1.2M sorbitol solution. The spore suspension was then kept on ice. 90 ul of spore suspension was aliqouted into the electroporation cuvette (E-shot, 0.1 cm standard electroporation cuvette from Invitrogen). 10-20 ul DNA construct (plasmid FIG. 4 or PCR product) were added to the spore suspension and electroporation was set at 16 kV/cm, 25 µF, 50Ω. After electroporation, the spore suspension was left on ice, resuspended in 5 parts 1.0M sorbitol and 1 part YEPD, and allowed to germinate by incubation at 28 C with shaking 250 rpm overnight. The next day, the germlings were plated in agar plates containing acetamide. Transformants were picked and transferred individually to acetamide agar plates.

B. Transformation by Particle Bombardment (Biolistic Transformation)

A suspension of spores from a quad deleted strain of *T. reesei* was prepared. 200 ul of spore suspension was spread onto the center of the minimal medium (MM) acetamide plates. (MM acetamide plates had the following composition: 0.6 g/l acetamide; 1.68 g/l CsCl; 20 g/l glucose; 20 g/l KH2PO4, 0.6 g/l CaCl2 2H20; 1 ml/l 1000× trace elements solution; 20 g/l Noble agar, and pH5.5. 1000× trace elements solution contained 5.0 g/l FeSO4 7H2O; 1.6 g/l MnSO4; 1.4 g/l ZnSO4 7H2O and 1.0 g/l CoCl2 6H2O. The spore suspension was allowed to dry on the surface of MM acetamide medium for 1 hour in the sterile hood. Transformation followed the manufacturer's instruction. 60 mg of tungsten particles were placed in a microfuge tube. 1 ml of ethanol was added and allowed to stand for 15 seconds. The ethanol was removed and the particles were washed three times with sterile $dH_2O$ before 250 ul of 50% (v/v) sterile glycerol was added. 25 ul of tungsten particle suspension was placed onto a microfuge tube. While continuously vortexing, the following were added: 5 ul (100-200 ng/ul) of plasmid DNA, 25 ul of 2.5M CaCl2 and 10 ul of 0.1M spermidine. The particles were centrifuged for 3 seconds. The supernatant was removed and the particles were washed with 200 ul of 100% ethanol and centrifuged for 3 seconds. The supernatant was removed. 24 ul 100% ethanol was added and mixed by pipetting, then 8 ul aliquots of particles were removed and placed in the centre of microcarrier disks that were held in a desiccator. Once the tungsten/DNA solution had dried the microcarrier disk was placed in the bombardment chamber along with the plate of MM acetamide with spores and the bombardment process was carried out according to the manufacturer's instructions. After bombardment of the plated spores with the tungsten DNA particles, the plates were incubated at 28° C. Transformed colonies were transferred to fresh plates of MM acetamide medium and incubated at 28° C.

3. Growth of Transformants in Microtiter Plates

After 5 days of growth on MM acetamide plates, transformants obtained by electroporation or by biolistic transformation and displaying stable morphology were inoculated into 200 ul Defined medium with glucose/sophorose in a 96-well microtiter plates. Defined medium with glucose/sophorose (per liter) consists of $NH_4 2SO_4$ 5 g, PIPPS buffer 33 g, Casamino Acids 9 g, $KH_2PO_4$ 4.5 g, $CaCl_2$ (Anhydrous) 1 g, $MgSO_4.7H_2O$ 1 g, pH to 5.50 adjusted with 50% NaOH with milli-Q H2O bring to 966.5 mL. After sterilization, the following were added: Mazu 5 mL, Glucose/Sophrose 60% 26 mL and 400× *T. reesei* Trace Metals 2.5 mL. The microtiter plate was incubated in an oxygen growth chamber at 28° C. for 5 days.

Example 7

The expression host cells suitable for use in the present invention may be a strain of *T. reesei* in which the genes encoding cellobiohydrolase I (CBHI, Cel7a), cellobiohydrolase II (CBHII, Cel6a), endoglucanase I (EGI, Cel7b), and endoglucanase II (EGII, Cel5a) have been inactivated by deletion or disruption using molecular genetic techniques. This strain (a quad delete strain) is useful as a host for overexpression of genes encoding other *T. reesei* secreted proteins.

Preferably host cells suitable for use in the present invention may be derived from a *Trichoderma reesei* cell of the strain RL-P37 using the methods described in WO 2005/001036 and US28026376 A1.

A *T. reesei* strain suitable for use in the present invention may be derived from the publicly available strain of *T. reesei* RL-P37. *T. reesei* strain RL-P37 may be modified to form *T. reesei* strain 1A52 as described in WO 05/001036. *T. reesei* strain 1A52 may be modified as described in US 20080026376 to form a *T. reesei* cell usable in the present invention.

RL-P37 may be modified to form *T. reesei* strain 1A52 as described below.

The *T. reesei* host strain used may be derived from the publicly available strain RL-P37 which has previously been used to manufacture commercial cellulase preparations by Genencor International, Inc. The derivation and characterisation of this strain has been published previously (Sheir-Neiss, G. and Montenecourt, B. S. (1984) Appl. Microbiol. Biotechnol. 20:46-53; U.S. Pat. No. 4,797,361). It is a cellulase over-producing mutant strain which has been obtained as a result of several mutagenesis steps from the wild-type strain (QM6a).

1) Isolation of a pyr4 Mutant Strain.

In order to prepare strain RL-P37 for transformation with plasmid DNA it was necessary to isolate a derivative having a null mutation in the pyr4 gene.

The pyr4 gene encodes orotidine-5'-monophosphate decarboxylase, an enzyme required for the biosynthesis of uridine. The toxic inhibitor 5-fluoroorotic acid (FOA) is incorporated into uridine by wild-type cells and thus poisons the cells. However, cells defective in the pyr4 gene are resistant to this inhibitor but require uridine for growth. It is, therefore, possible to select for pyr4 mutant strains using FOA. In practice, spores of T. reesei strain RL-P37 were spread on the surface of a solidified medium containing 2 mg/ml uridine and 1.2 mg/ml FOA. Spontaneous FOA-resistant colonies appeared within three to four days. FOA-resistant mutants which required uridine for growth were identified. In order to identify those mutants which specifically had a defective pyr4 gene protoplasts were generated and transformed with a plasmid containing a wild-type pyr4 gene (Smith, J. L., Bayliss, F. T. and Ward, M. (1991) Curr. Genet. 19:27-33). Following transformation protoplasts were plated on medium lacking uridine. Subsequent growth of transformed colonies demonstrated complementation of a defective pyr4 gene by the plasmid-borne pyr4 gene. In this way strain GC69 was identified as a pyr4 mutant of strain RL-P37.

2) Construction of a Plasmid Designed to Delete the CBH1 Encoding Gene.

The cbhl gene, encoding the CBHI protein, was cloned from the genomic DNA of strain RL-P37 by hybridization with an oligonucleotide probe designed on the basis of the published sequence for this gene (Shoemaker, S., Schweickart, V., Ladner, M., Gelfand, D., Kwok, S., Myambo, K. and Innis, M. (1983) Biotechnology 1:691-696). The cbhl gene resides on a 6.5 kb Pstl fragment and was inserted into the Pstl site of pUC4K (Pharmacia Inc., Piscataway, N.J., USA) replacing the kanamycin-resistance gene of this vector. The resulting plasmid, pUC4K::cbh1, was then cut with Hind111 and the larger fragment was isolated and religated to give pUC4K::cbh1ΔH/H. This procedure removed the entire cbhl coding sequence and approximately 1.2 kb of 5' and 1.5 kb of 3' flanking sequences. Approximately 1 kb of flanking DNA remained from either end of the original Pstl fragment. The T. reesei pyr4 gene was cloned as a 6.5 kb Hind111 fragment of genomic DNA in pUC18 to form pTpyr2 (Smith, J. L., Bayliss, F. T. and Ward, M. (1991) Curr. Genet. 19:27-33). The plasmid pUC4K::cbh1ΔH/H was cut with Hind111 and the ends were dephosphorylated with calf intestinal alkaline phosphatase. This DNA was ligated with the 6.5 kb Hind111 fragment containing the pyr4 gene to give pΔCBH1pyr4.

Digestion of pΔCBH1pyr4 with EcoR1 liberated a larger fragment which consisted of flanking regions of the cbh1 locus at either end with the pyr4 gene replacing the cbh1 coding sequence in the centre. The only DNA on this fragment which was not derived from T. reesei was a 21 bp fragment derived from the multiple cloning site of pUC4K.

3) Deletion of the cbhl Gene of T. reesei.

Protoplasts isolated from mycelium of strain GC69 were transformed with EcoR1 digested plasmid pΔCBHlpyr4 using methods outlined by Smith et al., 1991. Stable transformants were obtained and those from which the cbh1 gene had been deleted were identified as described below.

Total DNA was isolated from the transformants, digested with Pst1, subjected to agarose gel electrophoresis and blotted to a membrane filter. The filter was then hybridised with $P^{32}$ labelled pΔCBH1pyr4 and the pattern of hybridisation observed by autoradiography. This probe hybridised with the native cbh1 and pyr4 genes in an untransformed strain. In one transformant (strain P37PΔCBHI) a pattern of hybridisation was observed which would be predicted if a double cross-over integration event had occurred. That is, the cbh1 gene had been deleted by integration of a single copy of the larger EcoR1 fragment obtained from pΔCBH1pyr4 at the cbh1 locus of strain RL-P37.

Southern analysis was also performed as above except that the probe used was radiolabelled pintCBHI. This plasmid consists of a pUC vector containing a 2 kb Bglll fragment from the cbh1 locus within the region that was deleted in pUC4K::cbh1ΔH/H. This plasmid hybridised to the cbh1 locus of strain GC69 but did not hybridise to DNA from strain P37PΔCBHI. This confirms that the cbh1 gene had been deleted and that the pUC DNA fragment from pΔCBH1pyr4 had not been incorporated by the deleted strain.

Analysis of secreted proteins by separation on isoelectric focusing gels showed that the CBH1 protein was not produced by strain P37PΔCBHI.

4) Generation of a pyr4 Null Mutant of P37PΔCBHI.

Spores of the transformant (P37PΔCBHI) which was deleted for the cbhl gene were spread onto medium containing FOA. A pyr4 deficient derivative of this transformant was subsequently obtained using the methods described in section above. This pyr4 deficient strain was designated P37PΔCBHIPyr⁻26. Southern analysis has shown that a spontaneous deletion had occurred when strain P37PΔCBHIPyr⁻26 was selected. This deletion completely removed the pyr4 gene which had integrated at the cbh1 locus in strain P37PΔCBHI, as well as flanking DNA from the cbh1 locus beyond the extent of the 6.5 kb Pstl fragment of genomic DNA which was originally cloned.

5) Construction of a Vector Designed to Delete the cbh2 Gene.

The cbh2 gene of T. reesei, encoding the CBH11 protein, has been cloned as a 4.1 kb EcoR1 fragment of genomic DNA (Chen et al., 1987, Biotechnology 5:274-278). This 4.1 kb fragment was inserted between the EcoR1 sites of pUC4XL. The latter plasmid is a pUC derivative (constructed by R. M. Berka, Genencor International Inc.) which contains a multiple cloning site with a symmetrical pattern of restriction endonuclease sites arranged in the order shown here. EcoRI, BamHI, Sac1, Sma1, Hind111, Xho1, Bgl11, Cla1, Bgl11, Xho1, Hind1II, Sma1, Sac1, BamHI, EcoRI. The plasmid, pPΔCBH11 was constructed in which a 1.7 kb central region of this cbh2 clone, between a Hind111 site (at 74 bp 3' of the CBH11 translation initiation site) and a ClaI site (at 265 bp 3' of the last codon of CBHII), has been removed and replaced by a 1.6 kb Hind111-Cla1 DNA fragment containing the T. reesei pyr4 gene obtained as follows. The T. reesei pyr4 gene was excised from pTpyr2 on a 1.6 kb Nhe1-Sph1 fragment and inserted between the Sph1 and Xba1 sites of pUC219 (derived from pUC119 by expanding the multiple cloning site to include restriction sites for Bgl11, Cla1 and Xho1; Wilson et al., 1989, Gene 77:69 78) to create p219M (Smith et al., 1991, Cum Genet. 19:27-33). The pyr4 gene could then be removed as a Hind111-Cla1 fragment having seven by of DNA at one end and six by of DNA at the other endderived from the pUC219 multiple cloning site and inserted into the Hind111 and Cla1 sites of the cbh2 gene to form the plasmid pPΔCBHII.

Digestion of this plasmid with EcoR1 liberated a fragment having 0.7 kb of flanking DNA from the cbh2 locus at one end, 1.7 kb of flanking DNA from the cbh2 locus at the other end and the *T. reesei* pyr4 gene in the middle. The only DNA in this fragment which was not derived from *T. reesei* was the 6 bp and 7 bp fragments of the pUC219 multiple cloning site at either end of the pyr4 gene.

6) Deletion of cbh2 Gene from Strain P37PΔCBHIPyr⁻26

Protoplasts of strain P37PΔCBHIPyr⁻26 were generated and transformed with EcoR1 digested pPΔCBHII according to the methods outlined in 3 above. Stable transformants were cultured in shake flasks and the protein in the culture supernatants was examined by isoelectric focussing. One transformant (designated P37PΔΔCBH67) was identified which did not produce any CBHII (nor CBHI) protein.

DNA was extracted from strain P37PΔΔCBH67, digested with EcoR1 and Asp718, and subjected to agarose gel electrophoresis. The DNA from this gel was blotted to a membrane filter and hybridized with $^{32}$P labelled pPΔCBHII. The 4.1 kb EcoR1 fragment containing the wildtype cbh2 gene was observed in the DNA from an untransformed control strain. In contrast, in strain P37PΔΔCBH67 the single 4.1 kb band was eliminated and replaced by two bands of approximately 0.9 and 3.1 kb. This is the expected pattern if a single copy of the larger EcoR1 fragment from pPΔCBH11 had integrated precisely at the cbh2 locus and deleted the cbh2 gene.

The same DNA samples were also digested with EcoRI and Southern analysis was performed as above. In this example the probe was $^{32}$P labelled plntCBHII. This plasmid contains a portion of the cbh2 gene coding sequence from within that segment of cbh2 DNA which was deleted in plasmid pPΔCBHII. No hybridization was seen with DNA from strain P37PΔCBH67 confirming that the cbh2 gene was deleted and that the pUC plasmid fragment of pPΔCBH1I had not been incorporated by this strain.

7) Selection of a pyr4 Null Mutant of Strain P37PΔΔCBH67.

Spores of the transformant (P37PΔΔCBH67) which was deleted for both the cbh1 and cbh2 genes were spread onto medium containing FOA. A pyr4 deficient derivative of this transformant was subsequently obtained using the methods described in section 1 above. This pyr4 deficient strain was designated P37PΔΔCBH67Pyr⁻1. Southern analysis has shown that a spontaneous deletion had occurred when strain P37PΔΔCBH67Pyr⁻1 was selected. This deletion completely removed the pyr4 gene which had integrated at the cbh2 locus in strain P37PΔCBH67, as well as flanking DNA from the cbh2 locus beyond the extent of the 4.1 kb EcoR1 fragment of genomic DNA which was originally cloned. The short (6 bp and 7 bp) fragments of DNA derived from the pUC219 multiple cloning site which were present at either end of the pyr4 gene would also have been removed from the genome by this deletion.

8) Construction of a Plasmid Designed to Disrupt the egl2 Gene.

The egl2 gene, encoding EG11 (previously referred to as EG111 by some), has been cloned from *T. reesei* and the DNA sequence published (Saloheimo et al., 1988, Gene 63:11-21). We have obtained the gene from strain RL-P37 as an approximately 4 kb Pst1-Xho1 fragment of genomic DNA inserted between the Pst1 and Xho1 sites of pUC219. The *T. reesei* pyr4 gene, present on a 2.7 kb SalI fragment of genomic DNA obtained from pTpyr2, was inserted into a Sal1 site within the EG11 coding sequence to create plasmid pEGII::P-1. This resulted in disruption of the EG11 coding sequence but without deletion of any sequences. The plasmid, pEGII::P-1, can be digested with Hind111 and BamH1 to yield a linear fragment of DNA derived exclusively from *T. reesei* except for 5 bp on one end and 16 bp on the other end both of which are derived from the multiple cloning site of pUC219.

9) Disruption of the egl2 Gene of Strain P37PΔCBH67Pyr⁻1.

Strain P37PΔΔCBH67Pyr⁻1 was transformed with pEGII::P-1 which had been previously digested with Hind111 and BamH1 and stable transformants were selected. Total DNA was isolated from transformants and Southern analysis used to identify strains in which the fragment of plasmid DNA containing the pyr4 and egl2 genes had integrated at the egl2 locus and consequently disrupted the EG11 coding sequence. Southern analysis was performed using as a probe an approximately 4 kb Pstl fragment of *T. reesei* DNA containing the eg12 gene. When DNA isolated from strain P37PΔΔ67P⁻1 was digested with Pstl for Southern analysis the egl2 locus was subsequently visualised as a single 4 kb band on the autoradiograph. However, for a transformant disrupted for the egl2 gene this band was lost and was replaced by two new bands as expected. When the DNA was digested with Bgl11 or EcoRV the size of the band corresponding to the egl2 gene increased in size by approximately 2.7 kb (the size of the inserted pyr4 fragment) between the untransformed P37PΔΔ67P⁻1 strain and the transformant disrupted for egl2. This latter transformant, now deleted for the cbh1, cbh2, and egl2 genes, was designated as strain B31. Further Southern analysis confirmed that the pUC DNA fragment of pEGII::P-1 was not incorporated in this strain.

10) Selection of a pyr4 Null Mutant of Strain B31.

Spores of the transformant (B31) which was deleted for the cbh1, cbh2 and egl2 genes were spread onto medium containing FOA. A pyr4 deficient derivative of this transformant was subsequently obtained using the methods described in section 1 above. This pyr4 deficient strain was designated B31 P6. Southern analysis has shown that a spontaneous deletion had occurred when strain B31P6 was selected. This deletion removed the majority of the pyr4 gene which had integrated at the eg12 locus in strain B31, but did not extend into the flanking DNA of the eg12 locus.

11) Construction of a Plasmid Designed to Delete the egl1 Gene.

The egl1 gene of *T. reesei* has been cloned and the DNA sequence of the gene has been published (Penttila et al., 1986, Gene 45; 253-263; van Arsdell et al., 1987, Biotechnology 5:60-64). We have obtained this gene from *T. reesei* strain RL-P37 as a 4.2 kb Hind111 fragment of genomic DNA inserted at the Hind111 site of pUC100 (a derivative of pUC18 with an oligonucleotide inserted into the multiple cloning site adding restriction sites for Bgl11, Cla1 and Xho1) to give pUCEGI. An approximately 1 kb EcoRV fragment extending from a position close to the middle of the EGI coding sequence to a position beyond the 3' end of the coding sequence was removed and replaced by a 3.5 kb Scal fragment of *T. reesei* DNA containing the pyr4 gene obtained from pTpyr2. The resulting plasmid was called pPΔEGI.

The plasmid, pPΔEG1 could be digested with Hind111 to release a DNA fragment comprising only *T. reesei* genomic DNA having a segment of the egl1 gene at either end and the pyr4 gene, replacing part of the EGI coding sequence, in the centre.

12) Deletion of the ea11 Gene in Strain B31P6.

Two forms of pPΔEG1 were constructed which differed only in the orientation of the pyr4 gene with respect to the egl1 flanking regions. Strain B31P6 was transformed with a mixture of both forms of the plasmid after they had been digested with Hind111. Total DNA was extracted from stable transformants, digested with Hind111 and subjected to Southern analysis. The probe used was radio labelled pUCEGI. Hybridisation was observed to a 4.2 kb fragment of DNA from strain B31P6 representing the undeleted egl1 gene. A transformant (strain 1A52) was identified in which this 4.2 kb was no longer present but had been replaced by a fragment of approximately 6.8 kb. This is the pattern expected if the larger Hind111 fragment from pPΔEGI had integrated precisely as predicted at the egl1 locus leading to deletion of part of the EGI coding sequence and insertion of pyr4 at this position. Using a pUC plasmid as a probe for Southern analysis it was confirmed that the pUC DNA fragment of pPΔEGI had not been incorporated in strain 1A52.

T. reesei strain 1A52 may be modified to form a T. reesei cell usable in the present invention.

Example 8

Nutrient Digestibility of Diets Supplemented with a Combination of Phytase and Lipase Together with Amylase and Xylanase in Cannulated Piglets.

This trial was performed at the University of Illinois, USA.
Materials and Methods The ileal energy and protein digestibility, total tract energy digestibility, and total tract Ca and P retention of corn/soybean meal based diets supplemented with lipase on top of a phytase, amylase and xylanase in combination in surgically cannulated piglets was evaluated. The treatments consisted of:

Positive control. Nutrient adequate diet.
Negative control. Reduced in 150 kcal of DE/kg of feed, 0.15% Calcium, and 0.12% available P compared to positive control.
Phytase (500 FTU/kg).
Phytase (500 FTU/kg), amylase (1800 u/kg) and xylanase (2000 u/kg).
Phytase (500 FTU/kg), amylase (1800 u/kg), xylanase (2000 u/kg) and lipase (3000 LIPU/kg).

Twelve barrows were randomly allotted to a duplicated 6×6 Latin square design with 6 diets and 6 periods per square each. Individual pigs were identified by ear tags.

Diet formulations and calculated composition for the positive control and the negative control are presented in Table 3. Diets were mixed by supplementing enzyme products to the negative control (NC) at the expense of cornstarch. The basal diet was based on corn, soybean meal, and corn DDGS. Chromic oxide at 0.4% was added to the diets as indigestible marker.

TABLE 3

Diet formulation and nutritional specifications

| Ingredient | PC (%) | NC (%) |
|---|---|---|
| Corn | 51.05 | 57.05 |
| Soybean meal 48% | 24.00 | 21.75 |
| DDGS | 3.50 | 3.50 |
| Whey, dried | 12.00 | 12.00 |
| Fish meal | 4.00 | 4.00 |
| Soy oil | 3.00 | 0.00 |
| Starch or enzyme | 0.05 | 0.05 |
| Dicalcium phosphate | 0.85 | 0.10 |
| Limestone | 0.60 | 0.60 |
| Salt | 0.40 | 0.40 |
| Lysine-HCl | 0.20 | 0.20 |

TABLE 3-continued

Diet formulation and nutritional specifications

| Ingredient | PC (%) | NC (%) |
|---|---|---|
| DL-methionine | 0.00 | 0.00 |
| L-threonine | 0.05 | 0.05 |
| Premix[1] | 0.30 | 0.30 |
| Total | 100.00 | 100.00 |
| Calculated nutrient composition | | |
| DE (kcal/kg) | 3,570 | 3,420 |
| NE (kcal/kg) | 2,500 | 2,360 |
| Starch | 31.12 | 34.70 |
| NSP | 8.87 | 9.05 |
| CP (%) | 20.54 | 19.97 |
| Crude fat (%) | 6.16 | 3.40 |
| Calcium (%) | 0.81 | 0.64 |
| Av. phosphorus (%) | 0.40 | 0.28 |
| Dig. Lysine (%) | 1.19 | 1.14 |
| Dig. Methionine (%) | 0.32 | 0.32 |
| Dig. TSAA (%) | 0.66 | 0.65 |
| Dig. Threonine (%) | 0.74 | 0.71 |

[1]Provide the following quantities of vitamins per kilogram of complete diet: Vitamin A, 10,990 IU; vitamin D3, 1,648 IU; vitamin E, 55 IU; vitamin K, 4.4 mg; thiamin, 3.3 mg; riboflavin, 9.9 mg; pyridoxine, 3.3 mg; vitamin B12, 0.044 mg; D-pantothenic acid, 33 mg; niacin, 55 mg; folic acid, 1.1 mg; biotin, 0.17 mg; Cu, 16 mg as copper sulfate; Fe, 165 mg as iron sulfate; I, 0.36 mg as potassium iodate; Mn, 44 mg as manganese sulfate; Se, 0.3 mg as sodium selenite; and Zn, 165 mg as zinc oxide.

All pigs used in this study originated from the mating of line 337 boars and C22 females (Pig Improvement Company, Franklin, Ky.). Barrows with an average initial body weight of 12.5 kg (SD=2.15) were used. Pigs were surgically fitted with a T-cannula in the distal ileum. Following the surgery, pigs were housed in individual pens. Animals were fed conventional post-weaning diet until the initiation of the experiment. Feed was provided at daily levels of three times the estimated maintenance requirement for energy (i.e. 106 kcal ME/kg BW0.75). The feed allowance was adjusted at the beginning of each period when pig BWs were recorded.

The enzyme products were orally administered mixed with a diet for 7 days in each period: 4 days for adaptation, 1 day for fecal collection, and 2 days for ileal digesta collection. Ileal digesta samples were collected for 8 h on d 6 and 7. Briefly, a plastic bag was attached to the cannula barrel using a cable tie and digesta flowing into the bag were collected. Bags were removed whenever they were filled with digesta, or at least once every 30 minutes. Collected samples were stored at −20° C. to prevent bacterial degradation of amino acids in the digesta. At the conclusion of the experiment, frozen ileal samples were allowed to thaw at room temperature, mixed within animal and diet, and a sub-sample was collected for chemical analysis. Ileal digesta samples were lyophilized and finely ground prior to chemical analysis.

Ileal samples were analyzed for dry matter (procedure 930.15; AOAC, 2005). Gross energy concentration in ileal samples were measured using bomb calorimetry (Parr 6300 calorimeter, Pan Instruments Co., Moline, Ill.). The Cr contents of diets and ileal digesta samples were measured using an ICP method (procedure 990.08; AOAC, 2005) after nitric acid-perchloric acid wet ash sample preparation (procedure 968.088D; AOAC, 2005). These values were used to calculate ileal digestibility coefficients. Fecal samples were dried in a forced-air oven and finely ground prior to analysis. These samples were analyzed for DM, gross energy, crude protein, Ca, and P.

Data were analyzed as a latin square design using PROC MIXED procedure of SAS (SAS Institute Inc., Cary, N.C.). The model included dietary treatment, animal period and block. Means were separated using pair wise t-tests. Each animal was considered the experimental unit for all calculations. An alpha level of 0.05 was used for determination of statistical significance.

Results

Ileal energy digestibility (FIG. 23A) did not increase with addition of phytase compared with the negative control, but increased by 2.95% and 9.28% with addition of phytase+ xylanase+amylase and phytase+xylanase+amylase+lipase, respectively. These changes indicate an effect of 6.3% that was purely due to the addition of lipase on a phytase+xylanase+amylase background. Similarly, ileal digestibility of crude protein did not increase with phytase supplementation compared to the negative control diet (FIG. 23B), but supplementation of phytase+xylanase+amylase significantly increased crude protein digestibility compared to the negative control (+5.6%) and phytase supplementation (+4.0%). Additional supplementation of lipase on top of phytase+xylanase+ amylase further increased crude protein digestibility compared to the negative control (+10.7%), phytase supplementation (+9.1%), and phytase+xylanase+amylase (+4.9%).

Figure 24:
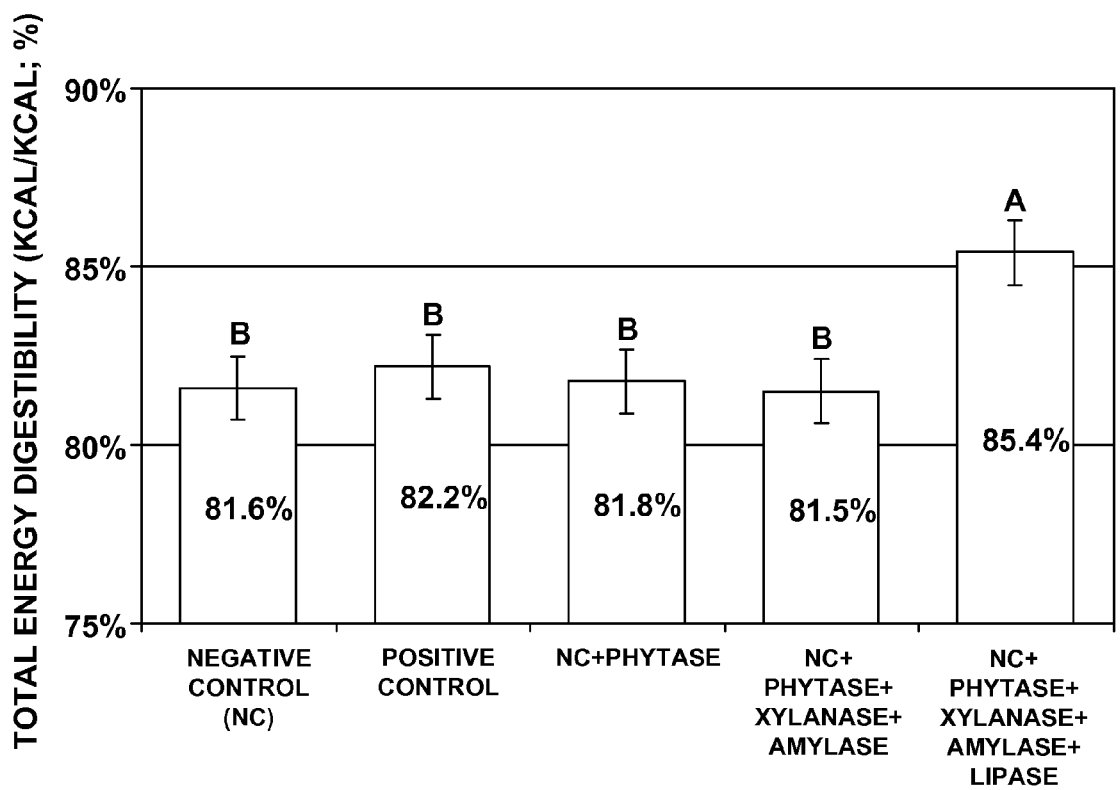
FIG. 24 shows total tract digestible energy coefficients of pigs (SEM=0.009). Bars with different letters differ at a P<0.05 level.

At the total tract level (FIG. 24), neither inclusion of phytase nor phytase+xylanase+amylase affected energy digestibility. The reduction of the difference from the ileal to the faecal level with inclusion of phytase+xylanase+amylase was not surprising, since microbial activity in the large intestine tends to annul initial differences in energy digestibility in pigs. In contrast, addition of lipase to this combination exhibited a greater faecal energy digestibility coefficient than the other treatments, which suggests the release and absorption of nutrients that otherwise would not be digested even by microorganisms in the large intestine. The combination of phytase+ xylanase+amylase+lipase increased total tract energy digestibility by 4.7% compared to the negative control feed.

Figure 25:
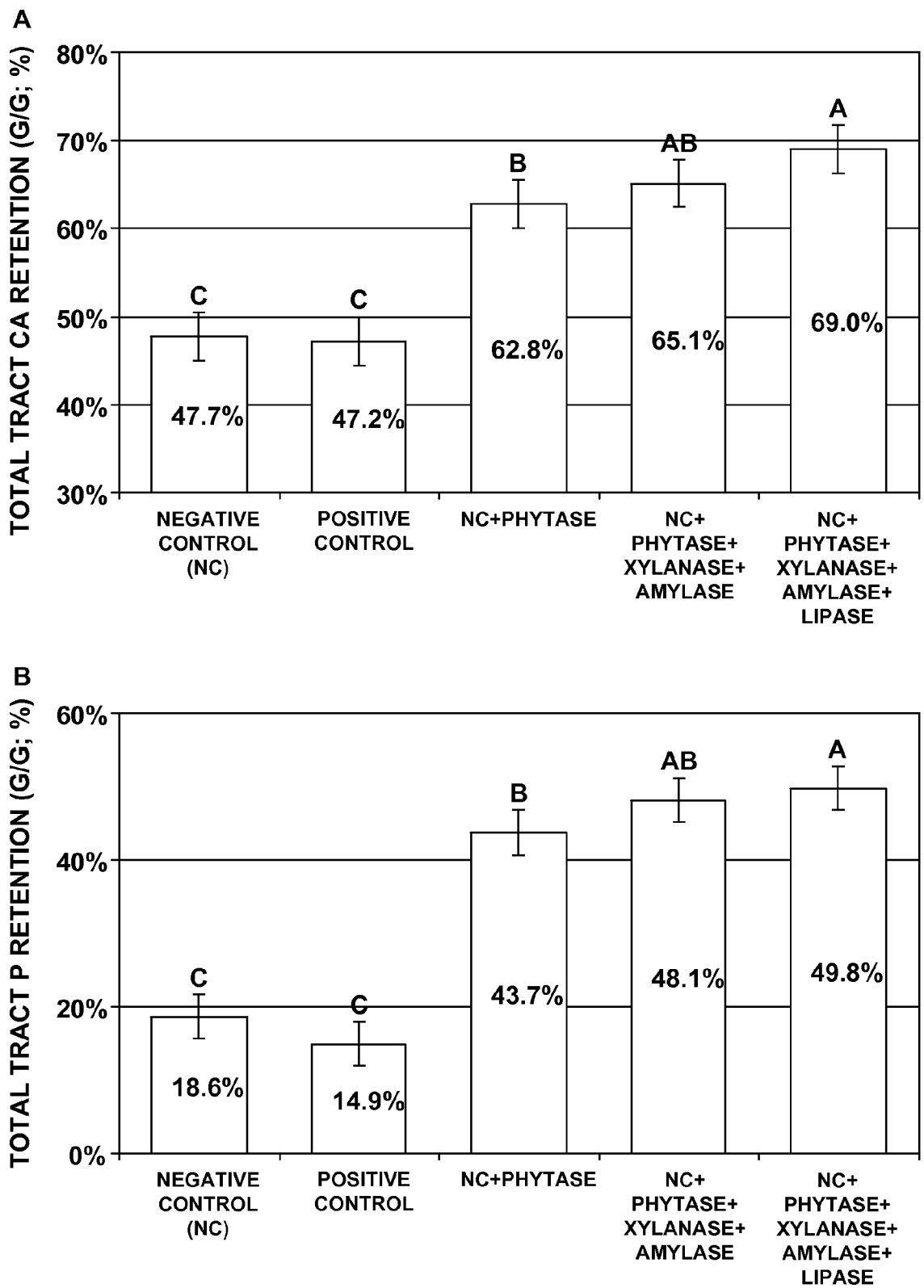
FIG. 25A shows the total tract calcium retention of pigs (SEM=0.027). Bars with different letters differ at a P<0.05 level.
FIG. 25B shows the Total tract phosphorus retention of pigs (SEM=0.030). Bars with different letters differ at a P<0.05 level.

Relative increments in total Ca (FIG. 25A) and P retention (FIG. 25B) of diets with phytase (+32% and +293%), phytase+xylanase+amylase (+36% and +323%), and phytase+xylanase+amylase+lipase (+45% and 334%, respectively) were also evident in the current study as compared to the negative control diet. Although changes in Ca and P digestibilities with phytase inclusion were expected, additional improvements with xylanase+amylase+lipase addition indicated a major role of lipase in increasing Ca and P retention of diets with phytase, amylase and xylanase. These increments were significantly greater versus the control feed and phytase by itself, which demonstrate an additive effect of the lipase on Ca and P retention.

In conclusion, addition of lipase on top of phytase+amylase+xylanase increased energy and protein digestibility at the ileal level, and energy digestibility at the total tract level compared to the negative control, phytase addition and phytase+amylase+xylanase addition. Similarly, addition of lipase on top of phytase+amylase+xylanase increased total tract Ca and P retention compared to the negative control, and diets with phytase addition. In-vitro examples contained in this patent indicate that these digestibility increments caused by the addition of lipase are mainly due to an increased phytase activity promoted by the competition of lipase for dietary calcium.

Example 9

Free Fatty Acid Production in Corn-Soy Diet at Acidic Conditions

Results from a Study of Free Fatty Acid Production in Corn-Soy Diet by Lipase

Feed samples are incubated at 40° C. with different combinations of lipases and phytases at ~pH 2.8.

Reagents:

Appropriate reagents and their concentrations were as follows. Phytase assay buffer: 0.25 M Sodium-acetate, 1 mM $CaCl_2$, 0.01% Tween 20, pH 5.5. Pepsin solution: 0.75 M HCl containing 2000 U/ml pepsin (Sigma P7000). The feed sample used was a basic corn-soy diet containing 60.01% Corn, 31.52% Soybean meal 48, 4% Soy oil, 0.4% Salt, 0.2% DL Methionine, 1.16% Limestone, 1.46% Dicalcium Phosphate, and 1.25% VIT/MIN mix.

Enzymes:

Lipase 3 as described herein. Phyzyme as described herein. TfuIII lipase is a bacterial cutinase from *Thermobifida fusca* (Tfu_0883; NCBI accession number YP_288944.1) expressed in *Bacillus subtilis*. TfuIII was analysed using the Lipase assay as described in MATERIALS AND METHODS. Further, the enzyme was analysed using the same assay, though, pH conditions were changed to pH 7.0 instead of pH 5.5. Lipase activity measured at pH 7.0 is described as LIP7U, using the same definition as described in the Lipase assay in MATERIALS AND METHODS. The ratio between lipase activity measured at pH 5.5 (LIPU) and pH 7.0 (LIP7U) was found to be 1:1.4.

Ronozyme P-CT and Natuphos are commercially available fungal phytases. The samples were obtained as dry products. 1 g of the sample was initially resuspended in 50 ml of phytase assay buffer and extracted using a magnetic stirrer for 20 min. The extraction mixture was filled to final 100 ml with phytase assay buffer and filtered through a glass fiber filter. Phytase activity of the final extracts were measured according to the phytase assay described in MATERIALS AND METHODS.

The lipase samples were diluted in $H_2O$ to an enzyme activity of 30 LIPU/ml for Lipase 3 and 30 LIPU/ml for TfuIII.

The phytase samples were diluted in phytase assay buffer to an enzyme activity of 5 FTU/ml.

In Vitro Incubation at Acidic pH:

The following enzyme combinations were evaluated in the in vitro incubation: Lipase 3, Lipase 3+Ronozyme P, Lipase 3+Natuphos, Lipase 3+Phyzyme, TfuIII, TfuIII+Ronozyme P, TfuIII+Natuphos, TfuIII+Phyzyme, and no lipase or phytase.

For each incubation, one g of feed sample was weighed into a 50 ml screw-cap tube. 100 µl of each respective enzyme solution followed by $H_2O$ to 1 ml in total was added to respective tubes. Next, 0.5 ml of Pepsin solution was added to each tube and the content was mixed carefully. Five glass marbles were added before the samples were incubated at 40° C. in a shaking water bath for 45 min. After incubation the tubes were centrifuged for 10 min at 3500 rpm. pH of the supernatant for the "no lipase and no phytase" incubation was measured. Finally, the samples were frozen in liquid nitrogen and placed in the freeze dryer over night. All incubations were performed in duplicate.

Free Fatty Acid Measurement:

The amount of free fatty acid produced during the incubation was measured using a NEFA-HR(2) kit (WAKO Chemicals GmbH). The samples were placed at room temperature and 20 ml of 96% Ethanol was added. The samples were manually resuspended before mixed on a rotary wheel for 1 hour at room temperature. After mixing the samples were centrifuged at 3500 rpm for 10 min. The supernatant was diluted 5 times in 96% Ethanol before free fatty acids in the sample were measured. 110 µl NEFA reagent R1 was equilibrated for 5 minutes at 37° C. before 15 µl diluted sample was added and the reaction mixture was incubated at 37° C. for 10 minutes. 55 µl NEFA reagent R2 was added and incubation continued for another 10 minutes at 37° C. before $OD_{520\,nm}$ was measured. The content of free fatty acid was calculated from a standard curve prepared from NEFA Standard (WAKO Chemicals GmbH).

Figure 29:
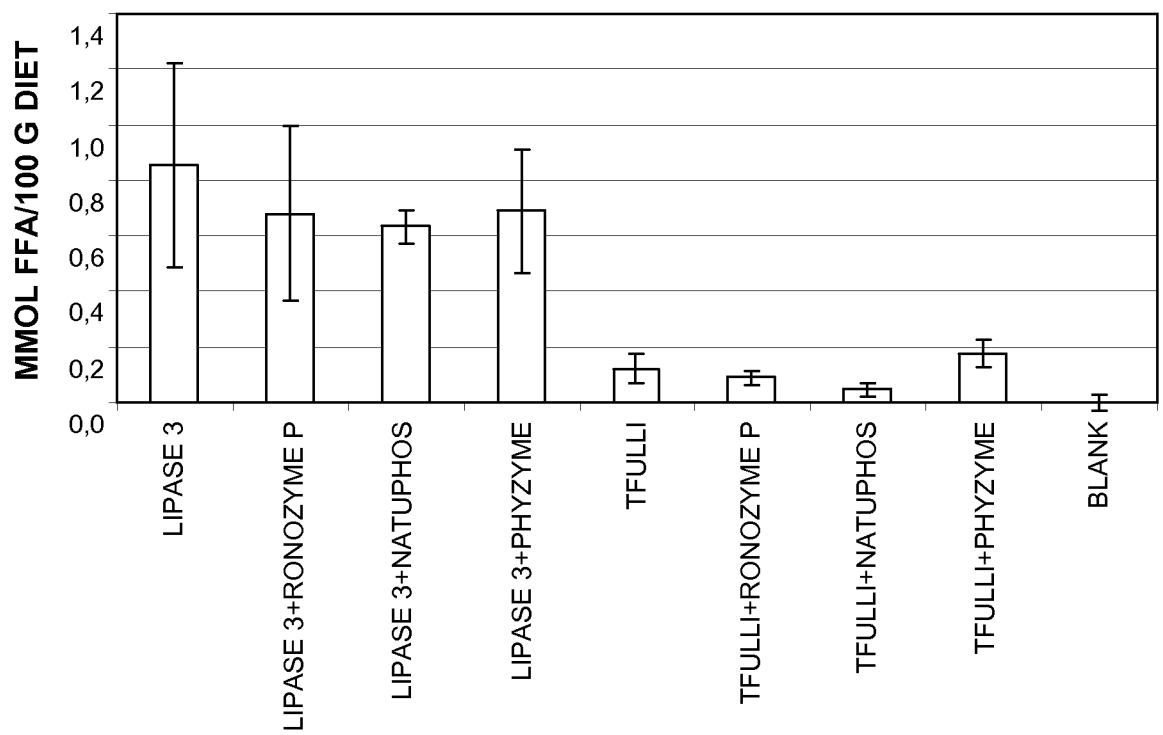
FIG. 29 shows the production of Free Fatty acid from corn-soy feed when incubated with various lipolytic enzyme/phytase combinations.

Results:

The results of the free fatty acid measurement are presented in FIG. 29. This Figure shows Free fatty acid production in corn-soy diet. The amount of produced free fatty acids (FFA) is corrected for the blank value without added lipase or phytase. The pH of the incubation with no lipase and no phytase was measured to be pH 2.8 and assumed to be representative of all the incubations in this example. This demonstrates that the incubations were done at very acidic conditions. Lipase 3 alone or in combination with Phyzyme, Natuphos, or Ronozyme P shows a significant release of FFA compared to all the samples with TfuIII, either alone or in combination with Phyzyme, Natuphos, or Ronozyme P. This clearly shows that Lipase 3 would be very effective in fat hydrolysis in the acidic environment in the stomach of a pig or gizzard of a chicken.

Example 10

Effect on Phytase Activity of Adding Calcium to the Assay Mixture and Effect of Adding Free Fatty Acid to an Assay Containing CaCl2

Results from a study of phytic acid-calcium complex formation with increasing concentration of calcium and regain of the phytase activity by adding free fatty acid.

Background

Phytic acid can readily form chelates with divalent minerals such as calcium. This phytate-mineral complex may exist as insoluble precipitates or soluble complexes and can potentially be resistant to hydrolysis by phytase. Free fatty acid may potentially function as a competitive chelator, by forming Ca-soaps resulting in decreased formation of phytase-resistant forms of phytic acid and concomitant increase in released phytate-P.

Reagents:

Appropriate reagents and their concentrations were as follows. Assay buffer: 0.25 M Sodium-Acetate, 3% Triton X-100 (w/v), pH 5.5. Phytate solution: 9.1 mM Phytic acid sodium salt hydrate (Sigma P0109) in assay buffer. $CaCl_2$ solution: 0.3 M $CaCl_2$ in assay buffer. FFA solution: 40.8 mg/ml Palmitic acid—Stearic acid mixture (Sigma 09586) dissolved in 96% Ethanol. Ethanol: 96% Ethanol.

Enzymes:

Phyzyme as described herein. Ronozyme P-CT and Natuphos are commercially available fungal phytases. BP17 as described herein. The samples were obtained as dry product. 1 g of the sample was initially resuspended in 50 ml of 0.25 M Sodium-acetate, 1 mM $CaCl_2$, 0.01% Tween 20, pH 5.5 and extracted using a magnetic stirrer for 20 min. The extraction mixture was filled to final 100 ml with 0.25 M Sodium-acetate, 1 mM $CaCl_2$, 0.01% Tween 20, pH 5.5 and filtered through a glass fiber filter. Phytase activity of the final extracts was measured according to the phytase assay described in MATERIALS AND METHODS.

The phytase samples were diluted in 0.25 M Sodium-acetate, 1 mM $CaCl_2$, 0.01% Tween 20, pH 5.5 to an enzyme activity of 0.3 FTU/ml.

Phytic Acid Hydrolysis by Phytase:

0.5 ml Ethanol was mixed with 1.4 ml assay buffer and 1 ml phytate solution in a 12 ml test tube. The mixture was equilibrated in a water bath at 37° C. for 5 min before the reaction was started by addition of 0.1 ml phytase solution. For the blank measurement 0.1 ml assay buffer was added instead of phytase solution. After 1 hour incubation at 37° C. the reaction was stopped by addition of 0.75 ml 2.5 M HCl. All incubations were performed in duplicate.

Phytic Acid Hydrolysis by Phytase with Increasing Concentration of CaCl2:

The appropriated volume of $CaCl_2$ solution, was mixed in a 12 ml test tube with 0.5 ml Ethanol, 1 ml phytate solution and assay buffer to a final assay volume of 3 ml. The mixture was equilibrated in a water bath at 37° C. for 5 min before the reaction was started by addition of 0.1 ml phytase solution. For the blank measurement 0.1 mL assay buffer was added instead of phytase solution. After 1 hour incubation at 37° C. the reaction was stopped by addition of 0.75 ml 2.5 M HCl. All incubations were performed in duplicate.

Phytic Acid Hydrolysis by Phytase in the Presence of 15 mM CaCl2 and with Increasing Concentration of FFA:

The appropriated volume of FFA solution was mixed in a 12 ml test tube with Ethanol to a volume of 0.5 ml. 0.15 ml Calcium solution, 1 ml phytate solution and assay buffer to a final assay volume of 3 ml was added. The mixture was equilibrated in a water bath at 37° C. for 5 min before the reaction was started by addition of 0.1 ml phytase solution. For the blank measurement 0.1 mL assay buffer was added instead of phytase solution. After 1 hour incubation at 37° C. the reaction was stopped by addition of 0.75 ml 2.5 M HCl. All incubations were performed in duplicate.

Measurement of Phytase Activity:

Inorganic phosphate concentration in the hydrolysis samples, were measured using the Phosphorus reagent (Thermo Scientific) on the Konelab analyzer. 180 µl Phosphorus reagent was mixed with 5 µl sample and incubated for 4 minutes at 37° C. before $OD_{340\,nm}$ were measured. The content of phosphate was calculated using the sCal Konelab Calibrator and Nortrol Konelab Control (Thermo Scientific). Phytase activity was calculated as released inorganic phosphate by subtracting the blank measurement from the result. All activities were calculated as relative to the sample with no $CaCl_2$ present.

Results

FIG. 30 shows the production of a phytase resistant complex of phytic acid and calcium and reversal by adding free fatty acids. FIG. 30A shows the effect on phytase activity of increasing $CaCl_2$ concentration. FIG. 30B shows the effect on the phytase activity of adding free fatty acids to the reaction mixture containing 15 mM.

The results of the phytic acid hydrolysis with increasing concentration of $CaCl_2$ are presented in FIG. 30A. Decreasing phytase activity with increasing $CaCl_2$ concentration is observed for all four phytases. For Phyzyme, BP17, and Ronozyme P reduced activity starts at 5 mM $CaCl_2$, while Natuphos has increased activity at 5 mM and reduced activity starts at 15 mM $CaCl_2$. At 20 mM $CaCl_2$ no phytase activity is observed for Phyzyme, BP17, and Ronozyme P, indicating that at $CaCl_2$ concentrations above 20 mM all phytic acid is bound in a complex resistant against, at least Phyzyme, BP17, and Ronozyme P hydrolysis. For Natuphos a significant reduction in phytase activity is observed at 30 mM $CaCl_2$, though a $CaCl_2$ concentration of 60 mM seems to be necessary to bind all phytic acid in a complex resistant against Natuphos hydrolysis. The results on phytase activity of Phyzyme, BP17, and Ronozyme P of adding free fatty acids to the reaction mixture containing 15 mM $CaCl_2$ is presented in FIG. 30B. When adding free fatty acid to the reaction mixture containing 15 mM $CaCl_2$, the phytases regain more and more activity with increasing amount of free fatty acid. Small differences between the three phytases in response to the free fatty acid concentration is observed, though all three regains 100% activity at 25 mM free fatty acid. This clearly demonstrates that free fatty acids can competitively bind calcium, and thereby has the ability to prevent formation of a phytase resistant phytic acid-calcium complex. Free fatty acids may be added as a single component as demonstrated here or can be formed by the action of a lipase on a triglyceride substrate.

Example 11

Lipase Incubation Followed by Phytase Assay—Effect on Phytase Activity of Adding Calcium to the Assay Mixture and Effect of Adding Lipase Reaction Mix to an Assay Containing CaCl2

Figure 31:
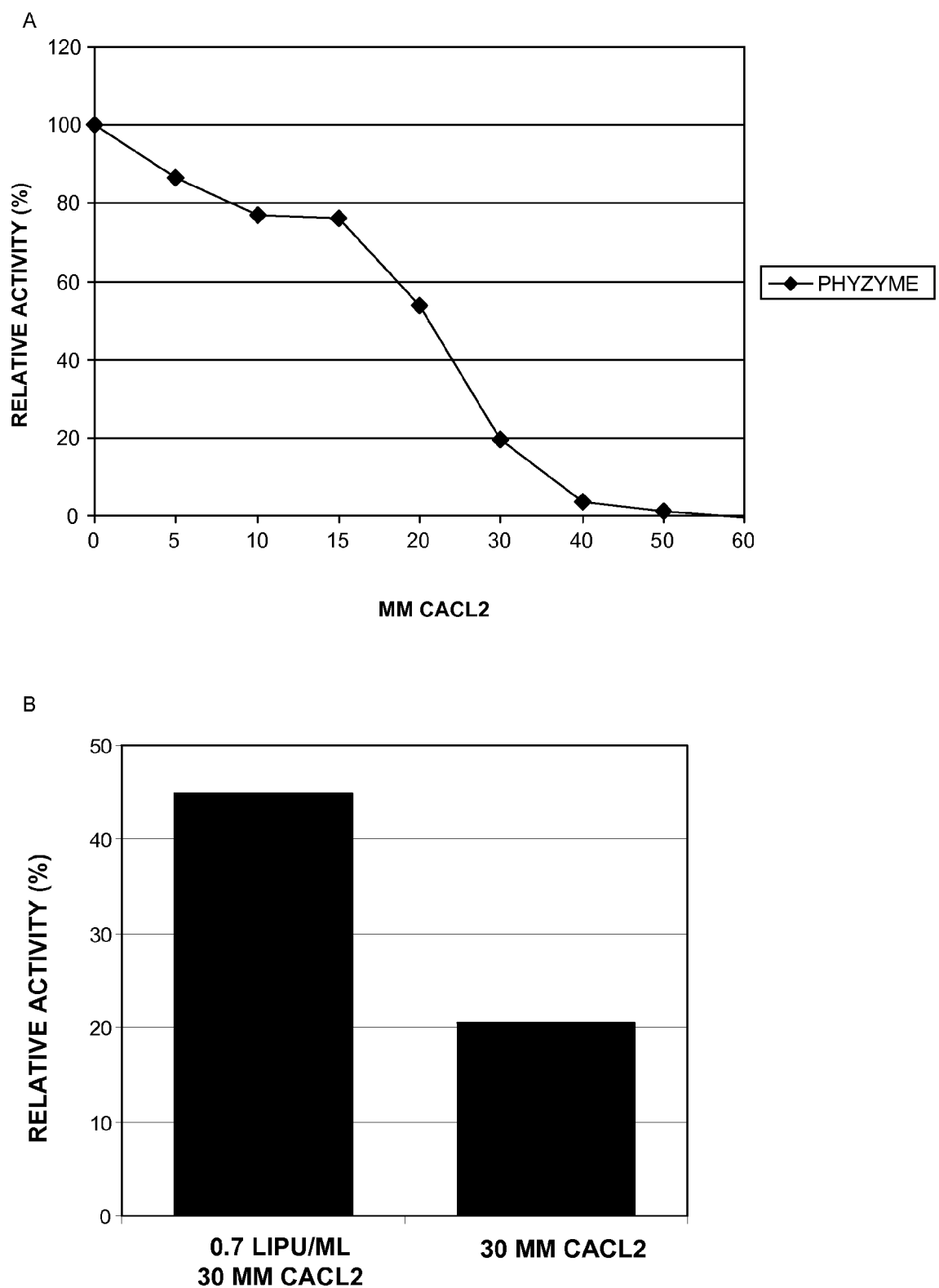
FIG. 31 shows the production of a phytase resistant complex of phytic acid and calcium and reversal by adding Lipase reaction mixture including lipase.

Results from a study of phytic acid-calcium complex formation with increasing concentration of calcium and regain of the phytase activity by adding free fatty acid produced by Lipase 3.
Background
In example 11 the effect on phytase activity of adding free fatty acids to a phytase reaction mixture containing 15 mM $CaCl_2$ was described. In this example a similar experiment is conducted, though the free fatty acids are produced by Lipase 3. A triglyceride emulsion is incubated with Lipase 3, a fraction of this mixture is subsequently added to the phytase reaction mixture containing 30 mM $CaCl_2$ and the effect on the phytase activity is observed.
Reagents:
Appropriate reagents and their concentrations were as follows. Lipase sample buffer: 50 mM Sodium-acetate, pH 5.0, 0.1% BSA (w/v), 1.2% NaCl (w/v). Triglyceride substrate: 2% Glyceryl Trioctanoate (v/v), 0.3% NaCl (w/v), 13% Triton X-100 (w/v), 120 mM Sodium-Acetate, pH 5.0. Phytase assay buffer: 0.25 M Sodium-Acetate, pH 5.5. Phytate solution: 9.1 mM Phytic acid sodium salt hydrate (Sigma P0109) in assay buffer. $CaCl_2$ solution: 0.3 M $CaCl_2$ in assay buffer. Ethanol: 96% Ethanol.
Enzymes:
Lipase 3 and Phyzyme as described herein. The Lipase 3 sample was diluted in Lipase sample buffer to an enzyme activity of 10 LIPU/ml. The phytase sample was diluted in 0.25 M Sodium-acetate, 1 mM $CaCl_2$, 0.01% Tween 20, pH 5.5 to an enzyme activity of 0.3 FTU/ml.
Lipase Reaction Mixture:
5 ml Triglyceride substrate was mixed with 1.0 ml lipase solution in a 12 ml test tube. For a blank mixture 1.0 ml Lipase sample buffer was added instead of Lipase solution. The mixtures were incubated in a water bath at 30° C. for 120 min with continuous stirring. The mixtures were directly used as Lipase reaction mixture or Blank reaction mixture, respectively, in the following phytase assay.
Phytic Acid Hydrolysis by Phytase with Increasing Concentration of CaCl2 Including Blank Reaction Mixture:
The appropriate volume of $CaCl_2$ solution was mixed in a 12 ml test tube with 1.3 ml Blank reaction mixture, 1 ml phytate solution and assay buffer to a final assay volume of 3 ml. The mixture was equilibrated in a water bath at 37° C. for 5 min before the reaction was started by addition of 0.1 ml phytase solution. For the blank measurement 0.1 mL assay buffer was added instead of phytase solution. After 1 hour incubation at 37° C. the reaction was stopped by addition of 0.75 ml 2.5 M HCl.
Phytic Acid Hydrolysis by Phytase in the Presence of 30 mM CaCl2 and Lipase Reaction Mixture:
1.3 ml Blank reaction mixture or Lipase reaction mixture was mixed in a 12 ml test tube with 0.3 ml calcium solution, 1 ml phytate solution and assay buffer to a final assay volume of 3 ml. The mixture was equilibrated in a water bath at 37° C. for 5 min before the reaction was started by addition of 0.1 ml phytase solution. After 1 hour incubation at 37° C. the reaction was stopped by addition of 0.75 ml 2.5 M HCl.
Measurement of Phytase Activity:
Inorganic phosphate concentration in the hydrolysis samples, were measured using the Phosphorus reagent (Thermo Scientific) on the Konelab analyzer. 180 µl Phosphorus reagent was mixed with 5 µl sample and incubated for 4 minutes at 37° C. before $OD_{340\ nm}$ were measured. The content of phosphate was calculated using the sCal Konelab Calibrator and Nortrol Konelab Control (Thermo Scientific). Phytase activity was calculated as released inorganic phosphate by subtracting the blank measurement from the result. All activities were calculated as relative to the sample with no $CaCl_2$ present.
Results
FIG. 31 shows the production of a phytase resistant complex of phytic acid and calcium and reversal by adding Lipase reaction mixture including lipase. FIG. 31A shows the effect on phytase activity of increasing $CaCl_2$ concentration and FIG. 31B shows the effect on the phytase activity of adding Lipase reaction mixture to the phytase reaction mixture containing 30 mM $CaCl_2$.
The results of the phytic acid hydrolysis with increasing concentration of $CaCl_2$ in the presence of a blank lipase reaction mixture (no lipase present) are presented in FIG. 31A. Decreasing phytase activity with increasing $CaCl_2$ concentration is observed with a significant reduction in phytase activity at 30 mM $CaCl_2$ and no remaining activity at 40 mM $CaCl_2$. This calcium inhibition profile is different from the corresponding curve shown in Example 11. The reason is the amount of Triton X-100 applied to emulsify the Triglyceride substrate in the lipase reaction mixture, which results in twice as much Triton X-100 in the phytase reaction mixture as compared to the experiment described in Example 11. The change of Triton X-100 concentration changes the properties for complex formation between the phytic acid and calcium.
The results of adding lipase reaction mixture to the phytase reaction mixture containing 30 mM $CaCl_2$ is presented in FIG. 31B. Adding the lipase reaction mixture including lipase, results in a significant increase of phytase activity compared to the samples without lipase added.
This clearly demonstrates that free fatty acids produced by lipase activity on a triglyceride substrate can competitively bind calcium, and thereby has the ability to prevent formation of a phytase resistant phytic acid-calcium complex. When the phytic acid-calcium complex is not formed a larger amount of phytic acid is more readily accessible to degradation by the phytase leading to increased phytase activity.
In the animal, this increase in phytase activity as a result of the lipase activity, will lead to increased P and Ca retention as well as increased apparent amino acid digestibility (Ravindran, V. et al, Br. Poult. Sci., 41, 193-200 (2000) and Selle, P. H. et al, Livestock Science, 124, 126-141 (2009)). This will lead to increased P and Ca retention as well as increased energy metabolizability and apparent amino acid digestibility when compared to animals not supplemented the lipase on top of phytase.

Example 12 pH Profile of Lipases in Feed

Results from a Study of the pH Profile of Lipase 3 and Pancreatic Lipase in Feed Feed samples are incubated at 40° C. with Lipase 3 and pancreatic lipase using different pH buffers to show the pH profile of Lipase 3 and pancreatic lipase.

Enzymes:

Lipase 3 as described herein. Pancreatic lipase as in Pancreatin from porcine pancreas (Sigma P7545). The Lipase 3 sample was diluted in $H_2O$ to an enzyme activity of 300 LIPU/ml. The Pancreatin sample was diluted in $H_2O$ to a concentration of 2 mg/ml.

Reagents:

Appropriate buffers and their concentrations were as follows. 0.25 M HCl; 0.5 M Glycine-HCl, pH 2.5; 0.5 M Glycine-HCl, pH 3.5; 0.5 M Sodium-phosphate, pH 6.5; 0.5 M Sodium-phosphate, pH 7.5; 0.5 M Tris, pH 8.5; 1 M $NaHCO_3$, pH 10. Other reagents were as follows. TDC solution: Sodium taurodeoxycholate (Sigma T0875) was diluted in $H_2O$ to 80 mM. The feed sample used was a basic corn-soy diet containing 60.01% Corn, 31.52% Soybean meal 48, 4% Soy oil, 0.4% Salt, 0.2% DL Methionine, 1.16% Limestone, 1.46% Dicalcium Phosphate, and 1.25% VIT/MIN mix.

In Vitro Incubation with Different pH Buffers:

For each incubation, one g of corn-soy feed sample was weighed into a 50 ml screw-cap tube. 0.1 ml of enzyme solution followed by 0.1 ml of TDC solution and 1.8 ml of respective buffer was added to respective tubes. Five glass marbles were added before the samples were incubated at 40° C. in a shaking water bath for 120 min. After incubation the tubes were centrifuged for 10 min at 3500 rpm and the pH of the supernatant was measured. Afterwards the samples were frozen in liquid nitrogen and placed in the freeze dryer over night. All incubations were performed in duplicate.

Free Fatty Acid Measurement:

The amount of free fatty acid produced during the incubation was measured using a NEFA-HR(2) kit (WAKO Chemicals GmbH). The samples were placed at room temperature and 20 ml of 96% Ethanol was added. The samples were manually resuspended before mixed on a rotary wheel for 1 hour at room temperature. After mixing the samples were centrifuged at 3500 rpm for 10 min. The supernatant was diluted 5 times in 96% Ethanol before free fatty acids in the sample was measured. 110 µl NEFA reagent R1 was equilibrated for 5 minutes at 37° C. before 15 µl diluted sample was added and the reaction mixture was incubated at 37° C. for 10 minutes. 55 µl NEFA reagent R2 was added and incubation continued for another 10 minutes at 37° C. before $OD_{520\ nm}$ was measured. The content of free fatty acid was calculated from a standard curve prepared from NEFA Standard (WAKO Chemicals GmbH).

Figure 32:
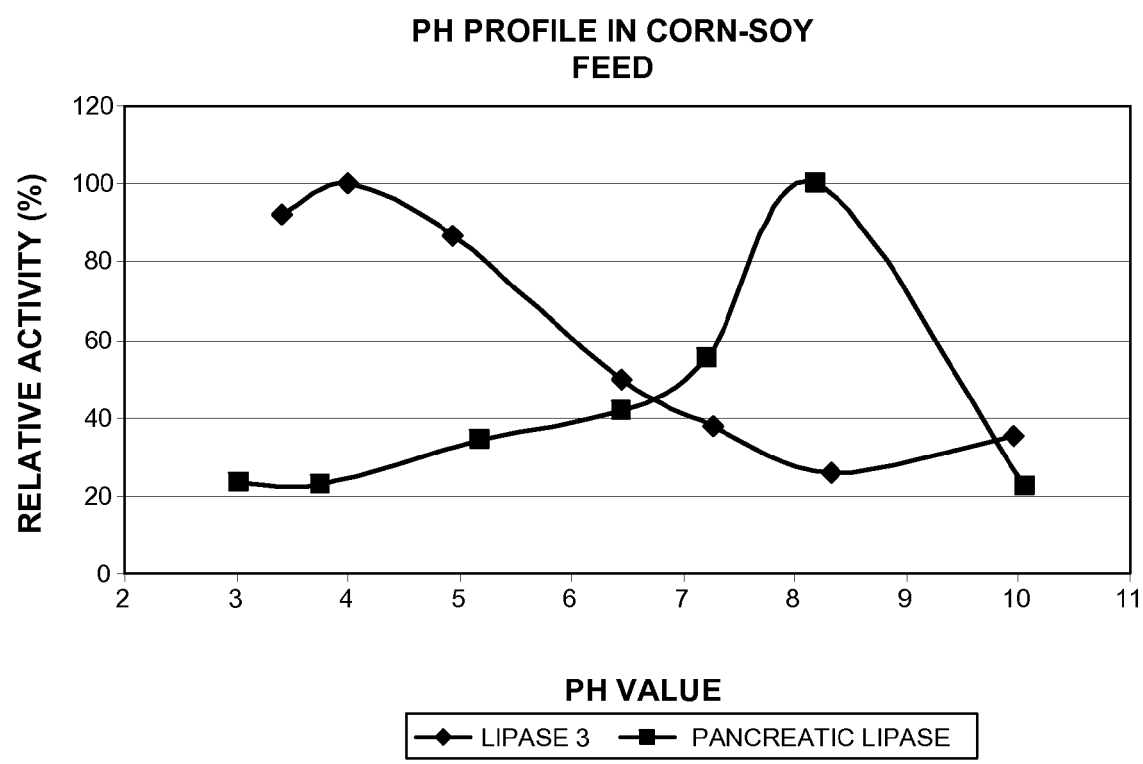
FIG. 32 shows the pH profile of Lipase 3 and Pancreatic lipase measured in a corn-soy diet.

Results:

FIG. 32 shows the pH profile of Lipase 3 and Pancreatic lipase measured in a corn-soy diet. The concentration of Lipase 3 was 30 LIPU/g of feed and the concentration of Pancreatic lipase was 0.2 mg/ml of feed. The activity is shown as relative to the highest measured amount of produced free fatty acid.

The pH in the different buffers was as follows for Lipase 3 and pancreatic lipase, respectively: 0.25 M HCl provides pH 3.41 and pH 3.02; 0.5 M Glycine-HCl, pH 2.5 provides pH 3.99 and pH 3.76; 0.5 M Glycine-HCl, pH 3.5 provides pH 4.93 and pH 5.18; 0.5 M Sodium-phosphate, pH 6.5 provides pH 6.45 and pH 6.45; 0.5 M Sodium-phosphate, pH 7.5 provides pH 7.26 and pH 7.22; 0.5 M Tris, pH 8.5 provides pH 8.33 and pH 8.18; 1 M $NaHCO_3$, pH 10 provides pH 9.95 and pH 10.07. For Lipase 3 the pH optimum in feed is found at pH 4.0 with decreasing activity at both lower and higher pH. pH 3.4 is the lowest pH evaluated and the activity will probably continue to decrease with further decreasing pH. For the pancreatic lipase the pH optimum in feed is found at pH 8.2 with decreasing activity at both lower and higher pH. The conclusion is that Lipase 3 has a pH profile very different from the pH profile of the pancreatic lipase. Further, the pH profile of Lipase 3 indicates that Lipase 3 could be very effective in fat hydrolysis in the acidic environment in the stomach of a pig or gizzard of a chicken.

Example 13

Ileal Digestibility and Total Tract Retention of Phosphorus and Calcium of Diets Supplemented with Lipase, Phytase and the Combination of Lipase+Phytase Versus a Control Diet in Broiler Chickens Materials and Methods Experiments were conducted to evaluate the ileal digestibility, and the total tract retention of P and Ca in broiler chickens fed diets supplemented with lipase or phytase by themselves, and lipase and phytase in combination, versus a negative control diet. Diets (Table 4) were based on corn and soybean meal, and contained corn DDGS, corn gluten meal, and soybean oil.

TABLE 4

| Composition and calculated analysis (g/kg as fed) of the diets | | |
|---|---|---|
| Ingredient | Pre-starter | Negative control |
| Corn | 498.3 | 496.8 |
| Corn DDGS | 50.0 | 50.0 |
| Corn gluten meal, 60% | 50.0 | 50.0 |
| Soybean meal, 48% | 311.9 | 312.2 |
| Maize/Wheat starch | 2.0 | 2.0 |
| Soybean oil | 40.0 | 40.0 |
| Lysine HCl | 3.8 | 3.8 |
| DL-methionine | 2.7 | 2.7 |
| L-threonine | 1.0 | 1.0 |
| Inert marker | 3.0 | 3.0 |
| Salt | 3.6 | 3.6 |
| Limestone | 13.8 | 3.0 |
| Dicalcium phosphate | 16.4 | 13.5 |
| Trace mineral- vitamin premix | 3.5 | 3.5 |
| Space (Enzyme) | 0.0 | 14.9 |
| Calculated analysis | | |
| Metabolisable energy, kcal/kg | 3.140 | 3.100 |
| Crude protein, g/kg | 240 | 240 |
| Digestible lysine, g/kg | 12.6 | 12.6 |
| Digestible methionine, g/kg | 6.4 | 6.4 |
| Digestible methionine + cysteine, g/kg | 9.0 | 9.0 |
| Digestible threonine, g/kg | 7.9 | 7.9 |
| Calcium, g/kg | 10.5 | 5.7 |
| Available phosphorus, g/kg | 4.3 | 3.8 |

The experimental design consisted of 6 dietary treatments, each randomly allocated to 6 replicate cages (8 birds per cage) as follows:
1. Negative control (NC)
2. NC+lipase (1,000 LIPU/kg)

3. NC+lipase (3,000 LIPU/kg)
4. NC+phytase (500 FTU/kg)
5. NC+phytase (500 FTU/kg)+lipase (1,000 LIPU/kg)
6. NC+phytase (500 FTU/kg)+lipase (3,000 LIPU/kg)

Day-old broiler chicks were randomly assigned to electrically heated battery brooders in an environmentally controlled room. The chicks received constant fluorescent illumination and were allowed free access to the diets and water. The birds received a pre-starter diet until day 14. At this age, birds were assigned to dietary treatments on the basis of body weight, and transferred to grower cages. Birds were fed the experimental diets from day 14 until day 21. The temperature was maintained at 31° C. for the first week and then gradually reduced to 22° C. by the third week.

Feed intake and total excreta output of each cage were measured from day 17 to 20 post-hatch. Excreta from each cage were pooled, mixed in a blender and sub-sampled. Each sub-sample was freeze-dried, ground to pass through a 0.5 mm sieve and stored in airtight plastic containers at −4° C. pending analysis. The diets and excreta samples were analysed for dry matter (DM), calcium (Ca), and phosphorous (P).

On d 21, two birds from each replicate cage were selected and euthanised by intra-cardial injection of sodium pentabarbitone. The small intestine immediately was exposed and the contents of the lower half of the ileum were collected by gently flushing with distilled water into plastic containers. The ileum was defined as that portion of the small intestine extending from vitelline diverticulum to a point 40 mm proximal to the ileo-caecal junction. Digesta were pooled within a cage and were lyophilised, ground to pass through a 0.5-mm sieve, and stored at −4° C. in airtight containers until laboratory analysis for DM, titanium, Ca, and P.

Data were analyzed by ANOVA using PROC MIXED procedure of SAS (SAS Institute Inc., Cary, N.C.). The model included the fixed effect of dietary treatment and the random effect of block. Means were separated using pair wise t-tests. Each pen was considered the experimental unit for all calculations. An alpha level of 0.05 was used for determination of statistical significance.

Results

Figure 33:
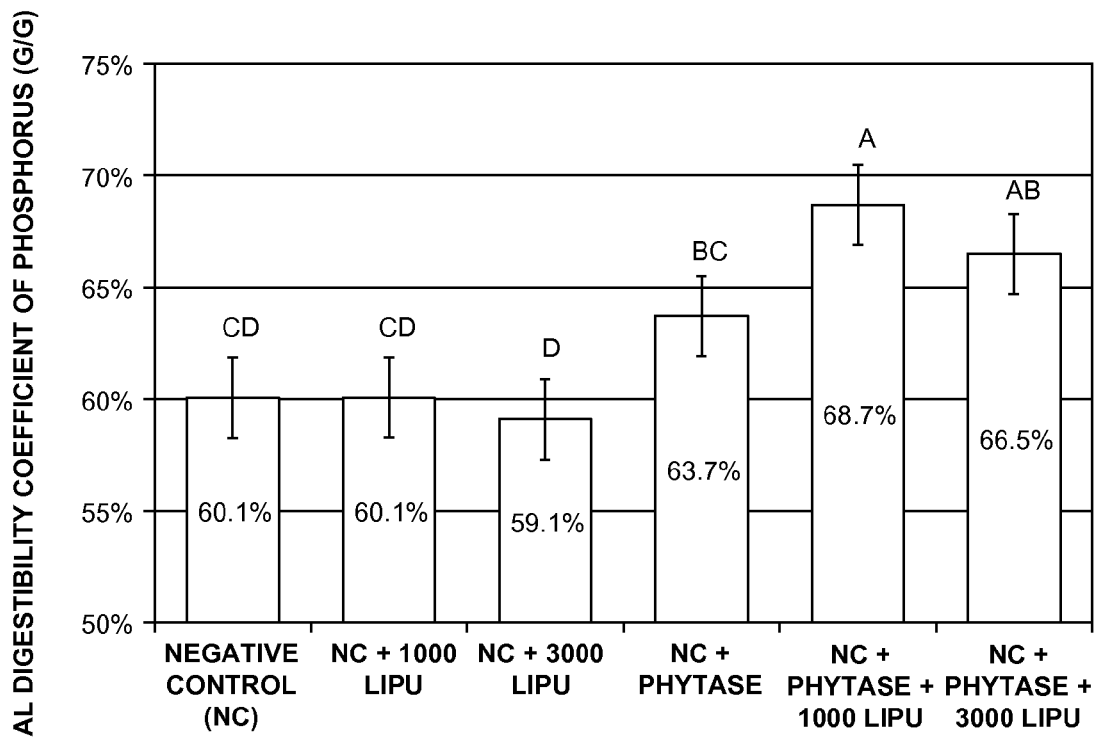
FIG. 33 shows the ileal digestibility coefficient of phosphorus in broiler chickens. Bars with different letters differ at a P<0.05 level.

FIG. 33 shows that phytase did not significantly increase phosphorus ileal digestibility compared to the negative control, but produced a numeric increment of 6.0% as it was expected. Lipase, both at 1,000 and 3,000 LIPU/kg, produced no effect on ileal phosphorus digestibility compared to the negative control. In contrast, the combination of lipase+phytase was able to significantly increase the ileal phosphorus digestibility compared to the negative control by 14.3% at 1,000 LIPU/kg and 10.6% at 3,000 U/kg of lipase inclusion. The combination of lipase+phytase significantly increase ileal phosphorus digestibility compared to the phytase treatment, only when lipase was included at 1,000 u/kg by a difference of 7.8%.

Figure 34:
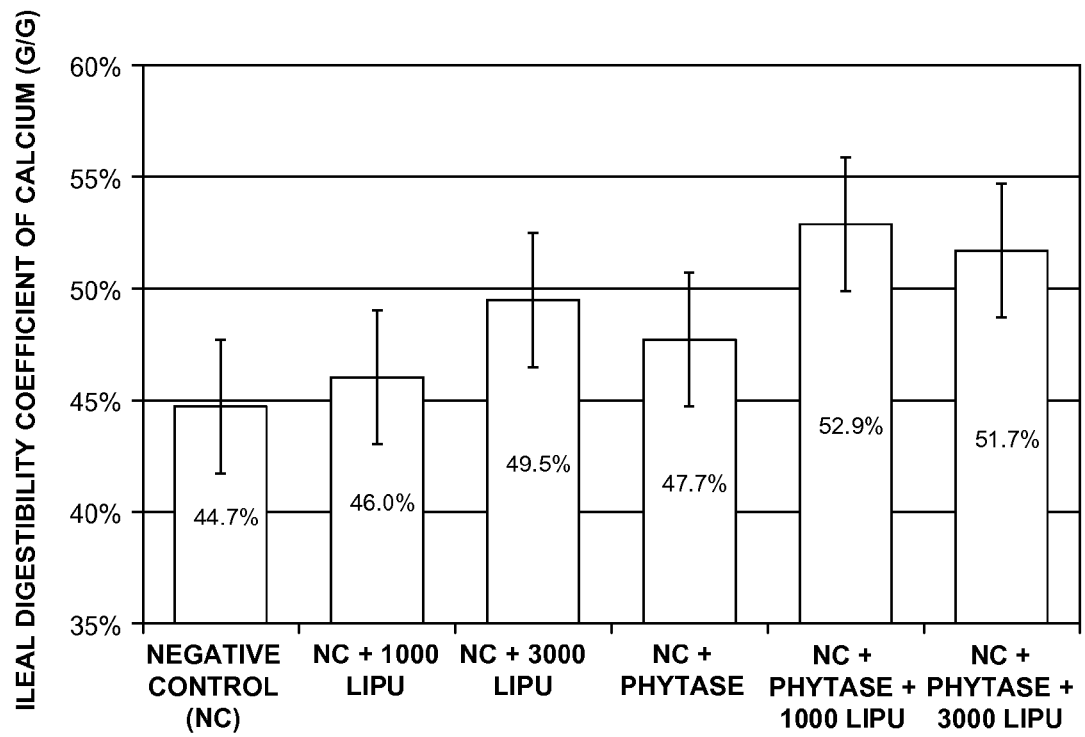
FIG. 34 shows the ileal digestibility coefficient of calcium in broiler chickens. Bars with different letters differ at a P<0.05 level.

FIG. 34 shows that there are no significant effects on ileal calcium digestability of any of the enzyme treatments compared to the negative control diet. Nonetheless, the numerically highest Ca digestibility values were obtained with the combinations phytase+lipase, which exhibited values that were 118.3% and 115.6% of the values obtained with the negative control diet, when lipase was included at 1,000 u/kg and 3,000 u/kg, respectively.

Figure 35:
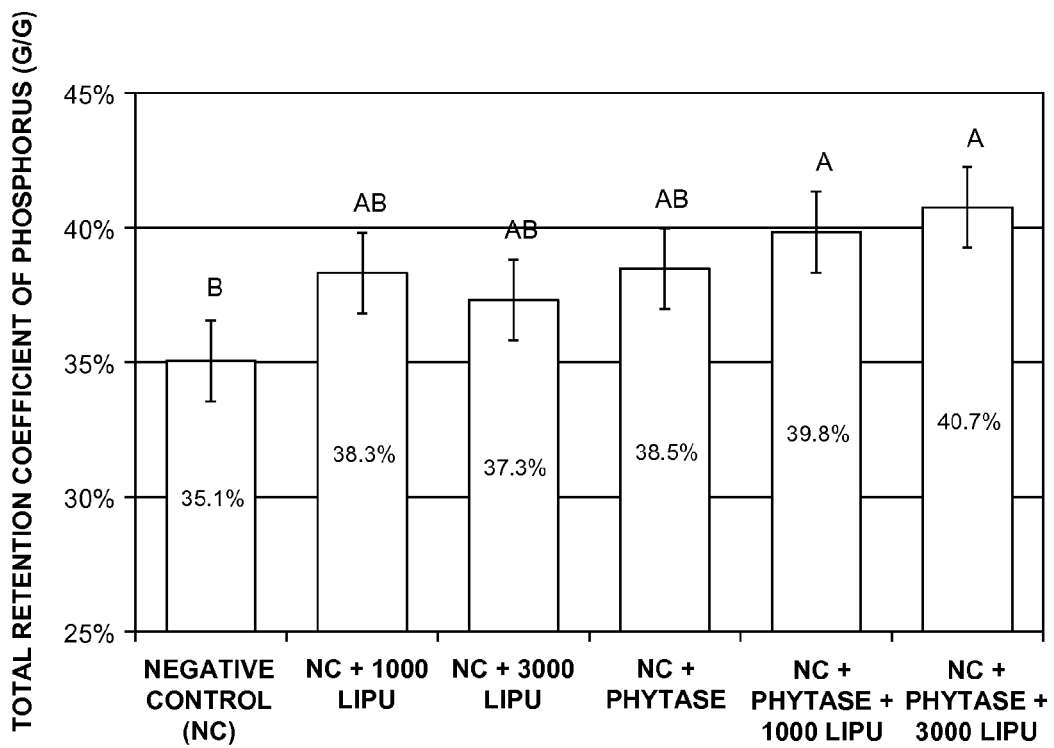
FIG. 35 shows the total tract retention coefficient of phosphorus in broiler chickens. Bars with different letters differ at a P<0.05 level.

FIG. 35 shows that neither lipase inclusion nor phytase inclusion resulted in any significant differences in total tract phosphorus retention compared to the negative control. Nonetheless, phytase produced a numeric increment of phosphorus retention of 9.7% compared to the negative control. The combination of lipase+phytase significantly increased phosphorus retention compared to the negative control by 13.4% and 16.0% when lipase was supplemented at 1,000 and 3,000 LIPU/kg, respectively.

Figure 36:
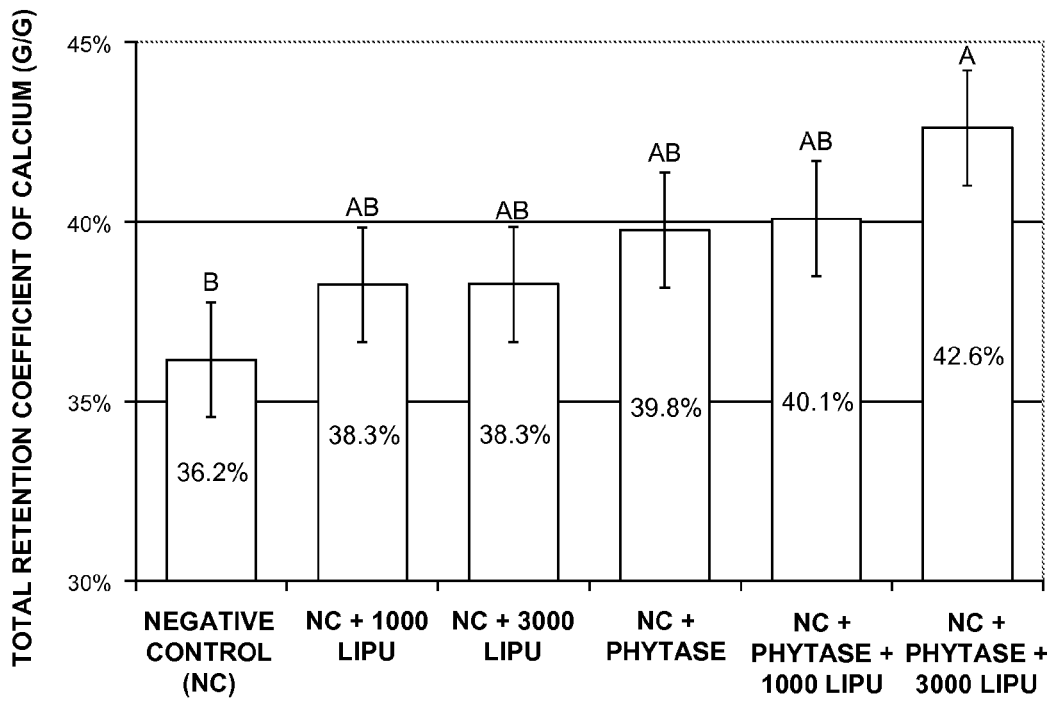
FIG. 36. Total tract retention coefficient of calcium in two experiments with broiler chickens. Bars with different letters differ at a P<0.05 level.
Figure 37:
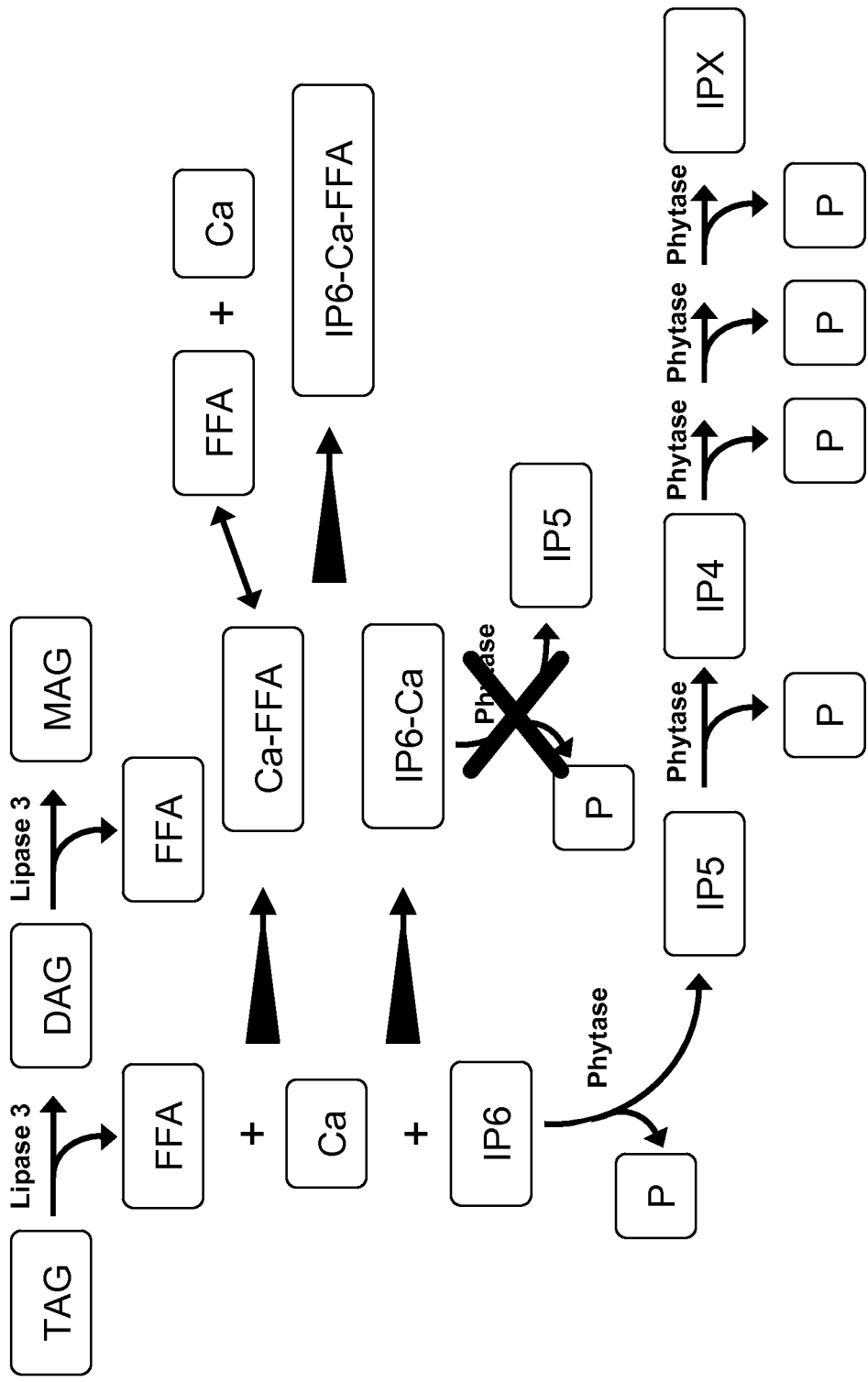
FIG. 37 shows the inventors Hypothesis of the mechanism involved in the lipase and phytase interaction in the digestive tract of poultry. The figure shows a schematic representation of the possible mechanism behind the synergistic effect observed between Lipase and phytase. Due to the action of Lipase 3 under acidic conditions, free fatty acids (FFA) are liberated at an earlier stage in digestion compared to the situation without Lipase 3. These FFA may bind with excess calcium (Ca) to form soaps in the gut. There is then less free Ca available to bind to phytic acid (IP6) and form the phytase resistant complex. Eventually, more IP6 is degraded by the phytase as compared to the situation without Lipase 3 added. This leads to increased phosphate (P) liberation and subsequently absorption by the animal. The FFA-Ca complexes may dissolve later in the digestive tract resulting in increased fat and Ca absorption. If no phytase is present to hydrolyse the IP6, this may complex with the FFA-Ca soap to form an insoluble non-degradable IP6-Ca-FFA soap, resulting in decreased fat, Ca, and P absorption.

FIG. 36 shows that neither lipase inclusion nor phytase inclusion results in any significant differences in total tract calcium retention compared to the negative control. However, the combination of phytase and 3,000 LIPU/kg significantly increased the Ca retention by 17.7% compared with the negative control.

In synthesis, neither lipase nor phytase produced significant effects of P and Ca digestibility in the current study. However, the combination of phytase and 1,000 LIPU/kg of lipase increased ileal and total tract phosphorus retention compared to the negative control, and ileal phosphorus digestibility compared to phytase inclusion. The combination of phytase and 3,000 LIPU/kg of lipase increased ileal and total tract phosphorus retention, and total tract Ca retention compared to the negative control. These incremental effects of lipase on top of phytase in absorption and utilization of calcium and phosphorus appear to be mainly related to the production of free fatty acids by lipase in the gastro intestinal tract, which promotes competition for calcium and improves phytase activity, as confirmed in in-vitro examples described herein.

The invention claimed is:

1. A feed supplement comprising a phytase and a lipolytic enzyme for increasing an uptake of at least one nutrient in a feedstuff to which the feed supplement is added, wherein said lipolytic enzyme has lipase activity at a pH in a range from pH 1.5 to pH 3.5.

2. The feed supplement according to claim 1 wherein said lipolytic enzyme comprises one or more of: a polypeptide having sequence of SEQ ID NO: 7 or SEQ ID NO: 8, or a polypeptide having at least 70% identity to SEQ ID NO: 7 or SEQ ID NO: 8; a polypeptide produced by expression of a nucleotide sequence comprising a sequence of SEQ ID NO: 9 or SEQ ID NO: 10; and a sequence having at least 70% identity to SEQ ID NO: 9 or SEQ ID NO: 10.

3. The feed supplement according to claim 1, wherein the lipolytic enzyme is produced in a *Trichoderma reesei* cell.

4. The feed supplement according to claim 1, wherein the phytase comprises one or more of an *E. coli* phytase having a sequence of SEQ ID NO: 13 and a *Buttiauxella* phytase having a sequence of one of SEQ ID NOs 1-6, or a polypeptide having at least 70% identity to one of SEQ ID NOs 1-6, or a polypeptide produced by expression of a nucleotide sequence comprising a sequence of SEQ ID NO: 11, or a sequence comprising nucleotides 253 to 1483 of SEQ ID NO:14, or a sequence that has at least 70% identity to SEQ ID NO: 11 or nucleotides 253 to 1483 of SEQ ID NO:14.

5. The feed supplement according to claim 1, wherein said phytase has phytase activity at a pH in a range from pH 2.5 to pH 5.5.

6. A feed supplement for increasing at least one nutrient in a feedstuff to which the feed supplement is added, the feed supplement comprising:
   i) a lipolytic enzyme comprising at least one of the following characteristics:
      a) a lipolytic enzyme that has lipase activity at a pH in a range from pH 1.5 to pH 3.5 when measured by a lipase assay;
      b) a lipolytic enzyme that comprises a polypeptide comprising an amino acid sequence of SEQ ID NO: 7 or SEQ ID NO: 8, or a polypeptide having at least 70% identity to SEQ ID NO: 7 or SEQ ID NO: 8; and
      c) a lipolytic enzyme produced by expression of a nucleotide sequence comprising a sequence of SEQ ID NO: 9 or SEQ ID NO: 10; or a sequence having at least 70% identity to SEQ ID NO: 9 or SEQ ID NO: 10; and
   ii) a phytase characterized by at least one of the following characteristics:
      a) a phytase that has phytase activity when measured at a pH in a range from pH 2.5 to pH 5.5;
      b) a phytase that comprises a polypeptide comprising an amino acid sequence of one of SEQ ID NOs: 1-6, or SEQ ID NO: 13, or a polypeptide having at least 70% identity to one of SEQ ID NOs 1-6 or SEQ ID NO: 13; and
      c) a phytase produced by expression of a nucleotide sequence comprising a sequence of SEQ ID NO: 11, or nucleotides 253 to 1483 of SEQ ID NO:14, or a sequence having at least 70% identity to SEQ ID NO: 11 or nucleotides 253 to 1483 of SEQ ID NO:14.

7. The feed supplement according to claim 6, wherein said phytase has phytase activity at a pH in a range from pH 5.0 to pH 5.5.

8. The feed supplement according to claim 6, wherein the phytase has a specific activity level of at least 100 FTU/mg.

9. The feed supplement according to claim 6, wherein the lipolytic enzyme has a specific activity level of at least 100 LIPU/mg.

10. The feed supplement according to claim 6, wherein the ratio of lipolytic enzyme to phytase is in a range from 1:3 to 12:1.

11. The feed supplement according to claim 6, further comprising at least one physiologically acceptable carrier.

12. The feed supplement according to claim 11, wherein the physiologically acceptable carrier is selected from at least one of maltodextrin, limestone (calcium carbonate), cyclodextrin, wheat or a wheat component, sucrose, starch, antifoam, $Na_2SO_4$, Talc, and PVA and mixtures thereof.

13. The feed supplement according to claim 6, wherein the feed supplement comprises at least one further feed enzyme.

14. The feed supplement according to claim 13, wherein the at least one further feed enzyme is selected from the group consisting of enzymes involved in starch metabolism, fibre degradation, and lipid metabolism, enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, galactosidases, glucanases, glucan lysases, endo-glucanases, glucoamylases, glucose oxidases, glucosidases, glucuronidases, hemicellulases, hexose oxidases, hydrolases, invertases, isomerases, laccases, lyases, mannosidases, oxidases, oxidoreductases, pectate lyases, pectin acetyl esterases, pectin depolymerases, pectin methyl esterases, pectinolytic enzymes, peroxidases, phenoloxidases, polygalacturonases, proteases, rhamno-galacturonases, ribonucleases, transferases, transglutaminases, xylanases, hexose oxidase (D-hexose: $0_2$-oxidoreductase, EC 1.1.3.5) β-glucanase, α-amylase, pectinase, cellobiohydrolase, acid phosphatases or combinations thereof.

15. The feed supplement according to claim 13, further comprising one or more of at least one xylanase and at least one amylase.

16. A feedstuff comprising the feed supplement according to claim 6, further comprising at least one low fibre feed material, wherein the at least one low fibre feed material is one of corn, wheat, an animal by-product meal, or soybean.

17. Use of A feed supplement comprising at least one phytase and at least one lipase having a lipase activity at a pH in a range from pH 1.5 to pH 3.5 for increasing an availability of at least one nutrient, increasing an available metabolic energy from a feed material, or increasing the availability of at least one nutrient and increasing the available metabolic energy from the feed material.

18. The feed supplement of claim 17, wherein the at least one nutrient is selected from one or more of phosphorous, calcium, amino acids, fat, and starch.

19. A feedstuff comprising the feed supplement according to claim 17, further comprising at least one low fibre feed material, wherein the at least one low fibre feed material is one of corn, wheat, an animal by-product meal, or soybean.

* * * * *

SEQUENCE LISTING

<160> NUMBER OF SEQ ID NOS: 33

<210> SEQ ID NO 1
<211> LENGTH: 413
<212> TYPE: PRT
<213> ORGANISM: Buttiauxella sp.

<400> SEQUENCE: 1

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr

```
            50                  55                  60
Arg Gln Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
            115                 120                 125

Pro Val Lys Ala Gly Thr Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
            195                 200                 205

Ala Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
            290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 2
<211> LENGTH: 413
<212> TYPE: PRT
<213> ORGANISM: Buttiauxella sp.

<400> SEQUENCE: 2

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
```

```
                20                  25                  30
Asp Val Thr Pro Tyr Thr Trp Pro Glu Trp Pro Val Lys Leu Gly Tyr
                35                  40                  45
Ile Thr Pro Arg Gly Glu His Leu Ile Ser Leu Met Gly Gly Phe Tyr
 50                  55                  60
Arg Gln Lys Phe Gln Gln Gly Ile Leu Pro Gln Gly Ser Cys Pro
 65                  70                  75                  80
Thr Pro Asn Ser Ile Tyr Val Trp Thr Asp Val Ala Gln Arg Thr Leu
                85                  90                  95
Lys Thr Gly Glu Ala Phe Leu Ala Gly Leu Ala Pro Gln Cys Gly Leu
                100                 105                 110
Thr Ile His His Gln Gln Asn Leu Glu Lys Ala Asp Pro Leu Phe His
                115                 120                 125
Pro Val Lys Ala Gly Ile Cys Ser Met Asp Lys Thr Gln Val Gln Gln
                130                 135                 140
Ala Val Glu Lys Glu Ala Gln Thr Pro Ile Asp Asn Leu Asn Gln Arg
145                 150                 155                 160
Tyr Ile Pro Glu Leu Ala Leu Met Asn Thr Val Leu Asn Phe Ser Lys
                165                 170                 175
Ser Pro Trp Cys Gln Lys His Ser Ala Asp Lys Pro Cys Asp Leu Ala
                180                 185                 190
Leu Ser Met Pro Ser Arg Leu Ser Ile Lys Asp Asn Gly Asn Glu Val
                195                 200                 205
Ser Leu Asp Gly Ala Ile Gly Leu Ser Ser Thr Leu Ala Glu Ile Phe
                210                 215                 220
Leu Leu Glu Tyr Ala Gln Gly Met Pro Gln Ala Ala Trp Gly Asn Ile
225                 230                 235                 240
His Ser Glu Gln Glu Trp Ala Leu Leu Leu Lys Leu His Asn Val Tyr
                245                 250                 255
Phe Asp Leu Met Glu Arg Thr Pro Tyr Ile Ala Arg His Lys Gly Thr
                260                 265                 270
Pro Leu Leu Gln Ala Ile Ser Asn Ala Leu Asn Pro Asn Ala Thr Glu
                275                 280                 285
Ser Lys Leu Pro Asp Ile Ser Pro Asp Asn Lys Ile Leu Phe Ile Ala
                290                 295                 300
Gly His Asp Thr Asn Ile Ala Asn Ile Ala Gly Met Leu Asn Met Arg
305                 310                 315                 320
Trp Thr Leu Pro Gly Gln Pro Asp Asn Thr Pro Pro Gly Gly Ala Leu
                325                 330                 335
Val Phe Glu Arg Leu Ala Asp Lys Ser Gly Lys Gln Tyr Val Ser Val
                340                 345                 350
Ser Met Val Tyr Gln Thr Leu Glu Gln Leu Arg Ser Gln Thr Pro Leu
                355                 360                 365
Ser Leu Asn Gln Pro Pro Gly Ser Val Gln Leu Lys Ile Pro Gly Cys
                370                 375                 380
Asn Asp Gln Thr Ala Glu Gly Tyr Cys Pro Leu Ser Thr Phe Thr Arg
385                 390                 395                 400
Val Val Ser Gln Ser Val Glu Pro Gly Cys Gln Leu Gln
                405                 410

<210> SEQ ID NO 3
<211> LENGTH: 413
<212> TYPE: PRT
<213> ORGANISM: Buttiauxella sp.
```

```
<400> SEQUENCE: 3

Asn Asp Thr Pro Ala Ser Gly Tyr Gln Val Glu Lys Val Val Ile Leu
  1               5                  10                  15

Ser Arg His Gly Val Arg Ala Pro Thr Lys Met Thr Gln Thr Met Arg
             20                  25                  30

Asp Val Thr Pro Asn Thr Trp Pro Glu Trp Pro Val Lys Leu Gly Tyr
         35                  40                  45

Ile Thr Pro Arg Gly Glu His Leu Ile Ser Leu Met Gly Gly Phe Tyr
     50                  55                  60

Arg Gln Lys Phe Gln Gln Gly Ile Leu Ser Gln Gly Ser Cys Pro
 65                  70                  75                  80

Thr Pro Asn Ser Ile Tyr Val Trp Thr Asp Val Ala Gln Arg Thr Leu
                 85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

```
<210> SEQ ID NO 4
<211> LENGTH: 413
<212> TYPE: PRT
<213> ORGANISM: Buttiauxella sp.

<400> SEQUENCE: 4

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Ser Gln Ser Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln Arg
145                 150                 155                 160

Tyr Ile Pro Glu Leu Ala Leu Met Asn Thr Val Leu Asn Phe Ser Lys
                165                 170                 175

Ser Pro Trp Cys Gln Lys His Ser Ala Asp Lys Pro Cys Asp Leu Ala
            180                 185                 190

Leu Ser Met Pro Ser Arg Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Pro Gly Ser Val Gln Leu Lys Ile Pro Gly Cys
    370                 375                 380
```

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 5
<211> LENGTH: 413
<212> TYPE: PRT
<213> ORGANISM: Buttiauxella sp.

<400> SEQUENCE: 5

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Tyr Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Pro Arg Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
130                 135                 140

Ala Val Glu Lys Glu Ala Gln Thr Pro Ile Asp Asn Leu Asn Gln Arg
145                 150                 155                 160

Tyr Ile Pro Glu Leu Ala Leu Met Asn Thr Ile Leu Asn Phe Ser Lys
                165                 170                 175

Ser Pro Trp Cys Gln Lys His Ser Ala Asp Lys Pro Cys Asp Leu Ala
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
210                 215                 220

Leu Leu Glu Tyr Ala Gln Gly Met Pro Gln Val Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

```
Ser Met Val Tyr Gln Thr Leu Glu Gln Leu Arg Ser Gln Thr Pro Leu
        355                 360                 365

Ser Leu Asn Gln Pro Pro Gly Ser Val Gln Leu Lys Ile Pro Gly Cys
        370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 6
<211> LENGTH: 419
<212> TYPE: PRT
<213> ORGANISM: Buttiauxella sp.

<400> SEQUENCE: 6

His His His His His Asn Asp Thr Pro Ala Ser Gly Tyr Gln Val
1               5                   10                  15

Glu Lys Val Val Ile Leu Ser Arg His Gly Val Arg Ala Pro Thr Lys
                20                  25                  30

Met Thr Gln Thr Met Arg Asp Val Thr Pro Asn Thr Trp Pro Glu Trp
            35                  40                  45

Pro Val Lys Leu Gly Tyr Ile Thr Pro Arg Gly Glu His Leu Ile Ser
        50                  55                  60

Leu Met Gly Gly Phe Tyr Arg Gln Lys Phe Gln Gln Gly Ile Leu
65                  70                  75                  80

Ser Gln Gly Ser Cys Pro Thr Pro Asn Ser Ile Tyr Val Trp Thr Asp
                85                  90                  95

Val Asp Gln Arg Thr Leu Lys Thr Gly Glu Ala Phe Leu Ala Gly Leu
                100                 105                 110

Ala Pro Gln Cys Gly Leu Thr Ile His His Gln Gln Asn Leu Glu Lys
            115                 120                 125

Ala Asp Pro Leu Phe His Pro Val Lys Ala Gly Ile Cys Ser Met Asp
        130                 135                 140

Lys Thr Gln Val Gln Gln Ala Val Glu Lys Glu Ala Gln Thr Pro Ile
145                 150                 155                 160

Asp Asn Leu Asn Gln His Tyr Ile Pro Ser Leu Ala Leu Met Asn Thr
                165                 170                 175

Thr Leu Asn Phe Ser Lys Ser Pro Trp Cys Gln Lys His Ser Ala Asp
            180                 185                 190

Lys Ser Cys Asp Leu Gly Leu Ser Met Pro Ser Lys Leu Ser Ile Lys
        195                 200                 205

Asp Asn Gly Asn Glu Val Ser Leu Asp Gly Ala Ile Gly Leu Ser Ser
    210                 215                 220

Thr Leu Ala Glu Ile Phe Leu Leu Glu Tyr Ala Gln Gly Met Pro Gln
225                 230                 235                 240

Ala Ala Trp Gly Asn Ile His Ser Glu Gln Glu Trp Ala Leu Leu Leu
                245                 250                 255

Lys Leu His Asn Val Tyr Phe Asp Leu Met Glu Arg Thr Pro Tyr Ile
            260                 265                 270

Ala Arg His Lys Gly Thr Pro Leu Leu Gln Ala Ile Ser Asn Ala Leu
        275                 280                 285

Asn Pro Asn Ala Thr Glu Ser Lys Leu Pro Asp Ile Ser Pro Asp Asn
    290                 295                 300

Lys Ile Leu Phe Ile Ala Gly His Asp Thr Asn Ile Ala Asn Ile Ala
305                 310                 315                 320
```

```
Gly Met Leu Asn Met Arg Trp Thr Leu Pro Gly Gln Pro Asp Asn Thr
            325                 330                 335

Pro Pro Gly Gly Ala Leu Val Phe Glu Arg Leu Ala Asp Lys Ser Gly
        340                 345                 350

Lys Gln Tyr Val Ser Val Ser Met Val Tyr Gln Thr Leu Glu Gln Leu
        355                 360                 365

Arg Ser Gln Thr Pro Leu Ser Leu Asn Gln Pro Ala Gly Ser Val Gln
    370                 375                 380

Leu Lys Ile Pro Gly Cys Asn Asp Gln Thr Ala Glu Gly Tyr Cys Pro
385                 390                 395                 400

Leu Ser Thr Phe Thr Arg Val Val Ser Gln Ser Val Glu Pro Gly Cys
                405                 410                 415

Gln Leu Gln

<210> SEQ ID NO 7
<211> LENGTH: 297
<212> TYPE: PRT
<213> ORGANISM: Aspergillus tubingensis

<400> SEQUENCE: 7

Met Phe Ser Gly Arg Phe Gly Val Leu Leu Thr Ala Leu Ala Ala Leu
1               5                   10                  15

Gly Ala Ala Pro Ala Pro Leu Ala Val Arg Ser Val Ser Thr Ser
            20                  25                  30

Thr Leu Asp Glu Leu Gln Leu Phe Ala Gln Trp Ser Ala Ala Ala Tyr
        35                  40                  45

Cys Ser Asn Asn Ile Asp Ser Lys Asp Ser Asn Leu Thr Cys Thr Ala
    50                  55                  60

Asn Ala Cys Pro Ser Val Glu Glu Ala Ser Thr Thr Met Leu Leu Glu
65                  70                  75                  80

Phe Asp Leu Thr Asn Asp Phe Gly Gly Thr Ala Gly Phe Leu Ala Ala
                85                  90                  95

Asp Asn Thr Asn Lys Arg Leu Val Val Ala Phe Arg Gly Ser Ser Thr
            100                 105                 110

Ile Glu Asn Trp Ile Ala Asn Leu Asp Phe Ile Leu Glu Asp Asn Asp
        115                 120                 125

Asp Leu Cys Thr Gly Cys Lys Val His Thr Gly Phe Trp Lys Ala Trp
    130                 135                 140

Glu Ser Ala Ala Asp Glu Leu Thr Ser Lys Ile Lys Ser Ala Met Ser
145                 150                 155                 160

Thr Tyr Ser Gly Tyr Thr Leu Tyr Phe Thr Gly His Ser Leu Gly Gly
                165                 170                 175

Ala Leu Ala Thr Leu Gly Ala Thr Val Leu Arg Asn Asp Gly Tyr Ser
            180                 185                 190

Val Glu Leu Tyr Thr Tyr Gly Cys Pro Arg Ile Gly Asn Tyr Ala Leu
        195                 200                 205

Ala Glu His Ile Thr Ser Gln Gly Ser Gly Ala Asn Phe Arg Val Thr
    210                 215                 220

His Leu Asn Asp Ile Val Pro Arg Val Pro Pro Met Asp Phe Gly Phe
225                 230                 235                 240

Ser Gln Pro Ser Pro Glu Tyr Trp Ile Thr Ser Gly Asn Gly Ala Ser
                245                 250                 255

Val Thr Ala Ser Asp Ile Glu Val Ile Glu Gly Ile Asn Ser Thr Ala
            260                 265                 270

Gly Asn Ala Gly Glu Ala Thr Val Ser Val Val Ala His Leu Trp Tyr
```

```
                   275                 280                 285

Phe Phe Ala Ile Ser Glu Cys Leu Leu
        290                 295

<210> SEQ ID NO 8
<211> LENGTH: 270
<212> TYPE: PRT
<213> ORGANISM: Aspergillus tubingensis

<400> SEQUENCE: 8

Ser Val Ser Thr Ser Thr Leu Asp Glu Leu Gln Leu Phe Ala Gln Trp
1               5                   10                  15

Ser Ala Ala Ala Tyr Cys Ser Asn Asn Ile Asp Ser Lys Asp Ser Asn
            20                  25                  30

Leu Thr Cys Thr Ala Asn Ala Cys Pro Ser Val Glu Glu Ala Ser Thr
        35                  40                  45

Thr Met Leu Leu Glu Phe Asp Leu Thr Asn Asp Phe Gly Gly Thr Ala
    50                  55                  60

Gly Phe Leu Ala Ala Asp Asn Thr Asn Lys Arg Leu Val Val Ala Phe
65                  70                  75                  80

Arg Gly Ser Ser Thr Ile Glu Asn Trp Ile Ala Asn Leu Asp Phe Ile
                85                  90                  95

Leu Glu Asp Asn Asp Asp Leu Cys Thr Gly Cys Lys Val His Thr Gly
            100                 105                 110

Phe Trp Lys Ala Trp Glu Ser Ala Ala Asp Glu Leu Thr Ser Lys Ile
        115                 120                 125

Lys Ser Ala Met Ser Thr Tyr Ser Gly Tyr Thr Leu Tyr Phe Thr Gly
    130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
                165                 170                 175

Gly Asn Tyr Ala Leu Ala Glu His Ile Thr Ser Gln Gly Ser Gly Ala
            180                 185                 190

Asn Phe Arg Val Thr His Leu Asn Asp Ile Val Pro Arg Val Pro Pro
        195                 200                 205

Met Asp Phe Gly Phe Ser Gln Pro Ser Pro Glu Tyr Trp Ile Thr Ser
    210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Val
                245                 250                 255

Ala His Leu Trp Tyr Phe Phe Ala Ile Ser Glu Cys Leu Leu
            260                 265                 270

<210> SEQ ID NO 9
<211> LENGTH: 1045
<212> TYPE: DNA
<213> ORGANISM: Aspergillus tubingensis

<400> SEQUENCE: 9
atgttctctg acggtttgg agtgcttttg acagcgcttg ctgcgctggg tgctgccgcg      60
ccggcaccgc ttgctgtgcg gagtaggtgt gcccgatgtg agatggttgg atagcactga    120
tgaagggtga ataggtgtct cgacttccac gttggatgag ttgcaattgt tcgcgcaatg    180
gtctgccgca gcttattgct cgaataatat cgactcgaaa gactccaact tgacatgcac    240
```

```
ggccaacgcc tgtccatcag tcgaggaggc cagtaccacg atgctgctgg agttcgacct    300
gtatgtcact cagatcgcag acatagagca cagctaattt gaacaggacg aacgactttg    360
gaggcacagc cggtttcctg ccgcggaca acaccaacaa gcggctcgtg gtcgccttcc    420
ggggaagcag cacgattgag aactggattg ctaatcttga cttcatcctg aagataacg     480 acgacctctg caccggctgc aaggtccata ctggtttctg aaggcatgg gagtccgctg     540 ccgacgaact gacgagcaag atcaagtctg cgatgagcac gtattcgggc tatacccta    600 acttcaccgg gcacagtttg gcggcgcat tggctacgct gggagcgaca gttctgcgaa     660
atgacggata tagcgttgag ctggtgagtc cttcacaaag gtgatggagc gacaatcggg    720
ttctgacagt caatagtaca cctatggatg tcctcgaatc ggaaactatg cgctggctga    780
gcatatcacc agtcagggat ctggggccaa cttccgtgtt acacacttga acgacatcgt    840 ccccccgggtg ccacccatgg actttggatt cagtcagcca gtccggaat actggatcac    900 cagtggcaat ggagccagtg tcacggcgtc ggatatcgaa gtcatcgagg gaatcaattc    960
aacggcggga atgcaggcg aagcaacggt gagcgttgtg gctcacttgt ggtactttt     1020 tgcgatttcc gagtgcctgc tataa                                         1045

<210> SEQ ID NO 10
<211> LENGTH: 964
<212> TYPE: DNA
<213> ORGANISM: Aspergillus tubingensis

<400> SEQUENCE: 10
agtaggtgtg cccgatgtga gatggttgga tagcactgat gaagggtgaa taggtgtctc     60
gacttccacg ttggatgagt tgcaattgtt cgcgcaatgg tctgccgcag cttattgctc    120
gaataatatc gactcgaaag actccaactt gacatgcacg ccaacgcct gtccatcagt    180 cgaggaggcc agtaccacga tgctgctgga gttcgacctg tatgtcactc agatcgcaga    240
catagagcac agctaatttg aacaggacga acgactttgg aggcacagcc ggtttcctgg    300
ccgcggacaa caccaacaag cggctcgtgg tcgccttccg ggggaagcag cacgattgaga   360 actggattgc taatcttgac ttcatcctgg aagataacga cgacctctgc accggctgca    420
aggtccatac tggtttctgg aaggcatggg agtccgctgc cgacgaactg acgagcaaga    480
tcaagtctgc gatgagcacg tattcgggct atacccctata cttcaccggg cacagtttgg   540
gcggcgcatt ggctacgctg ggagcgacag ttctgcgaaa tgacggata tagcgttgagc   600 tggtgagtcc ttcacaaagg tgatggagcg acaatcgggt tctgacagtc aatagtacac    660
ctatggatgt cctcgaatcg gaaactatgc gctggctgag catatcacca gtcagggatc    720
tggggccaac ttccgtgtta cacacttgaa cgacatcgtc ccccgggtgc cacccatgga    780
ctttggattc agtcagccaa gtccggaata ctggatcacc agtggcaatg gagccagtgt    840
cacggcgtcg gatatcgaag tcatcgaggg aatcaattca acggcggaa atgcaggcga    900 agcaacggtg agcgttgtgg ctcacttgtg gtactttttt gcgatttccg agtgcctgct    960
ataa                                                                964

<210> SEQ ID NO 11
<211> LENGTH: 1242
<212> TYPE: DNA
<213> ORGANISM: Buttiauxella sp.
<220> FEATURE:
<221> NAME/KEY: misc_feature
<222> LOCATION: (1176)..(1176)
<223> OTHER INFORMATION: n is a, c, g, or t
<220> FEATURE:
```

```
<221> NAME/KEY: misc_feature
<222> LOCATION: (1202)..(1202)
<223> OTHER INFORMATION: n is a, c, g, or t

<400> SEQUENCE: 11
aacgacactc ccgcttcagg ctaccaggtt gagaaagtgg taatactcag ccgccacggg      60
gtgcgagcac caaccaaaat gacacagacc atgcgcgacg taacacctaa tacctggccc     120
gaatggccag taaaattggg ttatatcacg ccacgcggtg agcatctgat tagcctgatg     180
ggcgggtttt atcgccagaa gtttcaacaa cagggcattt tatcgcaggg cagttgcccc     240
acaccaaact caatttatgt ctgggcagac gttgatcagc gcacgcttaa aactggcgaa     300
gctttcctgg cagggcttgc tccggaatgt catttaacta ttcaccacca gcaggacatc     360
aaaaaagccg atccgctgtt ccatccggtg aaagcgggca cctgttcaat ggataaaact     420
caggtccaac aggccgttga aaagaagct caaaccccca ttgataatct gaatcagcac      480
tatattccct ttctggcctt gatgaatacg accctcaact tttcgacgtc ggcctggtgt     540
cagaaacaca gcgcggataa aagctgtgat ttagggctat ccatgccgag caagctgtcg     600
ataaaagata atggcaacaa agtcgctctc gacggggcca ttggcctttc gtctacgctt     660
gctgaaattt tcctgctgga atatgcgcaa gggatgccgc aagcggcgtg ggggaatatt     720
cattcagagc aagagtgggc gtcgctactg aaactgcata acgtccagtt tgatttgatg     780
gcacgcacgc cttatatcgc cagacataac ggcacgcctt tattgcaggc catcagcaac     840
gcgctgaacc cgaatgccac cgaaagcaaa ctgcctgata tctcacctga caataagatc     900
ctgtttattg ccggacacga taccaatatt gccaatatcg caggcatgct caacatgcgc     960
tggacgctac ctgggcaacc cgataacacc cctccgggcg gcgctttagt cttgagcgt    1020
ttggccgata agtcagggaa acaatatgtt agcgtgagca tggtgtatca gactctcgag    1080
cagttgcgct cccaaacacc acttagcctt aatcaacctg cgggaagcgt acagctaaaa    1140
attcctggct gtaacgatca gacggctgaa ggatantgcc cgctgtcgac gttcactcgc    1200
gnggttagcc aaagcgtgga accaggctgc cagctacagt aa                      1242

<210> SEQ ID NO 12
<211> LENGTH: 432
<212> TYPE: PRT
<213> ORGANISM: Escherichia coli

<400> SEQUENCE: 12

Met Lys Ala Ile Leu Ile Pro Phe Leu Ser Leu Ile Pro Leu Thr
1               5                   10                  15

Pro Gln Ser Ala Phe Ala Gln Ser Glu Pro Glu Leu Lys Leu Glu Ser
                20                  25                  30

Val Val Ile Val Ser Arg His Gly Val Arg Ala Pro Thr Lys Ala Thr
            35                  40                  45

Gln Leu Met Gln Asp Val Thr Pro Asp Ala Trp Pro Thr Trp Pro Val
        50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125
```

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Lys Thr Ala Leu Thr Pro His
290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Arg Leu Ser Asp Asn Ser Gln
        355                 360                 365

Trp Ile Gln Val Ser Leu Val Phe Gln Thr Leu Gln Gln Met Arg Asp
370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

<210> SEQ ID NO 13
<211> LENGTH: 410
<212> TYPE: PRT
<213> ORGANISM: Escherichia coli

<400> SEQUENCE: 13

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                    85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
        130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gly Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 14
<211> LENGTH: 1901
<212> TYPE: DNA
<213> ORGANISM: Escherichia coli
<220> FEATURE:
<221> NAME/KEY: CDS
<222> LOCATION: (16)..(108)
<220> FEATURE:
<221> NAME/KEY: CDS
<222> LOCATION: (188)..(1486)
<220> FEATURE:
<221> NAME/KEY: misc_feature
<222> LOCATION: (403)..(403)
<223> OTHER INFORMATION: n is a, c, g, or t

<400> SEQUENCE: 14

```
taaggagcag aaaca atg tgg tat tta ctt tgg ttc gtc ggc att ttg ttg        51
               Met Trp Tyr Leu Leu Trp Phe Val Gly Ile Leu Leu
                 1               5                  10 atg tgt tcg ctc tcc acc ctt gtg ttg gta tgg ctg gac ccg cgt ctg         99
Met Cys Ser Leu Ser Thr Leu Val Leu Val Trp Leu Asp Pro Arg Leu
         15                  20                  25 aaa agt taa cgaacgtagg cctgatgcgg cgcattagca tcgcatcagg                148
Lys Ser
     30 caatcaataa tgtcagatat gaaaagcgga acatatcg atg aaa gcg atc tta          202
                                          Met Lys Ala Ile Leu
                                                         35 atc cca ttt tta tct ctt ctg att ccg tta acc ccg caa tct gca ttc        250
Ile Pro Phe Leu Ser Leu Leu Ile Pro Leu Thr Pro Gln Ser Ala Phe
                 40                  45                  50 gct cag agt gag ccg gag ctg aag ctg gaa agt gtg gtg att gtc agt        298
Ala Gln Ser Glu Pro Glu Leu Lys Leu Glu Ser Val Val Ile Val Ser
             55                  60                  65 cgt cat ggt gtg cgt gct cca acc aag gcc acg caa ctg atg cag gat        346
Arg His Gly Val Arg Ala Pro Thr Lys Ala Thr Gln Leu Met Gln Asp
         70                  75                  80 gtc acc cca gac gca tgg cca acc tgg ccg gta aaa ctg ggt tgg ctg        394
Val Thr Pro Asp Ala Trp Pro Thr Trp Pro Val Lys Leu Gly Trp Leu
     85                  90                  95 aca ccg cgn ggt ggt gag cta atc gcc tat ctc gga cat tac caa cgc        442
Thr Pro Arg Gly Gly Glu Leu Ile Ala Tyr Leu Gly His Tyr Gln Arg
100                 105                 110                 115 cag cgt ctg gta gcc gac gga ttg ctg gcg aaa aag ggc tgc ccg cag        490
Gln Arg Leu Val Ala Asp Gly Leu Leu Ala Lys Lys Gly Cys Pro Gln
                120                 125                 130 tct ggt cag gtc gcg att att gct gat gtc gac gag cgt acc cgt aaa        538
Ser Gly Gln Val Ala Ile Ile Ala Asp Val Asp Glu Arg Thr Arg Lys
            135                 140                 145 aca ggc gaa gcc ttc gcc gcc ggg ctg gca cct gac tgt gca ata acc        586
Thr Gly Glu Ala Phe Ala Ala Gly Leu Ala Pro Asp Cys Ala Ile Thr
        150                 155                 160 gta cat acc cag gca gat acg tcc agt ccc gat ccg tta ttt aat cct        634
Val His Thr Gln Ala Asp Thr Ser Ser Pro Asp Pro Leu Phe Asn Pro
    165                 170                 175 cta aaa act ggc gtt tgc caa ctg gat aac gcg aac gtg act gac gcg        682
Leu Lys Thr Gly Val Cys Gln Leu Asp Asn Ala Asn Val Thr Asp Ala
180                 185                 190                 195 atc ctc agc agg gca gga ggg tca att gct gac ttt acc ggg cat cgg        730
Ile Leu Ser Arg Ala Gly Gly Ser Ile Ala Asp Phe Thr Gly His Arg
                200                 205                 210 caa acg gcg ttt cgc gaa ctg gaa cgg gtg ctt aat ttt ccg caa tca        778
Gln Thr Ala Phe Arg Glu Leu Glu Arg Val Leu Asn Phe Pro Gln Ser
            215                 220                 225 aac ttg tgc ctt aaa cgt gag aaa cag gac gaa agc tgt tca tta acg        826
Asn Leu Cys Leu Lys Arg Glu Lys Gln Asp Glu Ser Cys Ser Leu Thr
        230                 235                 240 cag gca tta cca tcg gaa ctc aag gtg agc gcc gac aat gtc tca tta        874
Gln Ala Leu Pro Ser Glu Leu Lys Val Ser Ala Asp Asn Val Ser Leu
    245                 250                 255 acc ggt gcg gta agc ctc gca tca atg ctg acg gag ata ttt ctc ctg        922
Thr Gly Ala Val Ser Leu Ala Ser Met Leu Thr Glu Ile Phe Leu Leu
260                 265                 270                 275 caa caa gca cag gga atg ccg gag ccg ggg tgg gga agg atc acc gat        970
Gln Gln Ala Gln Gly Met Pro Glu Pro Gly Trp Gly Arg Ile Thr Asp
                280                 285                 290
```

```
tca cac cag tgg aac acc ttg cta agt ttg cat aac gcg caa ttt tat    1018
Ser His Gln Trp Asn Thr Leu Leu Ser Leu His Asn Ala Gln Phe Tyr
            295                 300                 305 ttg cta caa cgc acg cca gag gtt gcc cgc agc cgc gcc acc ccg tta    1066
Leu Leu Gln Arg Thr Pro Glu Val Ala Arg Ser Arg Ala Thr Pro Leu
310                 315                 320 tta gat ttg atc aag aca gcg ttg acg ccc cat cca ccg caa aaa cag    1114
Leu Asp Leu Ile Lys Thr Ala Leu Thr Pro His Pro Pro Gln Lys Gln
    325                 330                 335 gcg tat ggt gtg aca tta ccc act tca gtg ctg ttt atc gcc gga cac    1162
Ala Tyr Gly Val Thr Leu Pro Thr Ser Val Leu Phe Ile Ala Gly His
340                 345                 350                 355 gat act aat ctg gca aat ctc ggc ggc gca ctg gag ctc aac tgg acg    1210
Asp Thr Asn Leu Ala Asn Leu Gly Gly Ala Leu Glu Leu Asn Trp Thr
                360                 365                 370 ctt ccc ggt cag ccg gat aac acg ccg cca ggt ggt gaa ctg gtg ttt    1258
Leu Pro Gly Gln Pro Asp Asn Thr Pro Pro Gly Gly Glu Leu Val Phe
            375                 380                 385 gaa cgc tgg cgt cgg cta agc gat aac agc cag tgg att cag gtt tcg    1306
Glu Arg Trp Arg Arg Leu Ser Asp Asn Ser Gln Trp Ile Gln Val Ser
390                 395                 400 ctg gtc ttc cag act tta cag cag atg cgt gat aaa acg ccg ctg tca    1354
Leu Val Phe Gln Thr Leu Gln Gln Met Arg Asp Lys Thr Pro Leu Ser
    405                 410                 415 tta aat acg ccg ccc gga gag gtg aaa ctg acc ctg gca gga tgt gaa    1402
Leu Asn Thr Pro Pro Gly Glu Val Lys Leu Thr Leu Ala Gly Cys Glu
420                 425                 430                 435 gag cga aat gcg cag ggc atg tgt tcg ttg gca ggt ttt acg caa atc    1450
Glu Arg Asn Ala Gln Gly Met Cys Ser Leu Ala Gly Phe Thr Gln Ile
                440                 445                 450 gtg aat gaa gca cgc ata ccg gcg tgc agt ttg taa tgcataaaaa         1496
Val Asn Glu Ala Arg Ile Pro Ala Cys Ser Leu
            455                 460 agagcattca gttacctgaa tgctctgagg ctgatgacaa acgaagaact gtctaatgcg    1556
tagaccggaa aaggcgttca cgccgcatcc ggccactttc agttttcctc tttctcggag    1616
taactataac cgtaatagtt atagccgtaa ctgtaagcgg tgctggcgcg tttaatcaca    1676
ccattgagga tagcgccttt aatattgacg cctgcctgtt ccagacgctg cattgacaaa    1736
ctcacctctt tggcggtgtt caagccaaaa cgcgcaacca gcaggctggt gccaacagaa    1796
cgccccacga ccgcggcatc actcaccgcc agcatcggcg gcgtatcgac aatcaccaga    1856
tcgtaatggt cgttcgccca ttccagtaat tgacgcatcc gatcg                    1901

<210> SEQ ID NO 15
<211> LENGTH: 30
<212> TYPE: PRT
<213> ORGANISM: Escherichia coli

<400> SEQUENCE: 15

Met Trp Tyr Leu Leu Trp Phe Val Gly Ile Leu Leu Met Cys Ser Leu
1               5                   10                  15

Ser Thr Leu Val Leu Val Trp Leu Asp Pro Arg Leu Lys Ser
            20                  25                  30

<210> SEQ ID NO 16
<211> LENGTH: 432
<212> TYPE: PRT
<213> ORGANISM: Escherichia coli

<400> SEQUENCE: 16
```

```
Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
                20                  25                  30

Val Val Ile Val Ser Arg His Gly Val Arg Ala Pro Thr Lys Ala Thr
            35                  40                  45

Gln Leu Met Gln Asp Val Thr Pro Asp Ala Trp Pro Thr Trp Pro Val
50                      55                  60

Lys Leu Gly Trp Leu Thr Pro Arg Gly Gly Glu Leu Ile Ala Tyr Leu
65                      70                  75                  80

Gly His Tyr Gln Arg Gln Arg Leu Val Ala Asp Gly Leu Leu Ala Lys
                85                  90                  95

Lys Gly Cys Pro Gln Ser Gly Val Ala Ile Ile Ala Asp Val Asp
                100                 105                 110

Glu Arg Thr Arg Lys Thr Gly Glu Ala Phe Ala Ala Gly Leu Ala Pro
                115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
                180                 185                 190

Asn Phe Pro Gln Ser Asn Leu Cys Leu Lys Arg Glu Lys Gln Asp Glu
                195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Tyr Leu Leu Gln Arg Thr Pro Glu Val Ala Arg Ser
                275                 280                 285

Arg Ala Thr Pro Leu Leu Asp Leu Ile Lys Thr Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
                340                 345                 350

Gly Glu Leu Val Phe Glu Arg Trp Arg Arg Leu Ser Asp Asn Ser Gln
                355                 360                 365

Trp Ile Gln Val Ser Leu Val Phe Gln Thr Leu Gln Gln Met Arg Asp
370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
```

<210> SEQ ID NO 17
<211> LENGTH: 398
<212> TYPE: PRT
<213> ORGANISM: Homo sapiens

<400> SEQUENCE: 17

Met Trp Leu Leu Leu Thr Met Ala Ser Leu Ile Ser Val Leu Gly Thr
1               5                   10                  15

Thr His Gly Leu Phe Gly Lys Leu His Pro Gly Ser Pro Glu Val Thr
            20                  25                  30

Met Asn Ile Ser Gln Met Ile Thr Tyr Trp Gly Tyr Pro Asn Glu Glu
        35                  40                  45

Tyr Glu Val Val Thr Glu Asp Gly Tyr Ile Leu Glu Val Asn Arg Ile
    50                  55                  60

Pro Tyr Gly Lys Lys Asn Ser Gly Asn Thr Gly Gln Arg Pro Val Val
65                  70                  75                  80

Phe Leu Gln His Gly Leu Leu Ala Ser Ala Thr Asn Trp Ile Ser Asn
                85                  90                  95

Leu Pro Asn Asn Ser Leu Ala Phe Ile Leu Ala Asp Ala Gly Tyr Asp
            100                 105                 110

Val Trp Leu Gly Asn Ser Arg Gly Asn Thr Trp Ala Arg Arg Asn Leu
        115                 120                 125

Tyr Tyr Ser Pro Asp Ser Val Glu Phe Trp Ala Phe Ser Phe Asp Glu
    130                 135                 140

Met Ala Lys Tyr Asp Leu Pro Ala Thr Ile Asp Phe Ile Val Lys Lys
145                 150                 155                 160

Thr Gly Gln Lys Gln Leu His Tyr Val Gly His Ser Gln Gly Thr Thr
                165                 170                 175

Ile Gly Phe Ile Ala Phe Ser Thr Asn Pro Ser Leu Ala Lys Arg Ile
            180                 185                 190

Lys Thr Phe Tyr Ala Leu Ala Pro Val Ala Thr Val Lys Tyr Thr Lys
        195                 200                 205

Ser Leu Ile Asn Lys Leu Arg Phe Val Pro Gln Ser Leu Phe Lys Phe
    210                 215                 220

Ile Phe Gly Asp Lys Ile Phe Tyr Pro His Asn Phe Asp Gln Phe
225                 230                 235                 240

Leu Ala Thr Glu Val Cys Ser Arg Glu Met Leu Asn Leu Leu Cys Ser
                245                 250                 255

Asn Ala Leu Phe Ile Ile Cys Gly Phe Asp Ser Lys Asn Phe Asn Thr
            260                 265                 270

Ser Arg Leu Asp Val Tyr Leu Ser His Asn Pro Ala Gly Thr Ser Val
        275                 280                 285

Gln Asn Met Phe His Trp Thr Gln Ala Val Lys Ser Gly Lys Phe Gln
    290                 295                 300

Ala Tyr Asp Trp Gly Ser Pro Val Gln Asn Arg Met His Tyr Asp Gln
305                 310                 315                 320

Ser Gln Pro Pro Tyr Tyr Asn Val Thr Ala Met Asn Val Pro Ile Ala
                325                 330                 335

Val Trp Asn Gly Gly Lys Asp Leu Leu Ala Asp Pro Gln Asp Val Gly
            340                 345                 350

Leu Leu Leu Pro Lys Leu Pro Asn Leu Ile Tyr His Lys Glu Ile Pro
        355                 360                 365

Phe Tyr Asn His Leu Asp Phe Ile Trp Ala Met Asp Ala Pro Gln Glu

```
                370             375             380
Val Tyr Asn Asp Ile Val Ser Met Ile Ser Glu Asp Lys Lys
385                 390                 395
```

<210> SEQ ID NO 18
<211> LENGTH: 1197
<212> TYPE: DNA
<213> ORGANISM: Homo sapiens

<400> SEQUENCE: 18

```
atgtggctgc ttttaacaat ggcaagtttg atatctgtac tggggactac acatggtttg     60
tttggaaaat tacatcctgg aagccctgaa gtgactatga acattagtca gatgattact    120
tattggggat acccaaatga agaatatgaa gttgtgactg aagatggtta tattcttgaa    180
gtcaatagaa ttccttatgg gagaaaaaat tcagggaata caggccagag acctgttgtg    240
tttttgcagc atggtttgct tgcatcagcc acaaactgga tttccaacct gccgaacaac    300
agccttgcct tcattctggc agatgctggt tatgatgtgt ggctgggcaa cagcagagga    360
aacacctggg ccagaagaaa cttgtactat tcaccagatt cagttgaatt ctgggctttc    420
agctttgatg aaatggctaa atatgacctt ccagccacaa tcgacttcat tgtaaagaaa    480
actggacaga agcagctaca ctatgttggc cattcccagg gcaccaccat tggttttatt    540
gccttttcca ccaatcccag cctggctaaa agaatcaaaa ccttctatgc tctagctcct    600
gttgccactg tgaagtatac aaaaagcctt ataaacaaac ttagatttgt tcctcaatcc    660
ctcttcaagt ttatatttgg tgacaaaata ttctacccac acaacttctt tgatcaattt    720
cttgctactg aagtgtgctc ccgtgagatg ctgaatctcc tttgcagcaa tgccttattt    780
ataatttgtg gatttgacag taagaacttt aacacgagtc gcttggatgt gtatctatca    840
cataatccag caggaacttc tgttcaaaac atgttccatt ggacccaggc tgttaagtct    900
gggaaattcc aagcttatga ctggggaagc ccagttcaga ataggatgca ctatgatcag    960
tcccaacctc cctactacaa tgtgacagcc atgaatgtac aattgcagt gtggaacggt   1020
ggcaaggacc tgttggctga cccccaagat gttggccttt tgcttccaaa actccccaat   1080
cttatttacc acaaggagat tccttttttac aatcacttgg actttatctg ggcaatggat   1140
gccctcaag aagtttacaa tgacattgtt tctatgatat cagaagataa aaagtag       1197
```

<210> SEQ ID NO 19
<211> LENGTH: 397
<212> TYPE: PRT
<213> ORGANISM: Bos taurus

<400> SEQUENCE: 19

```
Met Trp Trp Leu Leu Val Thr Val Cys Phe Ile His Met Ser Gly Asn
1               5                   10                  15

Ala Phe Cys Phe Leu Gly Lys Ile Ala Lys Asn Pro Glu Ala Ser Met
            20                  25                  30

Asn Val Ser Gln Met Ile Ser Tyr Trp Gly Tyr Pro Ser Glu Met His
        35                  40                  45

Lys Val Ile Thr Ala Asp Gly Tyr Ile Leu Gln Val Tyr Arg Ile Pro
    50                  55                  60

His Gly Lys Asn Asn Ala Asn His Leu Gly Gln Arg Pro Val Val Phe
65                  70                  75                  80

Leu Gln His Gly Leu Leu Gly Ser Ala Thr Asn Trp Ile Ser Asn Leu
                85                  90                  95

Pro Lys Asn Ser Leu Gly Phe Leu Leu Ala Asp Ala Gly Tyr Asp Val
```

```
                        100                 105                 110
Trp Leu Gly Asn Ser Arg Gly Asn Thr Trp Ala Gln Glu His Leu Tyr
                115                 120                 125

Tyr Ser Pro Asp Ser Pro Glu Phe Trp Ala Phe Ser Phe Asp Glu Met
            130                 135                 140

Ala Glu Tyr Asp Leu Pro Ser Thr Ile Asp Phe Ile Leu Arg Arg Thr
145                 150                 155                 160

Gly Gln Lys Lys Leu His Tyr Val Gly His Ser Gln Gly Thr Thr Ile
                165                 170                 175

Gly Phe Ile Ala Phe Ser Thr Ser Pro Thr Leu Ala Glu Lys Ile Lys
            180                 185                 190

Val Phe Tyr Ala Leu Ala Pro Val Ala Thr Val Lys Tyr Thr Lys Ser
                195                 200                 205

Leu Phe Asn Lys Leu Ala Leu Ile Pro His Phe Leu Phe Lys Ile Ile
            210                 215                 220

Phe Gly Asp Lys Met Phe Tyr Pro His Thr Phe Leu Glu Gln Phe Leu
225                 230                 235                 240

Gly Val Glu Met Cys Ser Arg Glu Thr Leu Asp Val Leu Cys Lys Asn
                245                 250                 255

Ala Leu Phe Ala Ile Thr Gly Val Asp Asn Lys Asn Phe Asn Met Ser
            260                 265                 270

Arg Leu Asp Val Tyr Ile Ala His Asn Pro Ala Gly Thr Ser Val Gln
            275                 280                 285

Asn Thr Leu His Trp Arg Gln Ala Val Lys Ser Gly Lys Phe Gln Ala
            290                 295                 300

Phe Asp Trp Gly Ala Pro Tyr Gln Asn Leu Met His Tyr His Gln Pro
305                 310                 315                 320

Thr Pro Pro Ile Tyr Asn Leu Thr Ala Met Asn Val Pro Ile Ala Val
                325                 330                 335

Trp Ser Ala Asp Asn Asp Leu Leu Ala Asp Pro Gln Asp Val Asp Phe
            340                 345                 350

Leu Leu Ser Lys Leu Ser Asn Leu Ile Tyr His Lys Glu Ile Pro Asn
            355                 360                 365

Tyr Asn His Leu Asp Phe Ile Trp Ala Met Asp Ala Pro Gln Glu Val
            370                 375                 380

Tyr Asn Glu Ile Val Ser Leu Met Ala Glu Asp Lys Lys
385                 390                 395

<210> SEQ ID NO 20
<211> LENGTH: 1194
<212> TYPE: DNA
<213> ORGANISM: Bos taurus

<400> SEQUENCE: 20
atgtggtggc tacttgtaac agtgtgtttc atccacatgt ctggaaatgc attttgtttc       60
cttggaaaaa ttgctaagaa ccctgaagcc agtatgaatg ttagtcagat gatttcctac      120
tggggctacc caagtgagat gcataaagtt ataactgcgg atggttatat ccttcaggtc      180
tatcggattc ctcatggaaa gaataatgct aatcatttag gtcagagacc tgttgtgttt      240
ctgcagcatg gtcttcttgg atcagccaca aactggattt ccaacctgcc caagaacagc      300
ctgggcttcc tcctggcaga tgctggttat gacgtgtggc tggggaacag cagaggaaac      360
acctgggccc aggaacattt atactattca ccagactccc cggaattctg ggctttcagc      420
tttgatgaaa tggcggaata tgaccttcca tctacaattg atttcatctt aaggagaaca      480
```

```
ggacagaaga agctacacta tgttggccat tcccaaggca ccaccattgg ttttatcgcc    540
ttttctacca gtcccacatt ggctgaaaaa atcaaagtct tctatgcatt agccccagtt    600
gccacagtga agtacaccaa gagcctgttt aacaaacttg cacttattcc tcacttcctc    660
ttcaagatta tatttggtga caaaatgttc tacccacaca cttttttgga caatttcttt    720
ggtgttgaaa tgtgctcccg tgagacactg gatgtccttt gtaagaatgc cttgtttgcc    780
attactggag ttgacaataa aaacttcaac atgagtcgct tagatgtgta tatagcacat    840
aatccagcag gaacttctgt tcaaaacacc ctccactgga gacaggctgt taagtctggg    900
aaattccaag cttttgactg gggagcccca tatcagaacc taatgcatta tcatcagccc    960
acacctccca tctacaattt aacagccatg aatgtcccaa ttgcagtatg gagtgctgac   1020
aatgacctgt tggctgaccc tcaggatgtt gactttctgc tttcaaaact ctctaatctc   1080
atttaccaca aggaaattcc aaattacaat cacttggact ttatctgggc aatggatgca   1140
cctcaagaag tttacaatga aattgtttct ttgatggccg aagacaaaaa gtag         1194
```

```
<210> SEQ ID NO 21
<211> LENGTH: 395
<212> TYPE: PRT
<213> ORGANISM: Mus musculus

<400> SEQUENCE: 21

Met Trp Leu Leu Leu Val Thr Ser Val Leu Ser Ala Phe Gly Gly Ala
1               5                   10                  15

His Gly Leu Phe Gly Lys Leu Gly Pro Lys Asn Pro Glu Ala Asn Met
            20                  25                  30

Asn Val Ser Gln Met Ile Thr Tyr Trp Gly Tyr Pro Ser Glu Glu Tyr
        35                  40                  45

Glu Val Val Thr Glu Asp Gly Tyr Ile Leu Gly Val Tyr Arg Ile Pro
    50                  55                  60

Tyr Gly Lys Lys Asn Ser Glu Asn Ile Gly Lys Arg Pro Val Ala Tyr
65                  70                  75                  80

Leu Gln His Gly Leu Ile Ala Ser Ala Thr Asn Trp Ile Thr Asn Leu
                85                  90                  95

Pro Asn Asn Ser Leu Ala Phe Ile Leu Ala Asp Ala Gly Tyr Asp Val
            100                 105                 110

Trp Leu Gly Asn Ser Arg Gly Asn Thr Trp Ser Arg Lys Asn Val Tyr
        115                 120                 125

Tyr Ser Pro Asp Ser Val Glu Phe Trp Ala Phe Ser Phe Asp Glu Met
    130                 135                 140

Ala Lys Tyr Asp Leu Pro Ala Thr Ile Asp Phe Ile Val Gln Lys Thr
145                 150                 155                 160

Gly Gln Glu Lys Ile His Tyr Val Gly His Ser Gln Gly Thr Thr Ile
                165                 170                 175

Gly Phe Ile Ala Phe Ser Thr Asn Pro Ala Leu Ala Lys Lys Ile Lys
            180                 185                 190

Arg Phe Tyr Ala Leu Ala Pro Val Ala Thr Val Lys Tyr Thr Glu Ser
        195                 200                 205

Pro Phe Lys Lys Ile Ser Leu Ile Pro Lys Phe Leu Leu Lys Val Ile
    210                 215                 220

Phe Gly Asn Lys Met Phe Met Pro His Asn Tyr Leu Asp Gln Phe Leu
225                 230                 235                 240

Gly Thr Glu Val Cys Ser Arg Glu Leu Leu Asp Leu Leu Cys Ser Asn
                245                 250                 255
```

-continued

```
Ala Leu Phe Ile Phe Cys Gly Phe Asp Lys Lys Asn Leu Asn Val Ser
            260                 265                 270

Arg Phe Asp Val Tyr Leu Gly His Asn Pro Ala Gly Thr Ser Thr Gln
            275                 280                 285

Asp Leu Phe His Trp Ala Gln Leu Ala Lys Ser Gly Lys Leu Gln Ala
            290                 295                 300

Tyr Asn Trp Gly Ser Pro Leu Gln Asn Met Leu His Tyr Asn Gln Lys
305                 310                 315                 320

Thr Pro Pro Tyr Tyr Asp Val Ser Ala Met Thr Val Pro Ile Ala Val
                325                 330                 335

Trp Asn Gly Gly His Asp Ile Leu Ala Asp Pro Gln Asp Val Ala Met
            340                 345                 350

Leu Leu Pro Lys Leu Pro Asn Leu Leu Tyr His Lys Glu Ile Leu Pro
            355                 360                 365

Tyr Asn His Leu Asp Phe Ile Trp Ala Met Asp Ala Pro Gln Glu Val
            370                 375                 380

Tyr Asn Glu Ile Val Thr Met Met Ala Glu Asp
385                 390                 395
```

<210> SEQ ID NO 22
<211> LENGTH: 1188
<212> TYPE: DNA
<213> ORGANISM: Mus musculus

<400> SEQUENCE: 22

```
atgtggctgc tattagtaac aagtgtgcta tctgcatttg gaggtgcaca tggcctattt    60
ggaaaactgg gtcccaaaaa ccctgaagca acatgaatg ttagtcagat gataacttac    120
tggggatatc caagtgagga atatgaagtt gttactgaag atggctacat tctgggggtc   180
tatagaattc cttatgggaa gaaaaattct gagaatatcg gcaagagacc tgtggcatat   240
ttgcagcatg gtttgattgc atcagccaca aactggatta caaatctgcc aaacaacagc   300
ctggccttca ttctagcaga tgctggctat gatgtgtggc tggggaacag tcgagggaat   360
acatggtccc ggaaaaatgt atactattca ccagactcag ttgaattctg ggctttcagc   420
tttgatgaaa tggctaaata tgaccttcca gccaccatag acttcattgt acagaaaact   480
ggacaagaga agatacacta tgttggtcac tctcagggca ccactatcgg ttttattgcc   540
ttttctacca atcctgctct ggctaaaaaa atcaagaggt tttatgcatt agctccagtt   600
gctactgtga agtatacaga aagtcccttt aaaaagattt cacttattcc taagtttctt   660
ctcaaggtga tatttggtaa caaaatgttc atgccccaca actacttaga tcaatttctt   720
ggtacggaag tgtgctcacg ggagctgcta gatcttctct gcagcaacgc tttattcatc   780
ttctgtggat ttgacaagaa aaacttaaat gtgagtcgct tgatgtgta tctagggcat   840
aatccagcag gaacatctac tcaagacctt ttccactggg cacagcttgc taaatctggg   900
aagcttcaag cctataactg gggaagtcca ttacagaaca tgttacacta caatcagaaa   960
acgcctccct actatgatgt gtcagccatg accgtgccaa ttgcagtgtg gaacggtggc  1020
catgacatcc tggctgatcc ccaagatgtc gcaatgctgc ttcccaaact ccccaacctt  1080
ctgtaccata ggagattgct tccctacaat cacctggact catctgggc gatggatgcg  1140
cctcaagagg tttacaatga gatagttacc atgatggcag aagactaa               1188
```

<210> SEQ ID NO 23
<211> LENGTH: 395
<212> TYPE: PRT
<213> ORGANISM: Rattus norvegicus

<400> SEQUENCE: 23

Met Trp Leu Leu Leu Ile Thr Ser Val Ile Ser Thr Phe Gly Gly Ala
1               5                   10                  15

His Gly Leu Phe Gly Lys Leu Gly Pro Gly Asn Pro Glu Ala Asn Met
            20                  25                  30

Asn Ile Ser Gln Met Ile Thr Tyr Trp Gly Tyr Pro Cys Gln Glu Tyr
        35                  40                  45

Glu Val Val Thr Glu Asp Gly Tyr Ile Leu Gly Val Tyr Arg Ile Pro
    50                  55                  60

His Gly Lys Asn Asn Ser Glu Asn Ile Gly Lys Arg Pro Val Val Tyr
65                  70                  75                  80

Leu Gln His Gly Leu Ile Ala Ser Ala Thr Asn Trp Ile Ala Asn Leu
                85                  90                  95

Pro Asn Asn Ser Leu Ala Phe Met Leu Ala Asp Ala Gly Tyr Asp Val
            100                 105                 110

Trp Leu Gly Asn Ser Arg Gly Asn Thr Trp Ser Arg Lys Asn Val Tyr
        115                 120                 125

Tyr Ser Pro Asp Ser Val Glu Phe Trp Ala Phe Ser Phe Asp Glu Met
130                 135                 140

Ala Lys Tyr Asp Leu Pro Ala Thr Ile Asn Phe Ile Val Gln Lys Thr
145                 150                 155                 160

Gly Gln Glu Lys Ile His Tyr Val Gly His Ser Gln Gly Thr Thr Ile
                165                 170                 175

Gly Phe Ile Ala Phe Ser Thr Asn Pro Thr Leu Ala Lys Lys Ile Lys
            180                 185                 190

Thr Phe Tyr Ala Leu Ala Pro Val Ala Thr Val Lys Tyr Thr Gln Ser
        195                 200                 205

Pro Leu Lys Lys Ile Ser Phe Ile Pro Thr Phe Leu Phe Lys Leu Met
210                 215                 220

Phe Gly Lys Lys Met Phe Leu Pro His Thr Tyr Phe Asp Asp Phe Leu
225                 230                 235                 240

Gly Thr Glu Val Cys Ser Arg Glu Val Leu Asp Leu Leu Cys Ser Asn
                245                 250                 255

Thr Leu Phe Ile Phe Cys Gly Phe Asp Lys Lys Asn Leu Asn Val Ser
            260                 265                 270

Arg Phe Asp Val Tyr Leu Gly His Asn Pro Ala Gly Thr Ser Val Gln
        275                 280                 285

Asp Phe Leu His Trp Ala Gln Leu Val Arg Ser Gly Lys Phe Gln Ala
290                 295                 300

Phe Asn Trp Gly Ser Pro Ser Gln Asn Met Leu His Tyr Asn Gln Lys
305                 310                 315                 320

Thr Pro Pro Glu Tyr Asp Val Ser Ala Met Thr Val Pro Val Ala Val
                325                 330                 335

Trp Asn Gly Gly Asn Asp Ile Leu Ala Asp Pro Gln Asp Val Ala Met
            340                 345                 350

Leu Leu Pro Lys Leu Ser Asn Leu Leu Phe His Lys Glu Ile Leu Ala
        355                 360                 365

Tyr Asn His Leu Asp Phe Ile Trp Ala Met Asp Ala Pro Gln Glu Val
370                 375                 380

Tyr Asn Glu Met Ile Ser Met Met Ala Glu Asp
385                 390                 395

<210> SEQ ID NO 24

<211> LENGTH: 1188
<212> TYPE: DNA
<213> ORGANISM: Rattus norvegicus

<400> SEQUENCE: 24

```
atgtggctgt tattaataac aagtgtgata tcaacattcg gaggtgcaca tggcctattt      60
ggaaaactgg gtcctggaaa ccctgaagca aatatgaata ttagtcagat gataacttac     120
tggggatatc catgtcaaga atatgaagtt gttactgaag atggctacat tctgggggtc     180
tacagaattc ctcatgggaa gaataattct gaaaatatag caagagacc tgtggtgtat      240
ttgcagcatg gtttgatcgc atcagccaca aactggattg caaatctacc aaacaacagc     300
ctggccttta tgctagcaga cgctggctat gatgtgtggc tggggaacag tcgaggaaat     360
acatggtcca ggaaaaatgt atactactca ccagactcag ttgaattctg ggctttcagc     420
tttgatgaaa tggctaaata tgaccttccc gccacaataa acttcattgt acagaaaact     480
ggacaagaga agatacacta tgttggtcat tctcagggca ccactattgg tttcattgcc     540
ttttctacca atcctacact ggccaaaaaa atcaagacgt tttatgcatt agctccagtt     600
gctaccgtga agtatacaca aagtcccttg aaaaagattt catttattcc tacatttctt     660
ttcaagctta tgtttggcaa gaaaatgttc ctgccccaca cctactttga tgactttctt     720
ggtaccgaag tgtgctcacg ggaggttcta gatcttctct gcagcaacac tttattcatc     780
ttctgtggat ttgacaagaa aaacttaaat gtgagtcgtt ttgatgtgta tctagggcat     840
aatccagcag ggacatctgt tcaagacttt ctccactggg cacagcttgt tagatctggg     900
aaatttcaag ccttcaactg gggaagccca tcccagaaca tgttacacta caaccagaaa     960
acgcctcctg aatatgatgt gtcagccatg actgtgccag ttgcagtgtg gaacggtggc    1020
aatgacatcc tggctgatcc ccaagatgtc gccatgctgc ttcccaaact ctccaacctc    1080
ctgttccata ggagattcct tgcctacaat cacctggact tcatctgggc aatggatgcc    1140
cctcaagagg tttacaatga gatgatttcc atgatggcag aagactaa                 1188
```

<210> SEQ ID NO 25
<211> LENGTH: 398
<212> TYPE: PRT
<213> ORGANISM: Canis lupus familiaris

<400> SEQUENCE: 25

```
Met Trp Leu Leu Leu Thr Ala Ala Ser Val Ile Ser Thr Leu Gly Thr
1               5                   10                  15

Thr His Gly Leu Phe Gly Lys Leu His Pro Thr Asn Pro Glu Val Thr
            20                  25                  30

Met Asn Ile Ser Gln Met Ile Thr Tyr Trp Gly Tyr Pro Ala Glu Glu
        35                  40                  45

Tyr Glu Val Val Thr Glu Asp Gly Tyr Ile Leu Gly Ile Asp Arg Ile
    50                  55                  60

Pro Tyr Gly Arg Lys Asn Ser Glu Asn Ile Gly Arg Arg Pro Val Ala
65                  70                  75                  80

Phe Leu Gln His Gly Leu Leu Ala Ser Ala Thr Asn Trp Ile Ser Asn
                85                  90                  95

Leu Pro Asn Asn Ser Leu Ala Phe Ile Leu Ala Asp Ala Gly Tyr Asp
            100                 105                 110

Val Trp Leu Gly Asn Ser Arg Gly Asn Thr Trp Ala Arg Arg Asn Leu
        115                 120                 125

Tyr Tyr Ser Pro Asp Ser Val Glu Phe Trp Ala Phe Ser Phe Asp Glu
    130                 135                 140
```

```
Met Ala Lys Tyr Asp Leu Pro Ala Thr Ile Asp Phe Ile Leu Lys Lys
145                 150                 155                 160

Thr Gly Gln Asp Lys Leu His Tyr Val Gly His Ser Gln Gly Thr Thr
            165                 170                 175

Ile Gly Phe Ile Ala Phe Ser Thr Asn Pro Lys Leu Ala Lys Arg Ile
            180                 185                 190

Lys Thr Phe Tyr Ala Leu Ala Pro Val Ala Thr Val Lys Tyr Thr Glu
            195                 200                 205

Thr Leu Leu Asn Lys Leu Met Leu Val Pro Ser Phe Leu Phe Lys Leu
            210                 215                 220

Ile Phe Gly Asn Lys Ile Phe Tyr Pro His His Phe Phe Asp Gln Phe
225                 230                 235                 240

Leu Ala Thr Glu Val Cys Ser Arg Glu Thr Val Asp Leu Leu Cys Ser
            245                 250                 255

Asn Ala Leu Phe Ile Ile Cys Gly Phe Asp Thr Met Asn Leu Asn Met
            260                 265                 270

Ser Arg Leu Asp Val Tyr Leu Ser His Asn Pro Ala Gly Thr Ser Val
            275                 280                 285

Gln Asn Val Leu His Trp Ser Gln Ala Val Lys Ser Gly Lys Phe Gln
            290                 295                 300

Ala Phe Asp Trp Gly Ser Pro Val Gln Asn Met Met His Tyr His Gln
305                 310                 315                 320

Ser Met Pro Pro Tyr Tyr Asn Leu Thr Asp Met His Val Pro Ile Ala
            325                 330                 335

Val Trp Asn Gly Gly Asn Asp Leu Leu Ala Asp Pro His Asp Val Asp
            340                 345                 350

Leu Leu Leu Ser Lys Leu Pro Asn Leu Ile Tyr His Arg Lys Ile Pro
            355                 360                 365

Pro Tyr Asn His Leu Asp Phe Ile Trp Ala Met Asp Ala Pro Gln Ala
            370                 375                 380

Val Tyr Asn Glu Ile Val Ser Met Met Gly Thr Asp Asn Lys
385                 390                 395

<210> SEQ ID NO 26
<211> LENGTH: 1197
<212> TYPE: DNA
<213> ORGANISM: Canis lupus familiaris

<400> SEQUENCE: 26
atgtggctgc tattaacagc ggcgagtgtg atatctacac ttggaaccac acatggttta      60
tttggaaaat acatcccac aaaccctgaa gtgaccatga atataagtca gatgatcacc     120
tactggggat acccagctga ggaatatgaa gttgtgaccg aagacggtta tatccttggg     180
atcgacagaa ttccttatgg gaggaaaaat tcagagaata taggccggag acctgttgca     240
tttttgcaac acggtttgct cgcatcagcc acaaactgga tctccaacct gcccaacaac     300
agcctggcct tcatcctggc cgacgccggg tacgacgtgt ggctggggaa cagcaggggc     360
aacacctggg ccaggaggaa tctgtactac tcgcccgact ccgtcgaatt ctgggctttc     420
agctttgacg agatggctaa atatgaccctt cccgccacca ttgacttcat cttgaagaaa     480
acgggacagg acaagctaca ctacgttggc cattcccagg gcaccaccat ggtttcatc     540 gccttttcca ccaatcccaa gctggcgaaa cggatcaaaa ccttctatgc attagctccc     600
gttgccaccg tgaagtacac cgaaaccctg ttaaacaaac tcatgctcgt cccttcgttc     660
ctcttcaagc ttatatttgg aaacaaaata ttctacccac accacttctt tgatcaattt     720
```

-continued

```
ctcgccaccg aggtatgctc ccgcgagacg gtggatctcc tctgcagcaa cgccctgttt    780
atcatttgtg gatttgacac tatgaacttg aacatgagtc gcttggatgt gtatctgtca    840
cataatccag caggaacatc ggttcagaac gtgctccact ggtcccaggc tgttaagtct    900
gggaagttcc aagcttttga ctggggaagc ccagttcaga acatgatgca ctatcatcag    960
agcatgcctc cctactacaa cctgacagac atgcatgtgc caatcgcagt gtggaacggt   1020
ggcaacgact tgctggccga ccctcacgat gttgaccttt gctttccaa gctccccaat    1080 ctcatttacc acaggaagat tcctccttac aatcacttgg actttatctg gccatggat    1140 gcccctcaag cggtttacaa tgaaattgtt tccatgatgg gaacagataa taagtag     1197
```

<210> SEQ ID NO 27
<211> LENGTH: 297
<212> TYPE: PRT
<213> ORGANISM: Aspergillus niger

<400> SEQUENCE: 27

```
Met Phe Ser Gly Arg Phe Gly Val Leu Leu Thr Ala Leu Ala Ala Leu
1               5                   10                  15

Ser Ala Ala Ala Pro Thr Pro Leu Asp Val Arg Ser Val Ser Thr Ser
                20                  25                  30

Thr Leu Asp Glu Leu Gln Leu Phe Ser Gln Trp Ser Ala Ala Ala Tyr
            35                  40                  45

Cys Ser Asn Asn Ile Asp Ser Asp Ser Asn Val Thr Cys Thr Ala
        50                  55                  60

Asp Ala Cys Pro Ser Val Glu Glu Ala Ser Thr Lys Met Leu Leu Glu
65                  70                  75                  80

Phe Asp Leu Thr Asn Asn Phe Gly Gly Thr Ala Gly Phe Leu Ala Ala
                85                  90                  95

Asp Asn Thr Asn Lys Arg Leu Val Val Ala Phe Arg Gly Ser Ser Thr
            100                 105                 110

Ile Lys Asn Trp Ile Ala Asp Leu Asp Phe Ile Leu Gln Asp Asn Asp
        115                 120                 125

Asp Leu Cys Thr Gly Cys Lys Val His Thr Gly Phe Trp Lys Ala Trp
130                 135                 140

Glu Ala Ala Ala Asp Asn Leu Thr Ser Lys Ile Lys Ser Ala Met Ser
145                 150                 155                 160

Thr Tyr Ser Gly Tyr Thr Leu Tyr Phe Thr Gly His Ser Leu Gly Gly
                165                 170                 175

Ala Leu Ala Thr Leu Gly Ala Thr Val Leu Arg Asn Asp Gly Tyr Ser
            180                 185                 190

Val Glu Leu Tyr Thr Tyr Gly Cys Pro Arg Val Gly Asn Tyr Ala Leu
        195                 200                 205

Ala Glu His Ile Thr Ser Gln Gly Ser Gly Ala Asn Phe Arg Val Thr
210                 215                 220

His Leu Asn Asp Ile Val Pro Arg Leu Pro Pro Met Asp Phe Gly Phe
225                 230                 235                 240

Ser Gln Pro Ser Pro Glu Tyr Trp Ile Thr Ser Gly Thr Gly Ala Ser
                245                 250                 255

Val Thr Ala Ser Asp Ile Glu Leu Ile Glu Gly Ile Asn Ser Thr Ala
            260                 265                 270

Gly Asn Ala Gly Glu Ala Thr Val Asp Val Leu Ala His Leu Trp Tyr
        275                 280                 285

Phe Phe Ala Ile Ser Glu Cys Leu Leu
```

```
                    290                 295

<210> SEQ ID NO 28
<211> LENGTH: 526
<212> TYPE: PRT
<213> ORGANISM: Ricinus communis

<400> SEQUENCE: 28

Met Asp Asp Ala Gly Lys Ile Thr Ser Thr Ser His Leu Ile Val Ser
1               5                   10                  15

Pro Asp Glu Gly Thr Phe Leu Asp Leu Phe Lys His Ile Val Leu Ser
            20                  25                  30

Asp Leu Gly Ser Gly Ala Lys Phe Phe Arg Ala Ser Asp Gln Arg Val
        35                  40                  45

Pro Ala Thr Ala Ala Tyr Tyr Ser Arg Trp Pro Val Ser Val Phe Ile
    50                  55                  60

Cys Lys Ile Leu Gln Leu Phe Gln Met Pro Ala Ala Met Leu Gly His
65                  70                  75                  80

Leu Thr Asp Phe Leu Leu Asn Phe Tyr Tyr Gln Asn His Gly Phe Leu
                85                  90                  95

Gly Ile Leu Arg Asn Ile Phe Leu Ile Arg Leu Lys Ile Pro Lys Arg
            100                 105                 110

Gly Glu Ala Asp Phe Ile Ser Thr Ile Gly Tyr Leu Asp Ser Arg Met
        115                 120                 125

Asp Leu His Gly Thr Pro Met Val Ser His Gln Ala Asp Glu Val Ile
    130                 135                 140

Ser Asn Ala Asp Asn Pro Ser Leu Lys Glu Gly His Asn Ser Lys Ile
145                 150                 155                 160

Lys Gly Ala Leu Gly Asn Arg Ser Leu Met Asp Leu Cys Ile Met Ala
                165                 170                 175

Ser Lys Leu Ala Tyr Glu Asn Thr Lys Val Val Glu Arg Val Val Ala
            180                 185                 190

Glu His Trp Lys Met His Phe Val Ala Asp Tyr Gly Gly Met Asn Tyr
        195                 200                 205

Phe Gln Asp Ala Arg Asn Thr His Ala Phe Ile Phe Cys Asp Lys Pro
    210                 215                 220

Lys Asp Ala Asn Leu Ile Val Ile Ser Phe Arg Gly Thr Gly Pro Phe
225                 230                 235                 240

Ser Ile Pro Asn Trp Cys Thr Asp Phe Asp Phe Ser Leu Val Gly Leu
                245                 250                 255

Gly Asp Ala Gly Ser Val His Val Gly Phe Leu Glu Ala Met Gly Leu
            260                 265                 270

Gly His Arg Asn Ser Ile Ser Ser Phe Glu Thr Ser Ile Asn Thr Lys
        275                 280                 285

Ser Pro Gly Ser Ile Thr Glu Leu Arg Lys Glu Ser Glu Met Ala Pro
    290                 295                 300

Asp His Leu Val Trp Ala Tyr Asp Gly Val Tyr Phe Leu Ala Ala Ser
305                 310                 315                 320

Thr Leu Lys Gly Leu Leu Lys Asp His Lys Asn Ala Lys Phe Val Val
                325                 330                 335

Thr Gly His Ser Leu Gly Gly Ala Leu Ala Ile Leu Phe Thr Cys Ile
            340                 345                 350

Leu Glu Ile Gln Gln Glu Thr Glu Val Leu Asp Arg Leu Leu Asn Val
        355                 360                 365

Tyr Thr Phe Gly Gln Pro Arg Ile Gly Asn Tyr Asn Leu Gly Tyr Phe
```

```
                370              375              380
Met Gln Asn Arg Leu Asn Phe Pro Glu Arg Arg Tyr Phe Arg Val Val
385              390              395              400

Tyr Cys Asn Asp Met Val Pro Arg Val Pro Phe Asp Asp Val Phe Phe
                405              410              415

Thr Phe Glu His Phe Gly Thr Cys Ile Tyr Tyr Asp Ser Arg Phe Phe
            420              425              430

Gly Tyr Phe Thr Lys Glu Glu Pro Ser Arg Asn Pro Phe Gly Ile Glu
        435              440              445

Asn Ala Ile Ser Ala His Ile Thr Ala Trp Trp Glu Leu Trp Arg Ser
450              455              460

Phe Ile Leu Asn His Val Tyr Gly Ala Glu Tyr Lys Glu Thr Trp Glu
465              470              475              480

Ser Arg Met Phe Arg Ile Leu Gly Leu Phe Leu Pro Gly Val Ala Ala
                485              490              495

His Ser Pro Val Asn Tyr Val Asn Ser Val Arg Leu Gly Arg Glu Leu
            500              505              510

Ala Ile Pro Leu Met Ser Leu Lys Met Met Ala Gln Gly Tyr
        515              520              525

<210> SEQ ID NO 29
<211> LENGTH: 1870
<212> TYPE: DNA
<213> ORGANISM: Ricinus communis

<400> SEQUENCE: 29
ctaaagccat ggatgatgct ggtaaaatca cttccacaag ccatctcata gtgagcccag      60
atgaaggaac cttttggac ctgttcaagc acattgtgct gagtgatttg ggcagtggag     120
ccaaattctt tagggcttca gatcagagag tgcctgctac ggcagcatat tatagcaggt     180
ggcctgtttc agttttcatt tgcaaaatac ttcaactttt ccagatgcca gccgcgatgc     240
ttggtcatct tactgatttc ttgctcaact tctattatca gaatcatggc ttccttggca     300
tactcagaaa catcttctta taagactga agataccaaa aagaggtgaa gccgacttta     360
taagcacgat agggtattta gattcacgaa tggaccttca cgggacgcca atggtgtcgc     420
accaggcaga cgaagtgatt tcaaatgcag ataatccaag cctgaaagaa gggcacaatt     480
caaagataaa aggagccctt gggaaccgat ctctcatgga tctttgtatc atggcgtcaa     540
agcttgctta tgaaaatacc aaagttgttg aaagagtagt tgccgaacat tggaagatgc     600
atttcgtggc tgactatggg ggcatgaatt atttccaaga tgcaaggaac actcatgcgt     660
tcatcttttg tgacaagcca aaagatgcaa acttgatagt gatcagcttc agaggcacag     720 gacctttag tataccaaat tggtgtactg attttgattt ctccttagtt gggttgggag     780
acgcaggaag tgtccatgtt ggattcttag aagcaatggg tttgggtcac agaaattcta     840
tttccagctt tgagactagc attaacacaa agtcgccagg aagcataacc gaattaagga     900
aagagtccga gatggctccg gaccacttgg tatgggcata tgatggtgtt tactttcttg     960
cggcatcgac gctcaaggga ttactaaaag accacaagaa cgcaaaattt gtagtcactg    1020
ggcatagctt aggtggtgca cttgctatac tgttcacatg cattcttgag atacagcagg    1080
agacagaggt gcttgacaga ctgctaaatg tatacacatt cggacagcct aggattggga    1140
actataatct tggttacttc atgcagaacc gtctcaattt tccagaacgt aggtatttca    1200
gggtggttta ctgcaatgac atggttccta gggtgccttt cgatgatgtc ttcttcactt    1260
tcgagcattt cggaacctgc atttactatg atagccgctt cttggctac tttaccaaag    1320
```

```
aggagcccag cagaaaccct ttcggaatag aaaatgccat cagtgcgcac atcaccgcct   1380
ggtgggagct ctggagaagt ttcatattaa atcacgtata tggcgcagaa tacaaggaga   1440
cctgggaatc cagaatgttc aggatattgg gactgtttct ccctggtgtt gcagctcata   1500
gtcctgtgaa ttatgtcaat tctgtcaggc ttggaaggga gcttgcaatt cccttgatgt   1560
ctctgaaaat gatggcacaa ggttactaga attatcgtta taaagtctaa gagatgatca   1620
ttaatgataa atggttcact ctttgccaaa aaagaaaaa taatcaaaag gcttacgcta   1680
ttgtaataaa aggatagctg tttcatgaac aggtcgccta gggttgtggt gtggagcttt   1740
gatatgcata tatgcatata tggcctgttt gtttgtcagt ttgttttct ctttaaacaa   1800 aatgaaatgc ggtagttcaa taaaaaggaa cgttgagtag ttttgggtt gccaaaaaaa   1860 aaaaaaaaa                                                          1870
```

<210> SEQ ID NO 30
<211> LENGTH: 334
<212> TYPE: PRT
<213> ORGANISM: Yarrowia lipolytica

<400> SEQUENCE: 30

```
Met Lys Leu Ser Thr Ile Leu Phe Thr Ala Cys Ala Thr Leu Ala Ala
1               5                   10                  15

Ala Leu Pro Ser Pro Ile Thr Pro Ser Glu Ala Ala Val Leu Gln Lys
            20                  25                  30

Arg Val Tyr Thr Ser Thr Glu Thr Ser His Ile Asp Gln Glu Ser Tyr
        35                  40                  45

Asn Phe Phe Glu Lys Tyr Ala Arg Leu Ala Asn Ile Gly Tyr Cys Val
    50                  55                  60

Gly Pro Gly Thr Lys Ile Phe Lys Pro Phe Asn Cys Gly Leu Gln Cys
65                  70                  75                  80

Ala His Phe Pro Asn Val Glu Leu Ile Glu Glu Phe His Asp Pro Arg
                85                  90                  95

Leu Ile Phe Asp Val Ser Gly Tyr Leu Ala Val Asp His Ala Ser Lys
            100                 105                 110

Gln Ile Tyr Leu Val Ile Arg Gly Thr His Ser Leu Glu Asp Val Ile
        115                 120                 125

Thr Asp Ile Arg Ile Met Gln Ala Pro Leu Thr Asn Phe Asp Leu Ala
    130                 135                 140

Ala Asn Ile Ser Ser Thr Ala Thr Cys Asp Asp Cys Leu Val His Asn
145                 150                 155                 160

Gly Phe Ile Gln Ser Tyr Asn Asn Thr Tyr Asn Gln Ile Gly Pro Lys
                165                 170                 175

Leu Asp Ser Val Ile Glu Gln Tyr Pro Asp Tyr Gln Ile Ala Val Thr
            180                 185                 190

Gly His Ser Leu Gly Gly Ala Ala Ala Leu Leu Phe Gly Ile Asn Leu
        195                 200                 205

Lys Val Asn Asp His Asp Pro Leu Val Val Thr Leu Gly Gln Pro Ile
    210                 215                 220

Val Gly Asn Ala Gly Phe Ala Asn Trp Val Asp Lys Leu Phe Phe Gly
225                 230                 235                 240

Gln Glu Asn Pro Asp Val Ser Lys Val Ser Lys Asp Arg Lys Leu Tyr
                245                 250                 255

Arg Ile Thr His Arg Gly Asp Ile Val Pro Gln Val Pro Phe Trp Asp
            260                 265                 270
```

```
Gly Tyr Gln His Cys Ser Gly Glu Val Phe Ile Asp Trp Pro Leu Ile
            275                 280                 285

His Pro Pro Leu Ser Asn Val Val Met Cys Gln Gly Gln Ser Asn Lys
        290                 295                 300

Gln Cys Ser Ala Gly Asn Thr Leu Leu Gln Gly Val Asn Val Ile Gly
305                 310                 315                 320

Asn His Leu Gln Tyr Phe Val Thr Glu Gly Val Cys Gly Ile
                325                 330

<210> SEQ ID NO 31
<211> LENGTH: 1005
<212> TYPE: DNA
<213> ORGANISM: Yarrowia lipolytica

<400> SEQUENCE: 31
atgaagcttt ccaccatcct tttcacagcc tgcgctaccc tggctgccgc cctcccttcc      60
cccatcactc cttctgaggc cgcagttctc cagaagcgag tgtacacctc taccgagacc     120
tctcacattg accaggagtc ctacaacttc tttgagaagt acgcccgact cgcaaacatt     180
ggatattgtg ttggtcccgg cactaagatc ttcaagccct caactgtggg cctgcaatgt     240
gcccacttcc ccaacgttga gctcatcgag gagttccacg accccgtctc atctttgat      300 gtttctggtt acctcgctgt tgatcatgcc tccaagcaga tctaccttgt tattcgagga     360
acccactctc tggaggacgt cataaccgac atccgaatca tgcaggctcc tctgacgaac     420
tttgatcttg ctgctaacat ctcttctact gctacttgtg atgactgtct tgtccacaat     480
ggcttcatcc agtcctacaa caacacctac aatcagatcg gccccaagct cgactctgtg     540
attgagcagt atcccgacta ccagattgct gtcaccggtc actctctcgg aggagctgca     600
gcccttctgt tcggaatcaa cctcaaggtt aacggccacg atccctcgt tgttactctt     660 ggtcagccca ttgtcggtaa cgctggcttt gctaactggg tcgataaact cttctttggc     720
caggagaacc ccgatgtctc caaggtgtcc aaagaccgaa agctctaccg aatcacccac     780
cgaggagata tcgtccctca gtgcccttc tgggacggtt accagcactg ctctggtgag     840
gtctttattg actggcccct gatccaccct cctctctcca cgttgtcat gtgccagggc     900 cagagcaata aacagtgctc tgccggtaac actctgctcc agcaggtcaa tgtgattgga     960
aaccatctgc agtacttcgt caccgagggt gtctgtggta tctaa                    1005

<210> SEQ ID NO 32
<211> LENGTH: 366
<212> TYPE: PRT
<213> ORGANISM: Rhizopus arrhizus
<220> FEATURE:
<221> NAME/KEY: MISC_FEATURE
<223> OTHER INFORMATION: Rhizopus arrhizus = Rhizopus oryzae

<400> SEQUENCE: 32

Val Pro Val Ser Gly Lys Ser Gly Ser Ser Asn Thr Ala Val Ser Ala
1               5                   10                  15

Ser Asp Asn Ala Ala Leu Pro Pro Leu Ile Ser Ser Arg Cys Ala Pro
            20                  25                  30

Pro Ser Asn Lys Gly Ser Lys Ser Asp Leu Gln Ala Glu Pro Tyr Asn
        35                  40                  45

Met Gln Lys Asn Thr Glu Trp Tyr Lys Ser His Gly Gly Asn Leu Thr
    50                  55                  60

Ser Ile Gly Lys Arg Asp Asp Asn Leu Val Gly Gly Met Thr Leu Asp
65                  70                  75                  80
```

```
Leu Pro Ser Gly Ala Pro Pro Ile Ser Leu Ser Ser Thr Asn Ser
                85                  90                  95

Ala Ser Asp Gly Gly Lys Val Val Ala Thr Thr Ala Gln Ile Gln
            100                 105                 110

Glu Phe Thr Lys Tyr Ala Gly Ile Ala Ala Thr Ala Tyr Cys Arg Ser
        115                 120                 125

Val Val Pro Gly Asn Lys Trp Asp Cys Val Gln Cys Gln Lys Trp Val
130                 135                 140

Pro Asp Gly Lys Ile Ile Thr Thr Phe Thr Ser Leu Leu Ser Asp Thr
145                 150                 155                 160

Asn Gly Tyr Val Leu Arg Ser Lys Gln Lys Thr Ile Tyr Leu Val
                165                 170                 175

Phe Arg Gly Thr Asn Ser Phe Arg Ser Ala Ile Thr Asp Ile Val Phe
            180                 185                 190

Asn Phe Ser Asp Tyr Lys Pro Val Lys Gly Ala Lys Val His Ala Gly
        195                 200                 205

Phe Leu Ser Ser Tyr Glu Gln Val Val Asn Asp Tyr Phe Pro Val Val
210                 215                 220

Gln Glu Gln Leu Thr Ala His Pro Thr Tyr Lys Val Ile Val Thr Gly
225                 230                 235                 240

His Ser Leu Gly Gly Ala Gln Ala Leu Leu Ala Gly Met Asp Leu Tyr
                245                 250                 255

Gln Arg Glu Pro Gly Leu Ser Pro Lys Asn Leu Ser Ile Phe Thr Val
            260                 265                 270

Gly Gly Pro Arg Val Gly Asn Pro Thr Phe Ala Tyr Tyr Val Glu Ser
        275                 280                 285

Thr Gly Ile Pro Phe Gln Arg Thr Val His Lys Arg Asp Ile Val Pro
290                 295                 300

His Val Pro Pro Gln Ser Phe Gly Phe Leu His Pro Gly Val Glu Ser
305                 310                 315                 320

Trp Met Lys Ser Gly Thr Ser Asn Val Gln Ile Cys Thr Ser Glu Ile
                325                 330                 335

Glu Thr Lys Asp Cys Ser Asn Ser Ile Val Pro Phe Thr Ser Ile Leu
            340                 345                 350

Asp His Leu Ser Tyr Phe Asp Ile Asn Glu Gly Ser Cys Leu
        355                 360                 365

<210> SEQ ID NO 33
<211> LENGTH: 1101
<212> TYPE: DNA
<213> ORGANISM: Rhizopus arrhizus
<220> FEATURE:
<221> NAME/KEY: misc_feature
<223> OTHER INFORMATION: Rhizopus arrhizus = Rhizopus oryzae

<400> SEQUENCE: 33
gttcctgttt ctggtaaatc tggatcttcc aacaccgccg tctctgcatc tgacaatgct      60
gccctccctc ctctcatctc cagccgttgt gctcctcctt ctaacaaggg aagtaaaagc     120
gatctccaag ctgaacctta caacatgcaa agaatacag aatggtataa gtcccatggt      180
ggcaacctga catccatcgg aaagcgtgat gacaacttgg ttggtggcat gactttggac     240
ttacccagcg gtgctcctcc tatcagcctc tctagctcta ccaacagcgc ctctgatggt     300
ggtaaggttg ttgctgctac tactgctcag atccaagagt tcaccaagta tgctggtatc     360
gctgccactg cctactgtcg ttctgttgtc cctggtaaca gtgggattg tgtccaatgt     420 caaaagtggg ttcctgatgg caagatcatc actacccttta cctccttgct ttccgataca     480
```

```
aatggttacg tcttgagaag tgataaacaa aagaccattt atcttgtttt ccgtggtacc      540
aactccttca gaagtgccat cactgatatc gtcttcaact tttctgacta caagcctgtc      600
aagggcgcca aagttcatgc tggtttcctt tcctcttatg agcaagttgt caatgactat      660
ttccctgtcg ttcaagaaca attgaccgcc caccctactt ataaggtcat cgttaccggt      720
cactcactcg gtggtgcaca agctttgctt gccggtatgg atctctacca acgtgaacca      780
gggttgtctc ccaagaattt gagcatcttc actgtcggtg gtcctcgtgt tggtaacccc      840
acctttgctt actatgttga atccaccggt atcccttcc aacgtaccgt tcacaagaga       900
gatatcgttc ctcacgttcc tcctcaatcc ttcggattcc ttcatcccgg tgttgaatct      960
tggatgaagt ctggtacttc caacgttcaa atctgtactt ctgaaattga aaccaaggat     1020
tgcagtaact ctatcgttcc tttcacctct atccttgacc acttgagtta ctttgatatc     1080
aacgaaggaa gctgtttgta a                                               1101
```